(12) United States Patent
Godbout et al.

(10) Patent No.: US 10,864,201 B2
(45) Date of Patent: Dec. 15, 2020

(54) HETEROAROMATIC COMPOUNDS AS VANIN INHIBITORS

(71) Applicant: Boehringer Ingelheim International GmbH, Ingelheim am Rhein (DE)

(72) Inventors: Cédrickx Godbout, Attenweiler (DE); Martin Thomas Fleck, Munich (DE); Hannes Fiepko Koolman, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/550,347

(22) Filed: Aug. 26, 2019

(65) Prior Publication Data
US 2020/0069663 A1 Mar. 5, 2020

(30) Foreign Application Priority Data
Aug. 28, 2018 (EP) ..................... 18191082

(51) Int. Cl.
| | | |
|---|---|---|
| *A61K 31/437* | (2006.01) | |
| *A61K 31/4375* | (2006.01) | |
| *A61K 31/55* | (2006.01) | |
| *C07D 471/04* | (2006.01) | |
| *C07D 519/00* | (2006.01) | |

(52) U.S. Cl.
CPC ........ *A61K 31/437* (2013.01); *A61K 31/4375* (2013.01); *A61K 31/55* (2013.01); *C07D 471/04* (2013.01); *C07D 519/00* (2013.01)

(58) Field of Classification Search
CPC .. A61K 31/437; A61K 31/4375; A61K 31/55; C07D 471/04; C07D 519/00
See application file for complete search history.

(56) References Cited

U.S. PATENT DOCUMENTS

| | | |
|---|---|---|
| 10,364,255 B2 | 7/2019 | Bosanac et al. |
| 2015/0250792 A1 | 9/2015 | Muzerelle et al. |
| 2018/0148420 A1 | 5/2018 | Casimiro-Garcia et al. |
| 2018/0354968 A1 | 12/2018 | Bosanac et al. |
| 2019/0263828 A1* | 8/2019 | Bosanac .............. C07D 519/00 |
| 2020/0069663 A1 | 3/2020 | Godbout et al. |
| 2020/0172508 A1 | 6/2020 | Fleck et al. |

FOREIGN PATENT DOCUMENTS

| | | |
|---|---|---|
| WO | 2005035524 A1 | 4/2005 |
| WO | 2014048547 A1 | 4/2014 |
| WO | 2016193844 A1 | 12/2016 |
| WO | 2018011681 A1 | 1/2018 |

OTHER PUBLICATIONS

Barluenga, Jose et al. "Arylation of a-Chiral Ketones by Palladium-Catalyzed Cross-Coupling Reactions of Tosylhydrazones with Aryl Halides**" (2010) Angew. Chem. Int. Ed., 49, 6856-6859.

Berruyer, C. et al. "Vanin-1 −/− Mice Exhibit a Glutathione-Mediated Tissue Resistance to Oxidative Stress" (2004) Molecular and Cellular Biology, vol. 24, No. 16, 7214-7224.

Berruyer, Carole et al. "Vanin-1 licenses inflammatory mediator production by gut epithelial cells and controls colitis by antagonizing peroxisome proliferator-activated receptor γ activity" (2006) The Journal of Experimental Medicine, vol. 203, No. 13, 2817-2827.

Chai, Chi-Young et al. "VNN1 overexpression is associated with poor response to preoperative chemoradiotherapy and adverse prognosis in patients with rectal cancers" (2016) Am J Transl Res, 8(10): 4455-4463.

Gensollen, Thomas et al. "Functional Polymorphisms in the Regulatory Regions of the VNN1 Gene are associated with Susceptibility to Inflammatory Bowel Diseases" (2013) Inflammatory Bowel Diseases, vol. 19, No. 11, 2315-2325.

International Search Report PCT/EP2019/072699 dated Nov. 12, 2019.

Jansen, Patrick A.M. et al. "Expression of the Vanin Gene Family in Normal and Inflamed Human Skin: Induction by Proinflammatory Cytokines" (2009) The Journal of Investigative Dermatology, vol. 129, No. 9, 2167-2174.

Kang, Muxing et al. "VNN1, a potential biomarker for pancreatic cancer-associated new-onset diabetes, aggravates paraneoplastic islet dysfunction by increasing oxidative stress" (2016) Cancer Letters, 373, 241-250.

Kavian, Niloufar et al. "Imbalance of the Vanin-1 Pathway in Systemic Sclerosis" (2016) The Journal of Immunology, vol. 197, 3326-3335.

Khor, Bernard et al. "Genetics and pathogenesis of inflammatory bowel disease" (2011) Nature, vol. 474, 307-317.

Lipinski, Boguslaw "Pathophysiology of oxidative stress in diabetes mellitus" (2001) Journal of Diabetes and its Complications, vol. 15, 203-210.

Martin, Florent et al. "Vanin genes are clustered (human 6q22-24 and mouse 10A2B1) and encode isoforms of pantetheinase ectoenzymes" (2001) Immunogenetics, 53: 296-306.

(Continued)

*Primary Examiner* — Timothy R Rozof
(74) *Attorney, Agent, or Firm* — Atabak R. Royaee

(57) ABSTRACT

The present invention encompasses compounds of the formula I

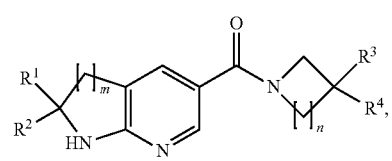

which are suitable for the treatment of diseases related to Vanin, and processes for making these compounds, pharmaceutical preparations containing these compounds, and their methods of use.

55 Claims, No Drawings

(56) References Cited

OTHER PUBLICATIONS

Martin, Florent et al. "Vanin-1 −/− mice show decreased NSAID- and Schistosoma-induced intestinal inflammation assoicated with higher glutathione stores" (2004) The Journal of Clinical Investigation, vol. 113, No. 4, 591-597.

Naquet, Philippe et al. "Role of the Vnn1 pantetheinase in tissue tolerance to stress" (2014) Biochemical Society Transactions, vol. 42, part 4, 1094-1100.

Pouyet, Laurent et al. "Epithelial vanin-1 controls inflammation-driven carcinogenesis in the colitis-associated colon cancer model" (2010) Inflammatory Bowel Diseases, vol. 16, No. 1, 96-104.

Sosa, Venus et al. "Oxidative stress and cancer: An overview" (2013) Ageing Research Reviews, vol. 12, 376-390.

Zhang, Bing et al. "The role of vanin-1 and oxidative stress-related pathways in distinguishing acute and chronic pediatric ITP" (2011) Blood, vol. 117, No. 17, 4569-4579.

Berge, Stephen M. et al. "Journal of Pharmaceutical Salts" Jan. 1977, vol. 66, No. 1, 1-19.

International Search Report PCT/EP2018/065140 dated Jul. 31, 2018.

International Search Report PCT/EP2019/083252 dated Feb. 17, 2020.

* cited by examiner

HETEROAROMATIC COMPOUNDS AS VANIN INHIBITORS

BACKGROUND OF THE INVENTION

1. Technical Field

The present invention relates to novel compounds which inhibit Vanin, pharmaceutical compositions containing the same and their use as medicaments.

2. Background Information

Isoforms 1 and 2 of Vanin enzymes are single-domain extracellular pantetheinases that catalyze the cleavage of pantethine and pantetheine into pantothenic acid and cystamine and cysteamine, respectively (Martin, Immunogenetics, (2001 May-June) Vol. 53, No. 4, pp. 296-306). Generation of cysteamine has been linked to increased oxidative in tissue stress resulting from decreased glutathione levels, a condition characteristic of many pathological conditions, including IBD (Xavier, Nature. 2011 Jun. 15; 474 (7351): 307-17), cancer (Sosa, Ageing research reviews, (2013 January) Vol. 12, No. 1, pp. 376-90) and diabetes (Lipinski, Journal of diabetes and its complications, (2001 July-August) Vol. 15, No. 4, pp. 203-10).

Increased Vanin-1 activity in the gut epithelium has been implicated in promoting tissue damage and inflammation by reducing resistance to oxidative stress in murine models (Naquet, Biochem Soc Trans. 2014 August; 42(4):1094-100); (Berruyer, Molecular and cellular biology, (2004 August) Vol. 24, No. 16, pp. 7214-24); (Berruyer, The Journal of experimental medicine, (2006 Dec. 25) Vol. 203, No. 13, pp. 2817-27); (Pouyet, Inflammatory bowel diseases, (2010 January) Vol. 16, No. 1, pp. 96-104). Homozygous VNN1 knock-out (KO) mice lack appreciable levels of cysteamine in blood and tissues and show glutathione-mediated tissue resistance to oxidative stress (Berruyer, The Journal of experimental medicine, (2006 Dec. 25) Vol. 203, No. 13, pp. 2817-27). In addition, these mice are protected from intestinal injury in TNBS, DSS and Schistosoma-induced colitis models (Berruyer, The Journal of experimental medicine, (2006 Dec. 25) Vol. 203, No. 13, pp. 2817-27; Pouyet, Inflammatory bowel diseases, (2010 January) Vol. 16, No. 1, pp. 96-104; Martin, The Journal of clinical investigation, (2004 February) Vol. 113, No. 4, pp. 591-7). Given rodents lack Vanin-2, their only source of cysteamine is from Vanin-1, therefore the protective phenotype of the VNN1 KO mouse is attributed to the lack of cysteamine.

In humans, Vanin-1 was observed to be upregulated in intestinal epithelium in tissue biopsies from UC and CD patients and a functional polymorphism in the regulatory region of the VNN1 gene which led to increased VNN1 expression was associated with increased IBD susceptibility (P=0.0003 heterozygous vs. wild-type) (Gensollen, Inflammatory bowel diseases, (2013 October) Vol. 19, No. 11, pp. 2315-25).

In addition, upregulation of Vanin-1 activity in the skin and blood has been linked to development and severity of fibrosis in Systemic Sclerosis patients (Kavian, Journal of immunology (Baltimore, Md.: 1950), (20161015) Vol. 197, No. 8, pp. 3326-3335), and elevated levels of Vanin-1 have been observed in chronic Juvenile Idiopathic Thrombocytopenia (Zhang, Blood, (2011 Apr. 28) Vol. 117, No. 17, pp. 4569-79), Psoriasis and Atopic Dermatitis (Jansen, The Journal of investigative dermatology, (2009 September) Vol. 129, No. 9, pp. 2167-74).

Elevated Vanin-1 expression and activity are also present and serve as biomarkers for pancreatic cancer associated new-onset diabetes (Kang, Cancer Letters (New York, N.Y., United States) (2016), 373(2), 241-250) and are also correlated with poor prognosis and response to treatment in colorectal cancer (Chai, American journal of translational research, (2016) Vol. 8, No. 10, pp. 4455-4463).

WO2014048547, WO2018011681 and WO2016193844 disclose Vanin inhibitors for the treatment of a series of diseases e.g. Crohn's disease and ulcerative colitis.

The problem to be solved by the present invention is to provide novel compounds which act as inhibitors of Vanin enzymes, preferably as inhibitors of the Vanin-1 enzyme.

It has been surprisingly found that the compounds of the present invention have potent Vanin-1 inhibitors activity, preferably exhibiting an inhibition of VNN-1 $IC_{50}$ [nM] <100, more preferred $IC_{50}$ [nM]<10, particularly preferred $IC_{50}$ [nM]<1.

Drugs with long residence times in the body are preferred because they remain effective for a longer period of time and therefore can be used in lower doses. Surprisingly the compounds of the present invention indicate favorable mean residence times (MRT).

Moreover the compounds of the present invention exhibit further capacities, which are favorable for their pharmacokinetic and pharmacological profile, e.g. good solubility and good metabolic stability. Furthermore the compounds of the present invention show a good chemical stability.

DETAILED DESCRIPTION OF THE INVENTION

It has surprisingly been found that the problem mentioned above is solved by compounds of formula I of the present invention.

The present invention therefore relates to a compound of formula I

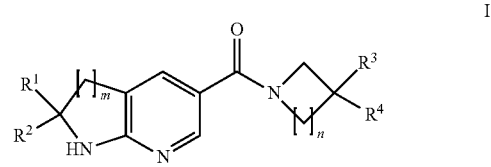

wherein
n denotes 1, 2 or 3;
m denotes 1, 2 or 3;
$R^1$ and $R^2$ are independently from each other selected from the group consisting of H, $C_{1-4}$-alkyl optionally substituted by 1-3 F-atoms or $C_{1-2}$-alkoxy, 6-10 membered aryl substituted by $R^{2.1}$ and 5-6 membered heteroaryl substituted by $R^{2.1}$,
wherein
$R^{2.1}$ is selected from the group consisting of H, F, Cl, Br, —CN, $NR^{2.1.1}R^{2.1.2}$, —$SO_2R^{2.1.3}$ and —$OR^{2.1.4}$,
wherein
$R^{2.1.1}$, $R^{2.1.2}$ independently from each other denote H, $C_{1-4}$-alkyl or $C_{3-4}$-cycloalkyl;
or
$R^{2.1.1}$ and $R^{2.1.2}$ together with the N-atom to which they are attached form a 4-5 membered heterocyclyl or a 6 membered heterocyclyl optionally containing one additional heteroatom selected from the group consisting of N and O;

$R^{2.1.3}$, denotes $C_{1-4}$-alkyl or $NR^{2.1.1}R^{2.1.2}$, $R^{2.1.4}$ is selected from the group consisting of H, $C_{1-4}$-alkyl, $C_{3-5}$-cycoalkyl, 4-5 membered heterocyclyl containing 1 heteroatom selected from the group consisting of N and O.

wherein in the definition of $R^{2.1.1}$, $R^{2.1.2}$, $R^{2.1.3}$ and $R^{2.1.4}$ mentioned alkyl, cycloalkyl and heterocyclyl are optionally substituted by 1-3 F-atoms or one $C_{1-2}$-alkoxy;

or $R^1$ and $R^2$ together may form a 3-5 membered carbocycle or 4-6 membered heterocyclyl containing one heteroatom selected from the group consisting of N and O;

$R^3$ denotes $NR^{3.1}R^{3.2}$;

or $R^3$ denotes a group of formula $R^{3.a}$ or $R^{3.b}$

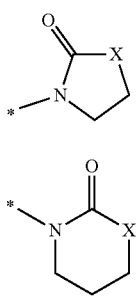

wherein

X denotes $CH_2$, $NR^X$ or O;

wherein $R^X$ denotes H or $C_{1-3}$-alkyl;

$R^{3.1}$ is selected from the group consisting of $C_{1-4}$-alkyl-CO— optionally substituted by 1-3 F-atoms, $C_{3-4}$-cycloalkyl or $C_{1-2}$-alkoxy, $R^{3.1.3}R^{3.1.4}N$—CO—, $R^{3.1.5}O$—CO—, pyrimidine, pyridine, $C_{3-5}$-cycloalkyl-CO— substituted with $R^{3.1.1}$ and $R^{3.1.2}$, 4-6-membered-heterocyclyl-CO— substituted with $R^{3.1.1}$ and $R^{3.1.2}$, —CO-phenyl substituted with $R^{3.1.1}$ and $R^{3.1.2}$;

wherein $R^{3.1.1}$, $R^{3.1.2}$ independently from each other are selected from the group consisting of H, $CH_3$, —$OR^{3.1.1.1}$, F and —CN;

$R^{3.1.3}$, $R^{3.1.4}$ independently from each other denote H, $C_{1-4}$-alkyl or $C_{3-4}$-cycloalkyl;

or $R^{3.1.3}$ and $R^{3.1.4}$ together with the N-atom to which they are attached form a form a 4-5 membered heterocyclyl or a 6 membered heterocyclyl optionally containing one additional heteroatom selected from the group consisting of N and O;

$R^{3.1.5}$ is selected from the group consisting of $C_{1-4}$-alkyl, $C_{3-5}$-cycloalkyl, 4-5 membered heterocyclyl and $C_{3-4}$-cycloalkyl-$CH_2$—;

$R^{3.1.1.1}$ denotes $C_{1-4}$-alkyl, $C_{3-5}$-cycloalkyl or 4-5 membered heterocyclyl;

wherein in the definition of $R^{3.1.1}$, $R^{3.1.2}$, $R^{3.1.3}$, $R^{3.1.4}$, $R^{3.1.5}$ and $R^{3.1.1.1}$ mentioned alkyl, cycloalkyl and heterocyclyl are optionally substituted by 1-3 F-atoms or one $C_{1-2}$-alkoxy;

$R^{3.2}$ is selected from the group consisting of H, $C_{1-4}$-alkyl, $C_{3-4}$-cycloalkyl, $C_{3-4}$-cycloalkyl-$C_{1-2}$-alkyl- and phenyl-$C_{1-2}$-alkyl-;

wherein in the definition of $R^{3.2}$ mentioned alkyl, cycloalkyl and phenyl are optionally substituted by 1-3 F-atoms or one $C_{1-2}$-alkoxy;

$R^4$ denotes hydrogen or $C_{1-4}$-alkyl optionally substituted with 1 to 3 F-atoms;

or $R^3$ and $R^4$ together form a 4-6-membered heterocycle containing one oxygen atom;

or a pharmaceutically acceptable salt thereof.

Preferred Embodiments

In another embodiment of the present invention m denotes 1 or 2.

In another embodiment of the present invention m denotes 1.

In another embodiment of the present invention m denotes 2.

In another embodiment of the present invention m denotes 3.

In another embodiment of the present invention n denotes 1 or 2

In another embodiment of the present invention n denotes 1.

In another embodiment of the present invention n denotes 2.

In another embodiment of the present invention $R^1$ denotes H or methyl.

In another embodiment of the present invention $R^1$ denotes H.

In another embodiment of the present invention $R^1$ denotes methyl.

In another embodiment of the present invention $R^2$ denotes methyl, ethyl, pyrimidine or phenyl substituted by $R^{2.1}$, wherein $R^{2.1}$ is selected from the group consisting of H, F, Cl and —CN.

In another embodiment of the present invention $R^2$ denotes methyl or phenyl substituted by $R^{2.1}$.

In another embodiment of the present invention $R^2$ denotes methyl, ethyl, pyrimidine or phenyl.

In another embodiment of the present invention $R^2$ denotes methyl or ethyl.

In another embodiment of the present invention $R^2$ denotes methyl.

In another embodiment of the present invention $R^2$ denotes ethyl.

In another embodiment of the present invention $R^2$ denotes pyrimidine.

In another embodiment of the present invention $R^2$ denotes phenyl substituted by $R^{2.1}$.

In another embodiment of the present invention $R^{2.1}$ denotes H, F, Cl or CN.

In another embodiment of the present invention $R^{2.1}$ denotes H.

In another embodiment of the present invention $R^{2.1}$ denotes F.

In another embodiment of the present invention $R^{2.1}$ denotes Cl.

In another embodiment of the present invention $R^{2.1}$ denotes CN.

In another embodiment of the present invention $R^3$ denotes $NR^{3.1}R^{3.2}$, or $R^3$ denotes a group of formula $R^{3.a}$

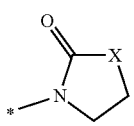

wherein
X denotes CH$_2$ or O;
R$^{3.1}$ denotes —COCH$_3$, pyrimidine, C$_{3-4}$-cycloalkyl-CO— substituted with R$^{3.1.1}$ and R$^{3.1.2}$
wherein
R$^{3.1.1}$, R$^{3.1.2}$ independently from each other denote H, CH$_3$, F or —CN;
R$^{3.2}$ denotes CH$_3$, In another embodiment of the present invention R$^3$ denotes NR$^{3.1}$R$^{3.2}$.

In another embodiment of the present invention R$^3$ denotes a group of formula R$^{3.a}$.

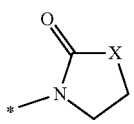

In another embodiment of the present invention R$^3$ denotes a group of formula R$^{3.b}$.

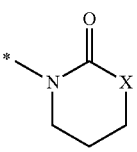

In another embodiment of the present invention X denotes CH$_2$.

In another embodiment of the present invention X denotes O.

In another embodiment of the present invention X denotes NR$^X$.

In another embodiment of the present invention R$^X$ denotes H or C$_{1-3}$-alkyl.

In another embodiment of the present invention R$^X$ denotes H.

In another embodiment of the present invention R$^X$ denotes C$_{1-3}$-alkyl, preferably methyl.

In another embodiment of the present invention R$^{3.1}$ denotes —COCH$_3$, pyrimidine, C$_{3-4}$-cycloalkyl-CO— substituted with R$^{3.1.1}$ and R$^{3.1.2}$
wherein R$^{3.1.1}$, R$^{3.1.2}$ independently from each other denote H, —CH$_3$, F or —CN.

In another embodiment of the present invention R$^{3.1}$ denotes —CO—C$_{1-4}$-alkyl.

In another embodiment of the present invention R$^{3.1}$ denotes —COCH$_3$.

In another embodiment of the present invention R$^{3.1}$ denotes pyrimidine.

In another embodiment of the present invention R$^{3.1}$ denotes C$_{3-4}$-cycloalkyl-CO—.

In another embodiment of the present invention R$^{3.1}$ denotes cyclopropyl-CO— substituted with R$^{3.1.1}$ and R$^{3.1.2}$.

In another embodiment of the present invention R$^{3.1}$ denotes cyclobutyl-CO— substituted with R$^{3.1.1}$ and R$^{3.1.2}$.

In another embodiment of the present invention R$^{3.1.1}$, R$^{3.1.2}$ independently from each other denote H, CH$_3$, F or —CN.

In another embodiment of the present invention R$^{3.1.1}$ denotes H.

In another embodiment of the present invention R$^{3.1.2}$ denotes H.

In another embodiment of the present invention R$^{3.1.1}$ and R$^{3.1.2}$ denote H.

In another embodiment of the present invention R$^{3.2}$ denotes CH$_3$.

In another embodiment of the present invention R$^4$ denotes hydrogen.

In another embodiment of the present invention R$^3$ and R$^4$ together form a 6-membered heterocycle containing one oxygen atom.

A preferred embodiment of the current invention is a compound of the formula I

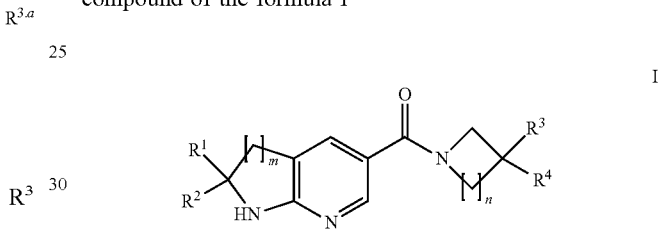

wherein
n denotes 1 or 2;
m denotes 1, 2 or 3;
R$^1$ denotes H or methyl
R$^2$ denotes methyl, ethyl, pyrimidine or phenyl substituted by R$^{2.1}$,
wherein
R$^{2.1}$ is selected from the group consisting of H, F, Cl and —CN;
R$^3$ denotes NR$^{3.1}$R$^{3.2}$,
or
R$^3$ denotes a group of formula R$^{3a}$,

wherein
X denotes CH$_2$ or O;
R$^{3.1}$ denotes —COCH$_3$, pyrimidine or C$_{3-4}$-cycloalkyl-CO— substituted with R$^{3.1.1}$ and R$^{3.1.2}$
wherein
R$^{3.1.1}$, R$^{3.1.2}$ independently from each other denote H, CH$_3$, F or —CN;
R$^{3.2}$ denotes CH$_3$;
R$^4$ denotes hydrogen;
or
R$^3$ and R$^4$ together form a 6-membered heterocycle containing one oxygen atom;
or a pharmaceutically acceptable salt thereof.

A preferred embodiment of the current invention is a compound of the formula I

I wherein
n denotes 1 or 2;
m denotes 1;
$R^1$ denotes methyl
$R^2$ denotes methyl or phenyl substituted by $R^{2.1}$,
  wherein
    $R^{2.1}$ is selected from the group consisting of H, F, Cl and —CN;
$R^3$ denotes $NR^{3.1}R^{3.2}$,
or
$R^3$ denotes a group of formula $R^{3.a}$, $R^{3.a}$ wherein
X denotes $CH_2$ or O;
$R^{3.1}$ denotes —$COCH_3$, pyrimidine, $C_{3-4}$-cycloalkyl-CO— substituted with $R^{3.1.1}$ and $R^{3.1.2}$,
  wherein
    $R^{3.1.1}$, $R^{3.1.2}$ independently from each other denote H, $CH_3$, F or —CN
$R^{3.2}$ denotes $CH_3$;
$R^4$ denotes hydrogen;
or
$R^3$ and $R^4$ together form a 6-membered heterocycle containing one oxygen atom;
or a pharmaceutically acceptable salt thereof.

A preferred embodiment of the current invention is a compound of the formula I

I wherein
n denotes 1 or 2;
m denotes 2;
$R^1$ denotes H or methyl;
$R^2$ denotes methyl, ethyl, pyrimidin or phenyl;
$R^3$ denotes $NR^{3.1}R^{3.2}$;
or
$R^3$ denotes a group of formula $R^{3.a}$ $R^{3.a}$ wherein
X denotes $CH_2$ or O
$R^{3.1}$ denotes —$COCH_3$, pyrimidine or $C_{3-4}$-cycloalkyl-CO— substituted with $R^{3.1.1}$ and $R^{3.1.2}$,
  wherein
    $R^{3.1.1}$, $R^{3.1.2}$ independently from each other denote H, $CH_3$, F or —CN;
$R^{3.2}$ denotes $CH_3$;
$R^4$ denotes hydrogen
or
$R^3$ and $R^4$ together form a 6-membered heterocycle containing one oxygen atom or a pharmaceutically acceptable salt thereof.

A further preferred embodiment of the current invention are the above compounds of formula I, selected from the group consisting of examples 6, 9.1, 8.2, 5.3, 2.1, 7.2, 13.3, 5.2, 13.1, 4.1, 11.10, 4.4, 11.9, 7.4, 4.3, 7.1, 8.3, 11.6, 10 and 9.3.

Ex. 6

Ex. 9.1

Ex. 8.2

Ex. 5.3

-continued
Ex. 2.1.
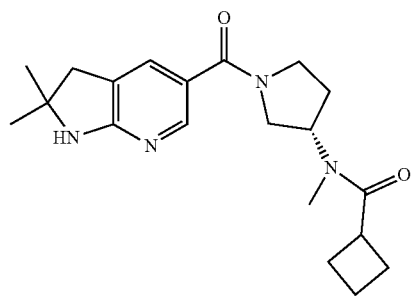
Ex 7.2
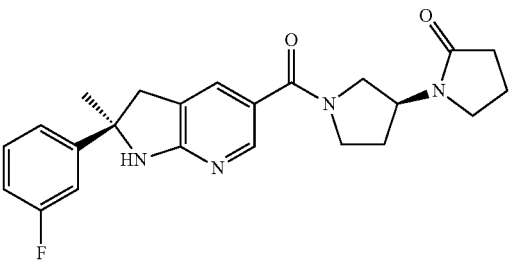
Ex. 13.3
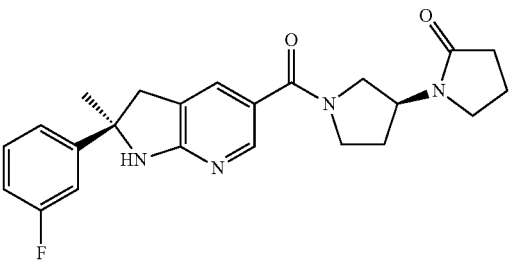
Ex. 5.2
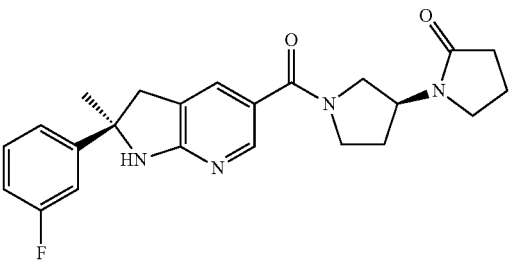
Ex. 13.1
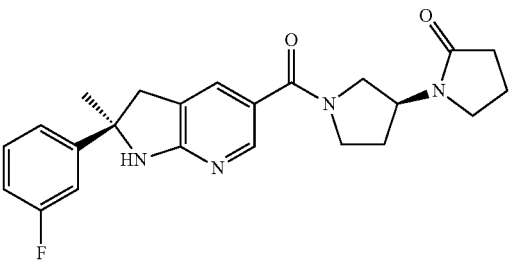
Ex. 4.1
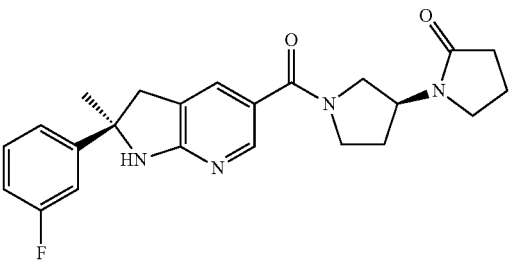
-continued
Ex. 11.10
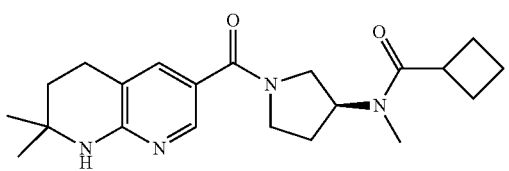
Ex. 4.4
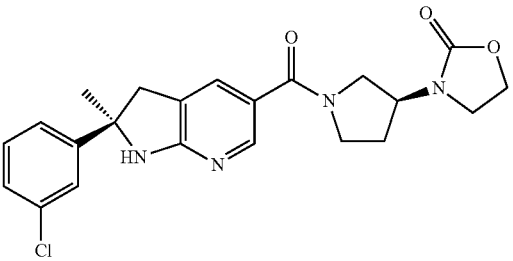
Ex. 11.9
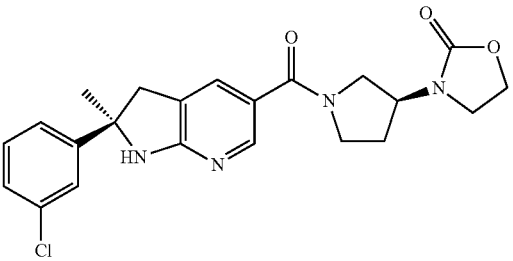
Ex. 7.4
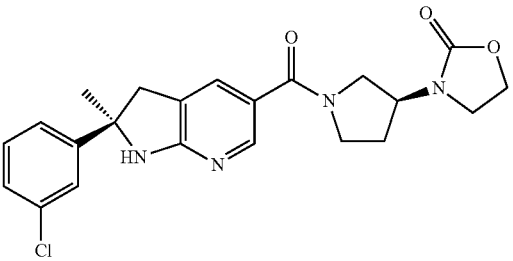
Ex. 4.3
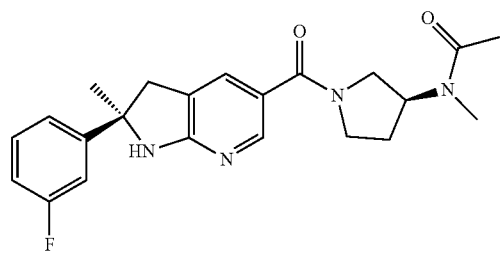
Ex. 7.1
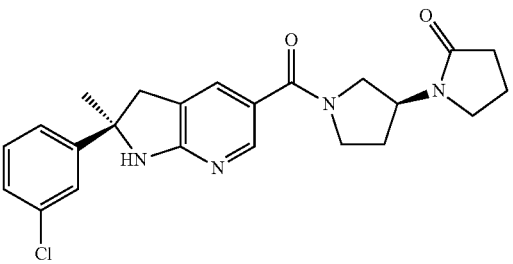

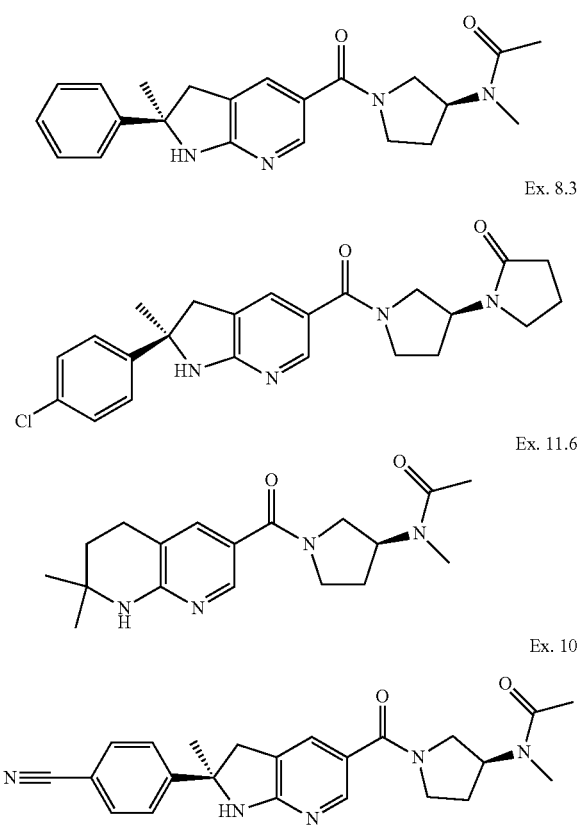

or a pharmaceutically acceptable salt thereof.

A further preferred embodiment of the current invention are the above compounds of formula I, selected from the group consisting of examples 6, 9.1, 8.2, 5.3, 2.1, 7.2, 5.2, 4.1, 4.4, 7.4, 4.3, 7.1, 8.3, 10 and 9.3.

A further preferred embodiment of the current invention are the above compounds of formula I, selected from the group consisting of examples 13.1, 13.3, 11.10, 11.9 and 11.6.

A further preferred embodiment of the current invention is the compound of example 6.

A further preferred embodiment of the current invention is the compound of example 9.1

A further preferred embodiment of the current invention is the compound of example 8.2.

A further preferred embodiment of the current invention is the compound of example 5.3.

A further preferred embodiment of the current invention is the compound of example 2.1.

A further preferred embodiment of the current invention is the compound of example 7.2.

A further preferred embodiment of the current invention is the compound of example 13.3.

A further preferred embodiment of the current invention is the compound of example 5.2.

A further preferred embodiment of the current invention is the compound of example 13.1.

A further preferred embodiment of the current invention is the compound of example 4.1.

A further preferred embodiment of the current invention is the compound of example 11.10.

A further preferred embodiment of the current invention is the compound of example 4.4.

A further preferred embodiment of the current invention is the compound of example 11.9.

A further preferred embodiment of the current invention is the compound of example 7.4.

A further preferred embodiment of the current invention is the compound of example 4.3.

A further preferred embodiment of the current invention is the compound of example 7.1.

A further preferred embodiment of the current invention is the compound of example 8.3.

A further preferred embodiment of the current invention is the compound of example 11.6.

A further preferred embodiment of the current invention is the compound of example 10.

A further preferred embodiment of the current invention is the compound of example 9.3.

A further preferred embodiment of the current invention are pharmaceutically acceptable salts of the above compounds of formula I, selected from the group consisting of examples 6, 9.1, 8.2, 5.3, 2.1, 7.2, 13.3, 5.2, 13.1, 4.1, 11.10, 4.4, 11.9, 7.4, 4.3, 7.1, 8.3, 11.6, 10 and 9.3.

A further preferred embodiment of the current invention are pharmaceutically acceptable salts of the above compounds of formula I, selected from the group consisting of examples 6, 9.1, 8.2, 5.3, 2.1, 7.2, 5.2, 4.1, 4.4, 7.4, 4.3, 7.1, 8.3, 10 and 9.3.

A further preferred embodiment of the current invention are pharmaceutically acceptable salts of the above compounds of formula I, selected from the group consisting of examples 13.1, 13.3, 11.10, 11.9 and 11.6.

A further preferred embodiment of the current invention are pharmaceutically acceptable salts of the compound of example 6.

A further preferred embodiment of the current invention are pharmaceutically acceptable salts of the compound of example 9.1

A further preferred embodiment of the current invention are pharmaceutically acceptable salts of the compound of example 8.2.

A further preferred embodiment of the current invention are pharmaceutically acceptable salts of the compound of example 5.3.

A further preferred embodiment of the current invention are pharmaceutically acceptable salts of the compound of example 2.1.

A further preferred embodiment of the current invention are pharmaceutically acceptable salts of the compound of example 7.2.

A further preferred embodiment of the current invention are pharmaceutically acceptable salts of the compound of example 13.3.

A further preferred embodiment of the current invention are pharmaceutically acceptable salts of the compound of example 5.2.

A further preferred embodiment of the current invention are pharmaceutically acceptable salts of the compound of example 13.1.

A further preferred embodiment of the current invention are pharmaceutically acceptable salts of the compound of example 4.1.

A further preferred embodiment of the current invention are pharmaceutically acceptable salts of the compound of example 11.10.

A further preferred embodiment of the current invention are pharmaceutically acceptable salts of the compound of example 4.4.

A further preferred embodiment of the current invention are pharmaceutically acceptable salts of the compound of example 11.9.

A further preferred embodiment of the current invention are pharmaceutically acceptable salts of the compound of example 7.4.

A further preferred embodiment of the current invention are pharmaceutically acceptable salts of the compound of example 4.3.

A further preferred embodiment of the current invention are pharmaceutically acceptable salts of the compound of example 7.1.

A further preferred embodiment of the current invention are pharmaceutically acceptable salts of the compound of example 8.3.

A further preferred embodiment of the current invention are pharmaceutically acceptable salts of the compound of example 11.6.

A further preferred embodiment of the current invention are pharmaceutically acceptable salts of the compound of example 10.

A further preferred embodiment of the current invention are pharmaceutically acceptable salts of the compound of example 9.3.

A further preferred embodiment of the current invention are compounds of formula I, selected from the group consisting of the examples listed in Table A or pharmaceutically acceptable salts thereof.

TABLE A

Racemates

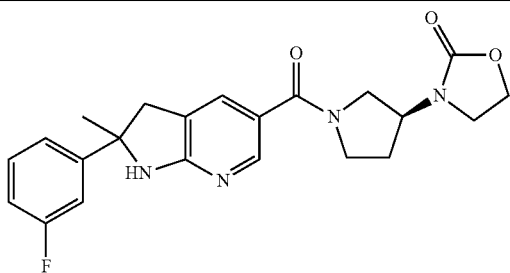

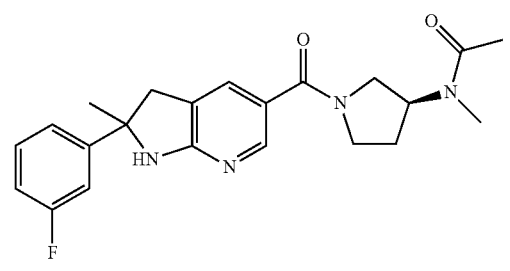 [SMILES: CC(=O)N(C)[C@H]1CCN(C(=O)c2cnc3c(c2)CC(C)(c2cccc(F)c2)N3)C1]

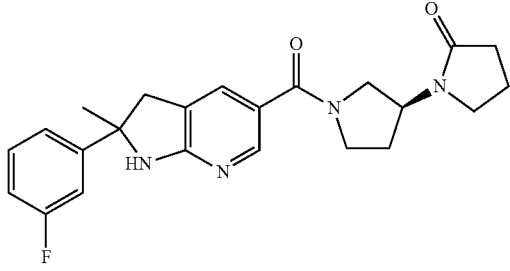 [SMILES: CC1(c2cccc(F)c2)Cc2cc(C(=O)N3CC[C@H](N4CCCC4=O)C3)cnc2N1]

TABLE A-continued

Racemates

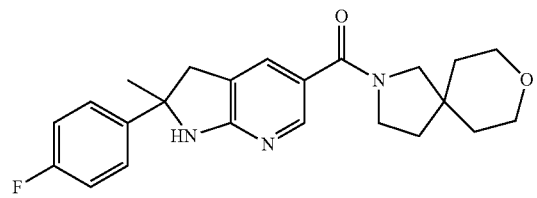 [SMILES: CC1(c2ccc(F)cc2)Cc2cc(C(=O)N3CCC4(CCOCC4)C3)cnc2N1]

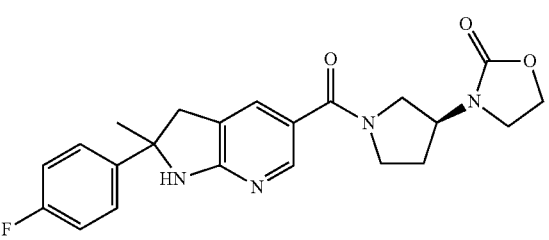 [SMILES: CC1(c2ccc(F)cc2)Cc2cc(C(=O)N3CC[C@H](N4CCOC4=O)C3)cnc2N1]

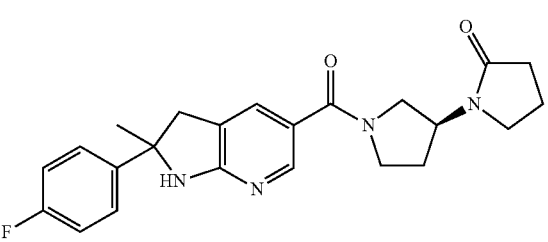 [SMILES: CC1(c2ccc(F)cc2)Cc2cc(C(=O)N3CC[C@H](N4CCCC4=O)C3)cnc2N1]

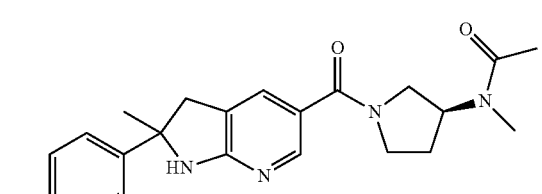

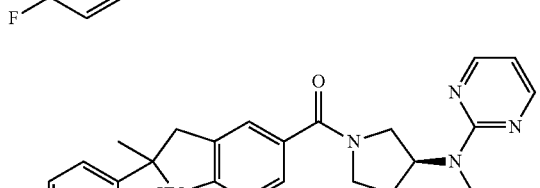

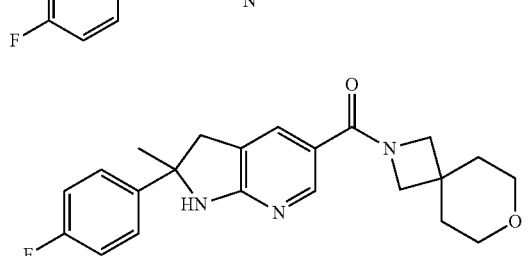

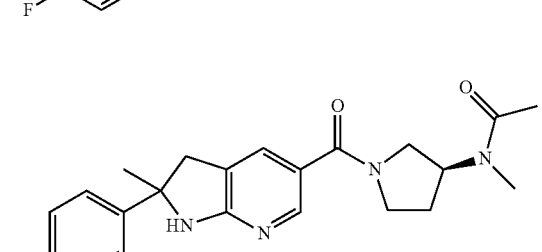

TABLE A-continued

Racemates

[Chemical structures of racemate compounds]

A further preferred embodiment of the current invention are compounds of formula I, selected from the group consisting of the examples listed in Table B or pharmaceutically acceptable salts thereof.

TABLE B

[Chemical structures of Table B compounds]

TABLE B-continued

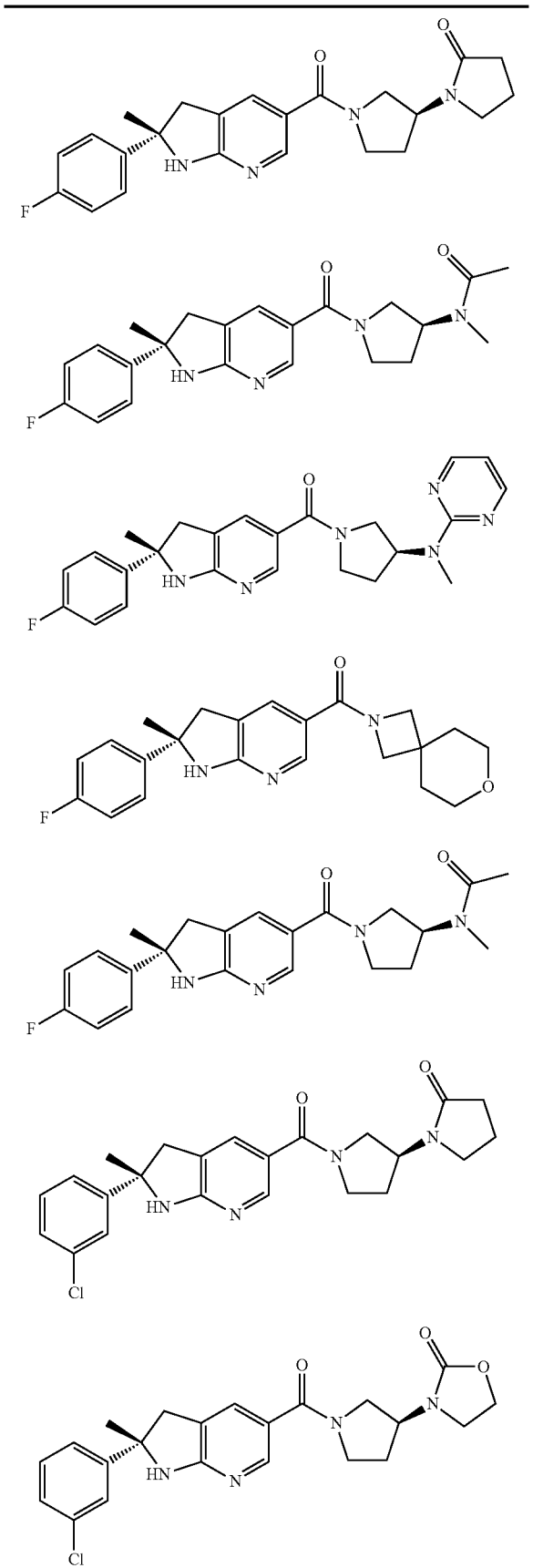

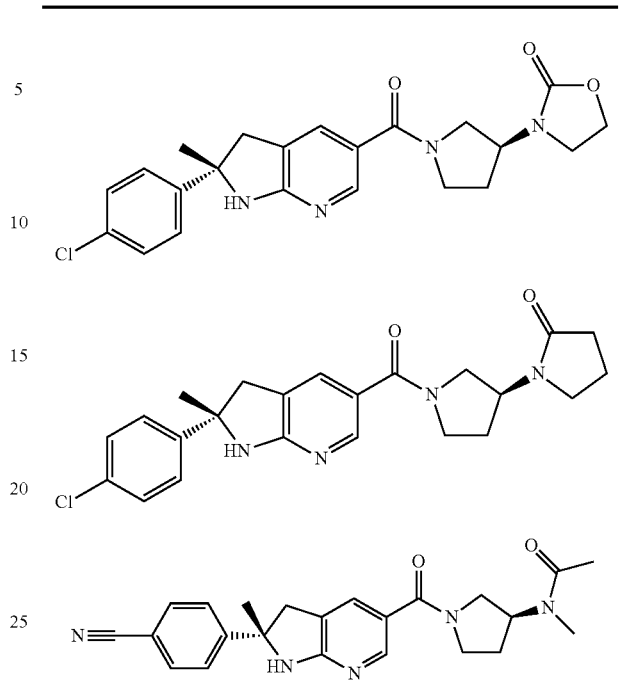

Another embodiment of the present invention are compounds of formula IA or the pharmaceutically acceptable salts thereof.

IA

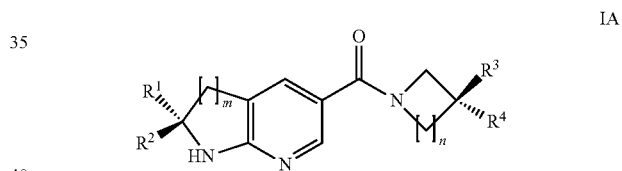

Another embodiment of the present invention are compounds of formula IB or the pharmaceutically acceptable salts thereof.

IB

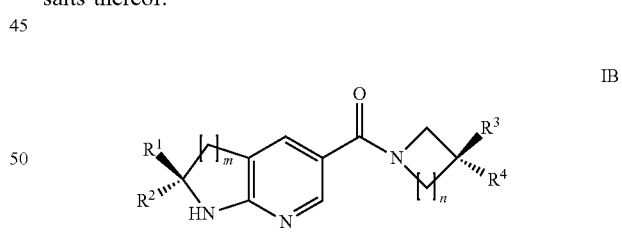

Another embodiment of the present invention are compounds of formula IC or the pharmaceutically acceptable salts thereof.

IC

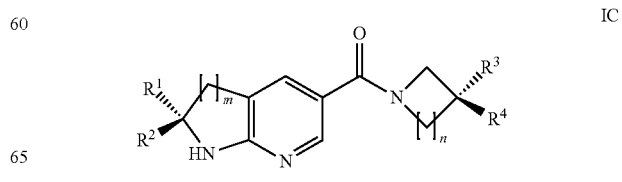

Another embodiment of the present invention are compounds of formula ID or the pharmaceutically acceptable salts thereof.

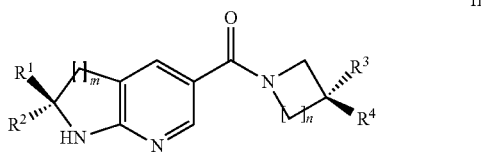

Any and each of the definitions of $R^1$, $R^2$, $R^3$, $E^4$, $R^{2.1}$, $R^{2.1.1}$, $R^{2.1.2}$, $R^{2.1.3}$, $R^{2.1.4}$, $R^{3.1}$, $R^{3.1.1}$, $R^{3.1.2}$, $R^{3.1.3}$, $R^{3.1.4}$, $R^{3.1.5}$, $R^{3.1.1.1}$, $R^{3.2}$, $R^X$, m, n and X may be combined with each other.

A further embodiment of the current invention is a pharmaceutical composition comprising a therapeutically effective amount of at least one compound of formula I or a pharmaceutically acceptable salt thereof and one or more pharmaceutically acceptable excipients.

A further embodiment of the current invention is a compound of formula I or a pharmaceutically acceptable salt thereof for use as a medicament.

Furthermore, the present invention relates to the use of a compound of general formula I for the treatment and/or prevention of a disease and/or condition associated with or modulated by Vanin-1 or Vanin-2, especially Vanin-1, including but not limited to the treatment and/or prevention of inflammatory diseases, preferably inflammatory bowel diseases.

A further embodiment of the current invention is the use of a compound of formula I for treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes.

A further embodiment of the current invention is the use of a compound of formula I for treating a patient suffering from Crohn's disease, ulcerative colitis, systemic sclerosis, Non-Alcoholic Steatohepathitis (NASH), chronic obstructive pulmonary disease or atopic dermatitis, preferably Crohn's disease, ulcerative colitis, systemic sclerosis, Non-Alcoholic Steatohepathitis (NASH) or atopic dermatitis, particularly preferred from Crohn's disease or ulcerative colitis.

A further embodiment of the current invention is the use of a compound of formula I for treating a patient suffering from moderate to severe Crohn's disease.

A further embodiment of the current invention is the use of a compound of formula I for treating a patient suffering from ulcerative colitis.

A further embodiment of the current invention is the use of a compound of formula I for treating a patient suffering from atopic dermatitis.

A further embodiment of the current invention is the use of a compound of formula I for treating a patient suffering from NASH.

In a further embodiment, there is provided a method of treating a disease chosen from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes comprising administering to a patient a therapeutically effective amount of a compound according to the first embodiment or any of its related embodiments or a pharmaceutically acceptable salt thereof.

In a further embodiment, there is provided a process for preparation of a compound according to the first embodiment or any of its related embodiments by the methods shown herein below.

In a further aspect the present invention relates to a compound of general formula 1 for use in the treatment and/or prevention of above mentioned diseases and conditions.

In a further aspect the present invention relates to the use of a compound of general formula 1 for the preparation of a medicament for the treatment and/or prevention of above mentioned diseases and conditions.

In a further aspect the present invention relates to methods for the treatment or prevention of above mentioned diseases and conditions, which method comprises the administration of an effective amount of a compound of general formula 1 to a human being.

The actual pharmaceutically effective amount or therapeutic dosage will usually depend on factors known by those skilled in the art such as age and weight of the patient, route of administration and severity of disease. In any case the compounds will be administered at dosages and in a manner which allows a pharmaceutically effective amount to be delivered based upon patient's unique condition.

A further embodiment of the current invention is a pharmaceutical composition comprising additionally to a compound of formula I, a pharmaceutically active compound selected from the group consisting of an immunomodulatory agent, anti-inflammatory agent, or a chemotherapeutic agent. Examples of such agents include but are not limited to cyclophosphamide, mycophenolate (MMF), hydroxychloroquine, glucocorticoids, corticosteroids, immunosuppressants, NSAIDs, non-specific and COX-2 specific cyclooxygenase enzyme inhibitors, tumour necrosis factor receptor (TNF) receptors antagonists, IL12/23 and IL23 antagonists, α4β7 integrin blocking antibodies, non-selective and selective JAK kinase inhibitors and methotrexate, but also combinations of two or three active substances.

Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

In the groups, radicals, or moieties defined below, the number of carbon atoms is often specified preceding the group, for example, $C_{1-6}$-alkyl means an alkyl group or radical having 1 to 6 carbon atoms. In general in groups like HO, $H_2N$, (O)S, $(O)_2S$, CN (cyano), HOOC, $F_3C$ or the like, the skilled artisan can see the radical attachment point(s) to the molecule from the free valences of the group itself. For combined groups comprising two or more subgroups, the last named subgroup is the radical attachment point, for example, the substituent "aryl-$C_{1-3}$-alkyl" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

The numeration of the atoms of a substituent starts with the atom which is closest to the core or to the group to which the substituent is attached.

For example, the term "3-carboxypropyl-group" represents the following substituent:

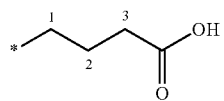

wherein the carboxy group is attached to the third carbon atom of the propyl group. The terms "1-methylpropyl-", "2,2-dimethylpropyl-" or "cyclopropylmethyl-" group represent the following groups:

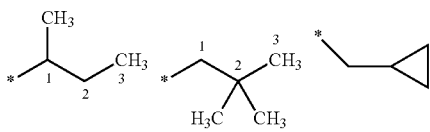

The asterisk may be used in sub-formulas to indicate the bond which is connected to the core molecule as defined.

The term "substituted" as used herein, means that any one or more hydrogens on the designated atom is replaced with a selection from the indicated group, provided that the designated atom's normal valence is not exceeded, and that the substitution results in a stable compound. Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

In general, substantially pure stereoisomers can be obtained according to synthetic principles known to a person skilled in the field, e.g. by separation of corresponding mixtures, by using stereochemically pure starting materials and/or by stereoselective synthesis. It is known in the art how to prepare optically active forms, such as by resolution of racemic forms or by synthesis, e.g. starting from optically active starting materials and/or by using chiral reagents. Enantiomerically pure compounds of this invention or intermediates may be prepared via asymmetric synthesis, for example by preparation and subsequent separation of appropriate diastereomeric compounds or intermediates which can be separated by known methods (e.g. by chromatographic separation or crystallization) and/or by using chiral reagents, such as chiral starting materials, chiral catalysts or chiral auxiliaries.

Further, it is known to the person skilled in the art how to prepare enantiomerically pure compounds from the corresponding racemic mixtures, such as by chromatographic separation of the corresponding racemic mixtures on chiral stationary phases; or by resolution of a racemic mixture using an appropriate resolving agent, e.g. by means of diastereomeric salt formation of the racemic compound with optically active acids or bases, subsequent resolution of the salts and release of the desired compound from the salt; or by derivatization of the corresponding racemic compounds with optically active chiral auxiliary reagents, subsequent diastereomer separation and removal of the chiral auxiliary group; or by kinetic resolution of a racemate (e.g. by enzymatic resolution); by enantioselective crystallization from a conglomerate of enantiomorphous crystals under suitable conditions; or by (fractional) crystallization from a suitable solvent in the presence of an optically active chiral auxiliary.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

Further pharmaceutically acceptable salts can be formed with cations from ammonia, L-arginine, calcium, 2,2'-iminobisethanol, L-lysine, magnesium, N-methyl-D-glucamine, potassium, sodium and tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer selected from 2, 3, 4, 5 or 6, preferably 4 or 6, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH$ ($CH_3$)—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—

CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "C$_{3-n}$-cycloalkyl", wherein n is an integer from 4 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

The term "carbocyclyl" or "carbocycle" as used either alone or in combination with another radical, means a mono- bi- or tricyclic ring structure consisting of 3 to 14 carbon atoms. The term "carbocyclyl" or "carbocycle" refers to fully saturated and aromatic ring systems and partially saturated ring systems. The term "carbocyclyl" or "carbocycle" encompasses fused, bridged and spirocyclic systems.

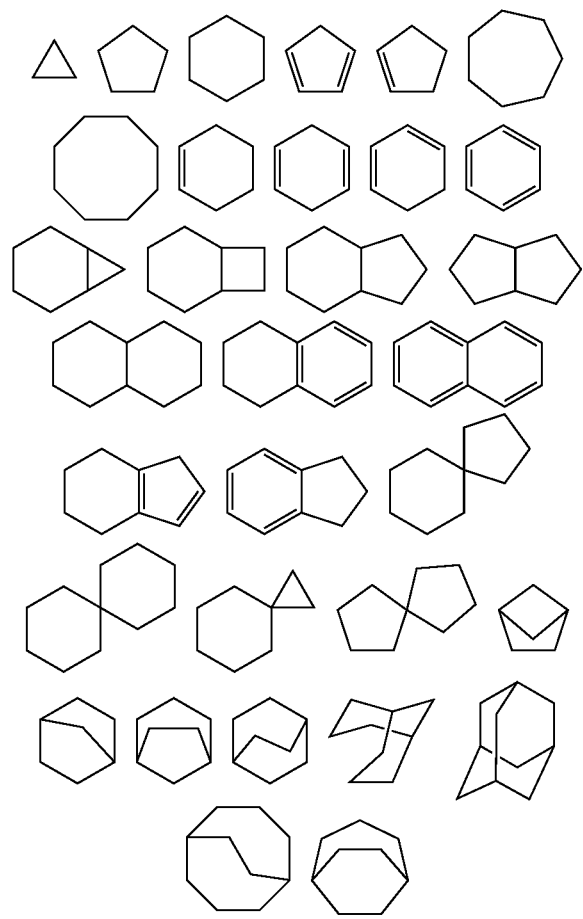

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heterocyclyl" or "heterocycle" means a saturated or unsaturated mono- or polycyclic-ring systems including aromatic ring system containing one or more heteroatoms selected from N, O or S(O)$_r$, wherein r=0, 1 or 2, consisting of 3 to 14 ring atoms wherein none of the heteroatoms is part of the aromatic ring. The term "heterocyclyl" or "heterocycle" is intended to include all the possible isomeric forms.

Thus, the term "heterocyclyl" or "heterocycle" includes the following exemplary structures which are not depicted as radicals as each form are optionally attached through a covalent bond to any atom so long as appropriate valences are maintained:

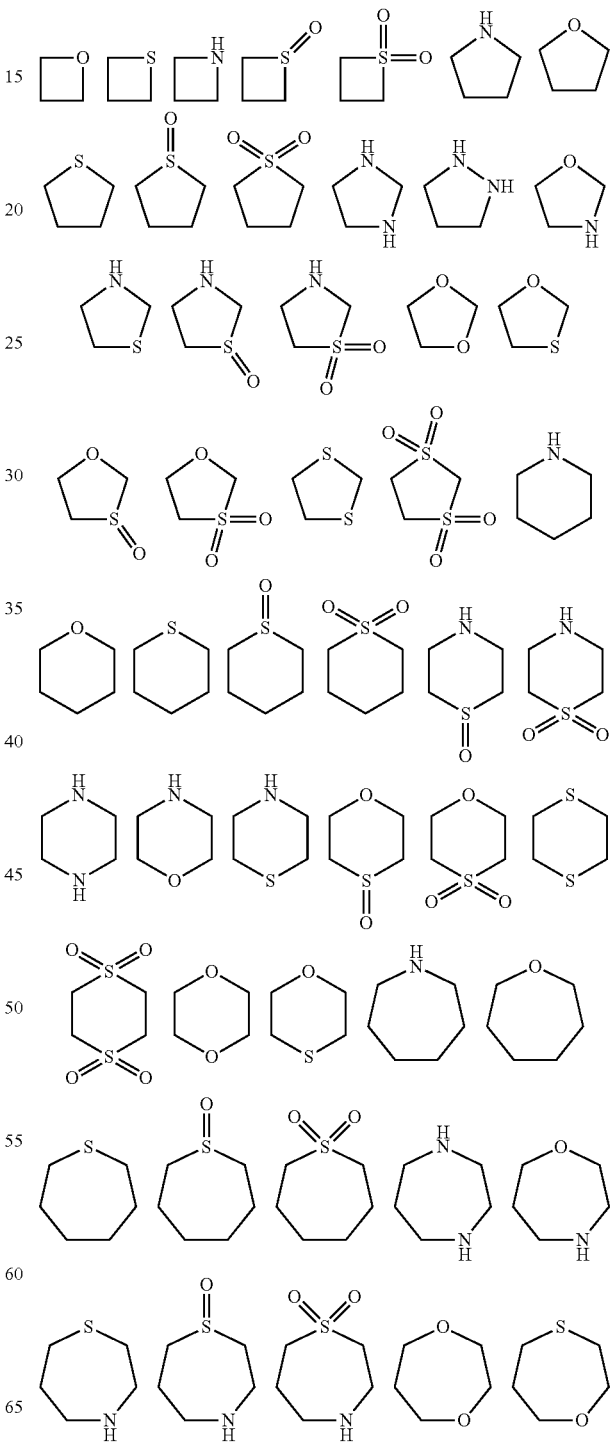

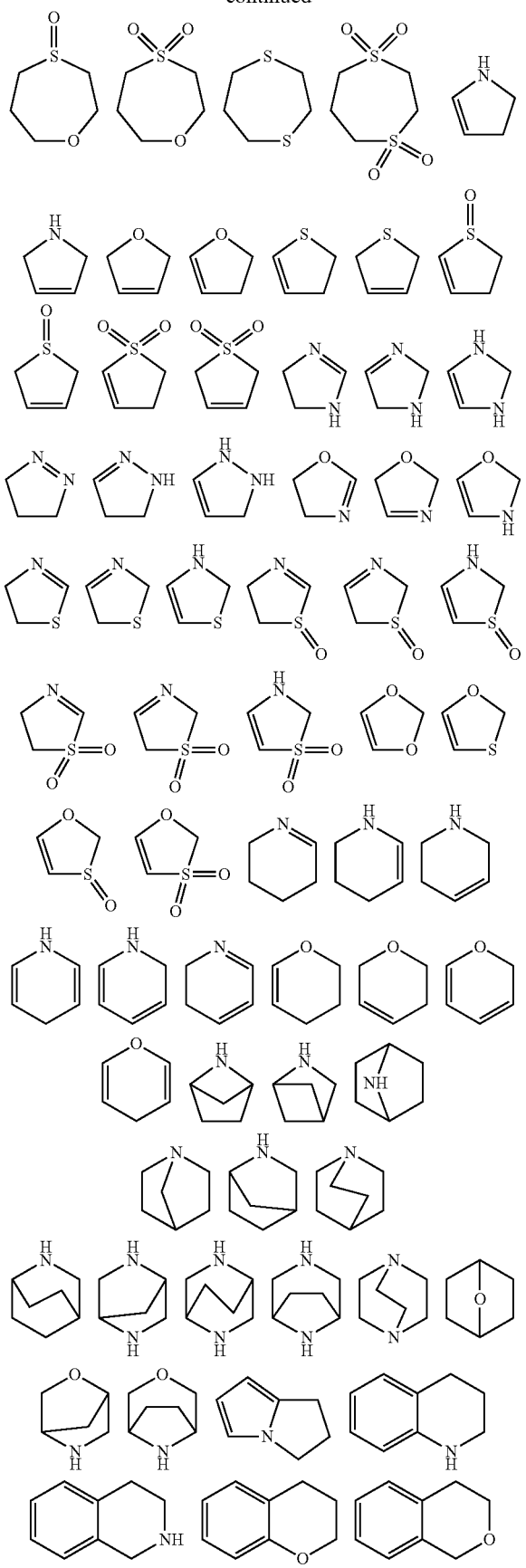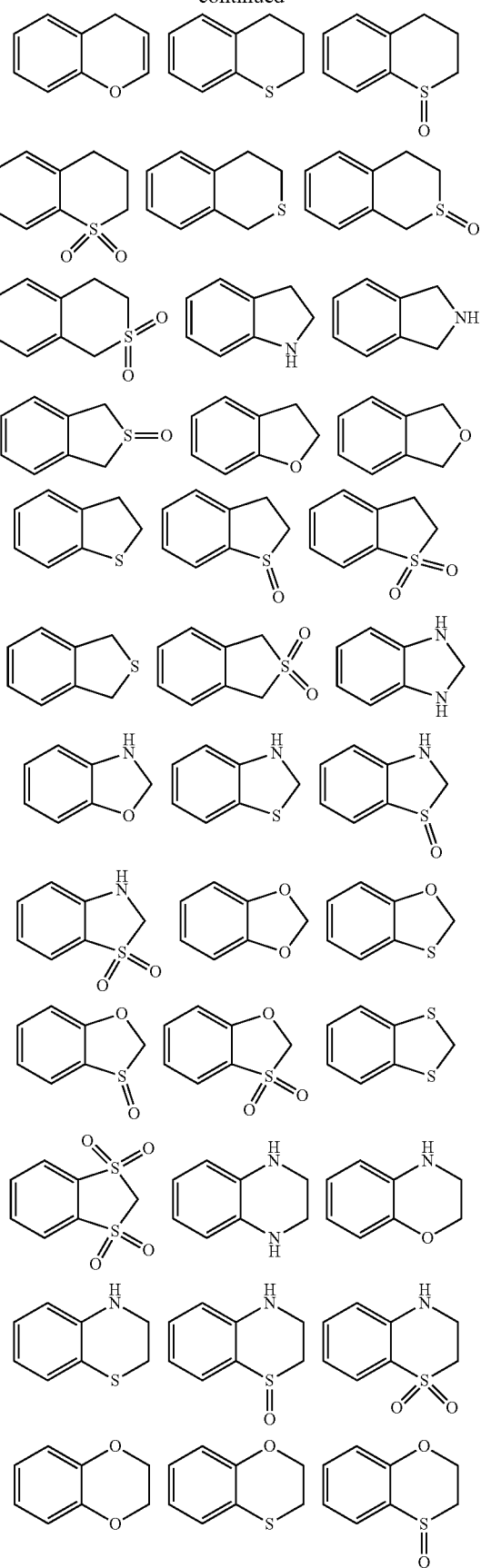

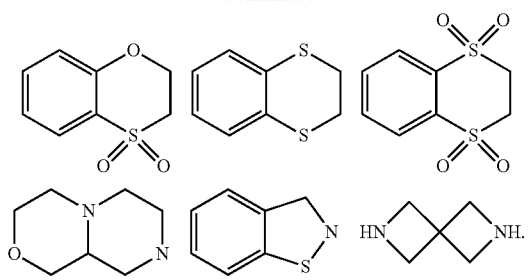

The term "heteroaryl" means a mono- or polycyclic-ring systems containing one or more heteroatoms selected from N, O or S(O)$_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form are optionally attached through a covalent bond to any atom so long as appropriate valences are maintained:

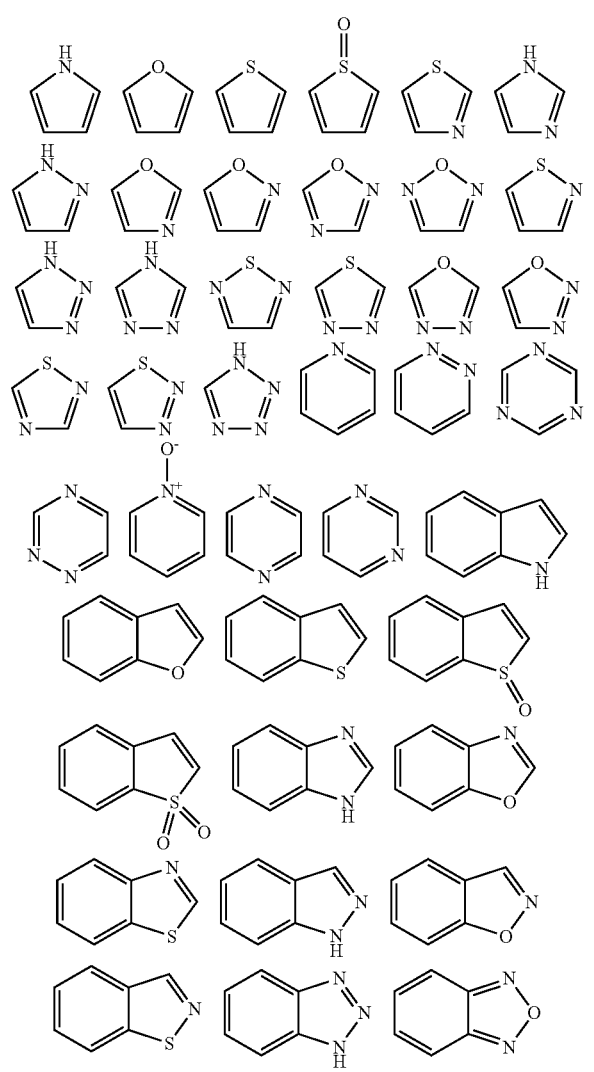

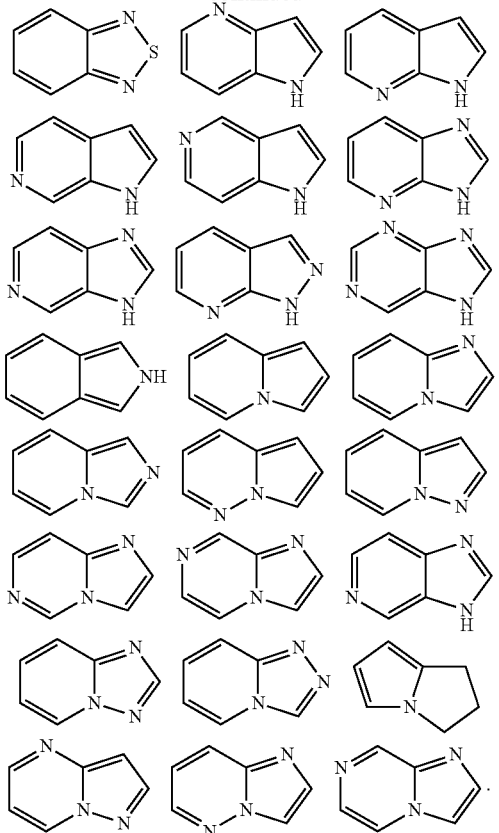

Many of the terms given above may be used repeatedly in the definition of a formula or group and in each case have one of the meanings given above, independently of one another.

Suitable preparations for administering the compounds of formula 1 will be apparent to those with ordinary skill in the art and include for example tablets, pills, capsules, suppositories, lozenges, troches, solutions, syrups, elixirs, sachets, injectables, inhalatives and powders etc., preferably tablets.

Suitable tablets may be obtained, for example, by mixing one or more compounds according to formula I with known excipients, for example inert diluents, carriers, disintegrants, adjuvants, surfactants, binders and/or lubricants.

By a therapeutically effective amount for the purposes of this invention is meant a quantity of substance that is capable of obviating symptoms of illness or alleviating these symptoms, or which prolong the survival of a treated patient.

| List of Abbreviations | |
|---|---|
| Ac | Acetyl |
| ACN | Acetonitrile |
| aq | Aqueous |
| Bn | Benzyl |
| Bu | Butyl |
| Boc | tert-butyloxycarbonyl |
| ° C. | degree celsius |
| cat | Catalyst |
| CD | Crohn's disease |
| conc | concentrated |
| CyH | cyclohexane |
| d | day(s) |
| DBU | 1,8-Diazabicyclo(5.4.0)undec-7-ene |
| DCM | Dichloromethane |

List of Abbreviations

| Abbreviation | Meaning |
|---|---|
| DMAP | 4-N,N-dimethylaminopyridine |
| DMA | Dimethylacetamide |
| DME | 1,2-dimethoxyethane |
| DMF | N,N-dimethylformamide |
| DMSO | Dimethylsulfoxide |
| DIPE | diisopropyl ether |
| DIPEA | N,N-diisopropylethylamine |
| dppf | 1,1'-bis(diphenylphosphino)ferrocene |
| EDC | 1-Ethyl-3-(3-dimethylaminopropyl)carbodiimide |
| ESI | electron spray ionization |
| ESI-MS | electrospray ionisation mass spectrometry |
| Et | Ethyl |
| $Et_2O$ | diethyl ether |
| EtOAc | ethyl acetate |
| EtOH | Ethanol |
| Ex. | example |
| h | hour(s) |
| HATU | N,N,N',N'-tetramethyl-O-(7-azabenzotriazol-1-yl)uranium hexafluorophosphate |
| HPLC | high performance liquid chromatography |
| HWB assay | Human Whole Blood assay |
| i | Iso |
| IBD | Inflammatory Bowel Disease |
| In | intermediate |
| IPAc | Isopropyl acetate |
| L | liter |
| LC | liquid chromatography |
| LiHMDS | lithium bis(trimethylsilyl)amide |
| Me | Methyl |
| MeOH | Methanol |
| min | Minutes |
| μL | microliter |
| mL | milliliter |
| MPLC | medium pressure liquid chromatography |
| MS | mass spectrometry |
| NBS | N-bromo-succinimide |
| NMP | N-methylpyrrolidone |
| NP | normal phase |
| n.a. | not available |
| PE | petroleum ether |
| PBS | phosphate-buffered saline |
| Ph | Phenyl |
| Pr | Propyl |
| Pyr | Pyridine |
| rac | Racemic |
| Rf ($R_f$) | retention factor |
| RP | reversed phase |
| Rt (HPLC) | Retention time (HPLC) |
| RT | room temperature (about 20° C.) |
| sat. | saturated |
| SFC | supercritical fluid chromatography |
| TBAF | tetrabutylammonium fluoride |
| TBME | tert-butylmethylether |
| TBTU | benzotriazolyl tetramethyluronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TLC | thin-layer chromatography on $SiO_2$ |
| Ts | p-Tosyl |
| TsOH | p-toluenesulphonic acid |
| UC | Ulcerative colitis |
| UV | Ultraviolet |
| VNN-1 | Vanin-1 |
| VNN-2 | Vanin-2 |

Features and advantages of the present invention will become apparent from the following detailed examples which illustrate the fundamentals of the invention by way of example without restricting its scope:

Preparation of the Compounds According to the Invention
General Synthetic Methods The compounds according to the present invention and their intermediates may be obtained using methods of synthesis which are known to the one skilled in the art and described in the literature of organic synthesis. Preferably, the compounds are obtained in analogous fashion to the methods of preparation explained more fully hereinafter, in particular as described in the experimental section. In some cases, the order in carrying out the reaction steps may be varied. Variants of the reaction methods that are known to the one skilled in the art but not described in detail here may also be used.

The general processes for preparing the compounds according to the invention will become apparent to the one skilled in the art studying the following schemes. Starting materials may be prepared by methods that are described in the literature or herein, or may be prepared in an analogous or similar manner. Any functional groups in the starting materials or intermediates may be protected using conventional protecting groups. These protecting groups may be cleaved again at a suitable stage within the reaction sequence using methods familiar to the one skilled in the art.

The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds of formula I may be prepared as shown in Scheme I below.

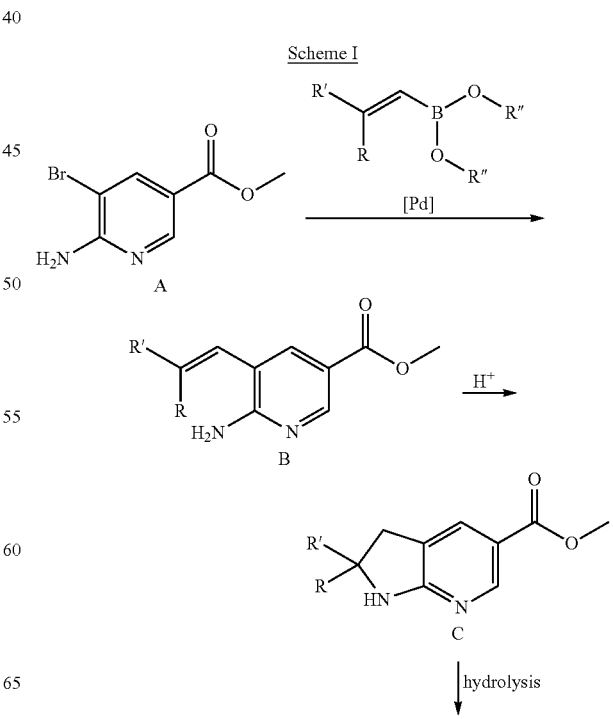

Scheme I

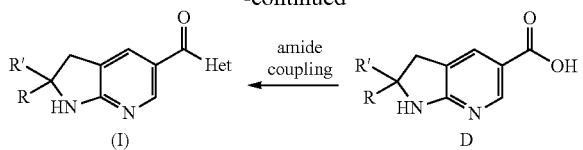

In scheme I, pyridine A, is treated with an appropriate vinylic boronic acid/boronic ester with palladium catalysis (e.g. tetrakis(triphenylphosphine)-palladium) to generate pyridine B. The cyclization to the partially saturated bicycle C is enabled by the use of strong acids (e.g. $H_2SO_4$ or HCl). The ester of heterocycle C is hydrolysed (e.g. with aq. HCl) followed by an amide coupling (e.g. TBTU or HATU as coupling reagent) to afford the compound of general formula (I).

Compounds of formula II may be prepared as shown in Scheme II-a and II-b below.

Scheme II-a

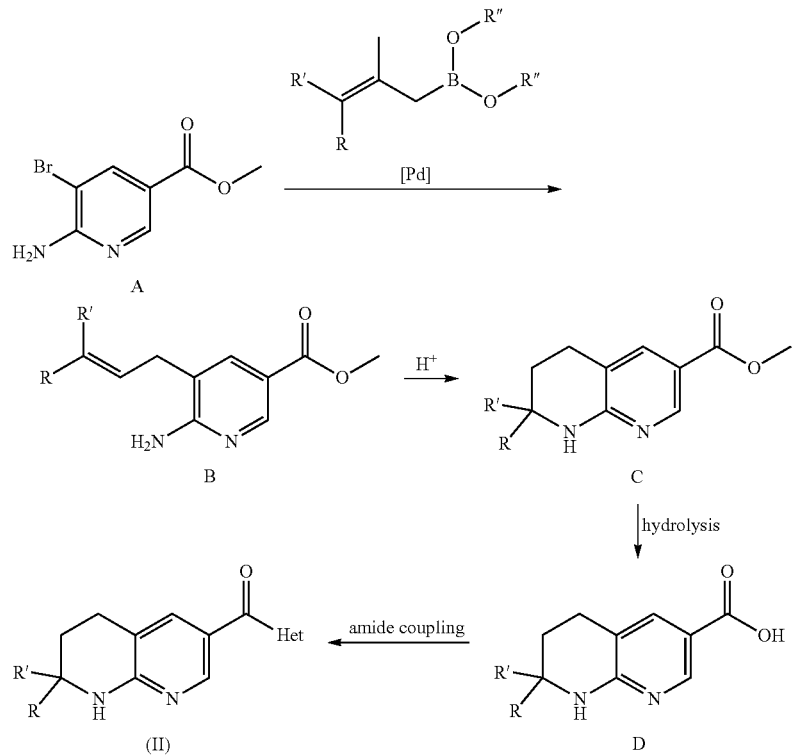

In scheme II-a, pyridine A, is treated with an appropriate allylic boronic acid/boronic ester with palladium catalysis (e.g. tetrakis(triphenylphosphine)-palladium) to generate pyridine B. The cyclization to the partially saturated bicycle C is performed by the use of strong acids (e.g. $H_2SO_4$ or HCl). The ester of heterocycle C is hydrolysed (e.g. with aq. HCl) followed by an amide coupling (e.g. TBTU or HATU as coupling reagent) to afford the compound of general formula (II).

Scheme II-b

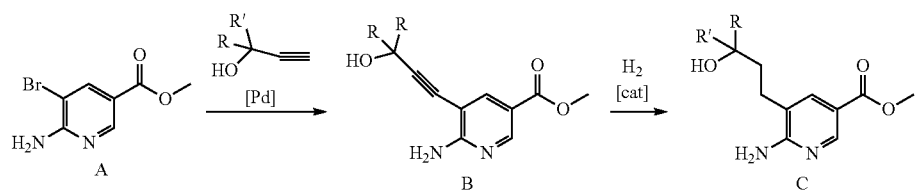

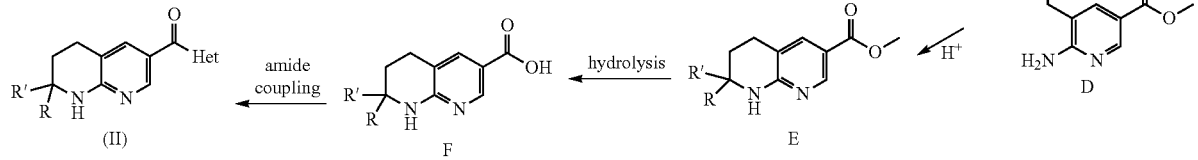

In scheme II-b, pyridine A, is treated with an appropriate propargylic alcohol with palladium and copper catalysis (e.g. tetrakis(triphenylphosphine)-palladium and CuI)) to generate pyridine B. After a catalytic hydrogenation (e.g. Pd/C in presence of $H_2$) of the triple bond to pyridine C the cyclization to the partially saturated bicycle E is made by the use of strong acids (e.g. $H_2SO_4$ or HCl). Alternatively the cyclization can be done via a two-step mechanism where a leaving group is installed (e.g. chloride via treatment with of substrate with thionylchloride) prior to the cyclization conditions (pyridine D). The ester of heterocycle E is hydrolysed (e.g. with aq. HCl) followed by an amide coupling (e.g. TBTU or HATU as coupling reagent) to afford the compound of general formula (II).

Compounds of formula III may be prepared as shown in Scheme III-a and III-b below.

Scheme III-b

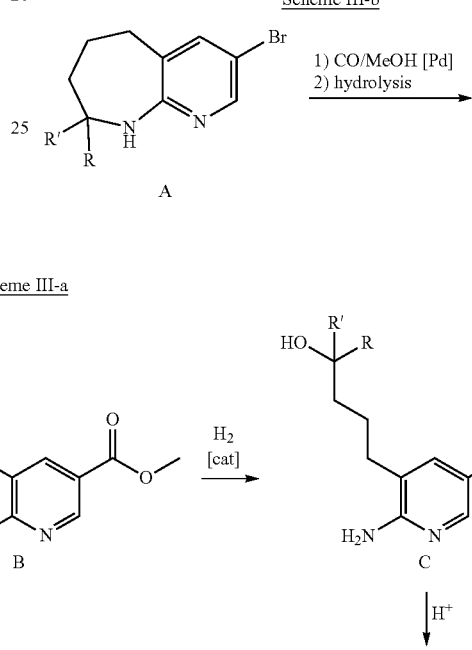

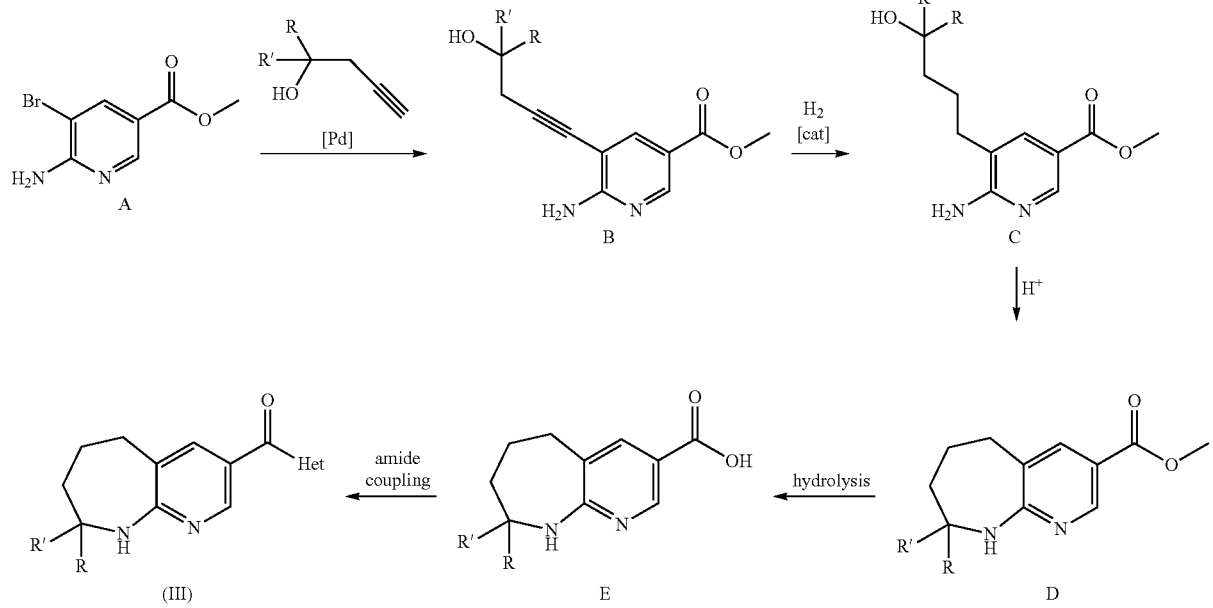

In scheme III-a, pyridine A, is treated with an appropriate homo-propargylic alcohol under palladium catalysis (e.g. tetrakis(triphenylphosphine)-palladium) to generate pyridine B. After a catalytic hydrogenation of the triple bond (e.g. Pd/C in presence of $H_2$) to pyridine C the cyclization to the partially saturated bicycle D is made by the use of strong acids (e.g. $H_2SO_4$ or HCl). The ester of heterocycle D is hydrolysed (e.g. with aq. HCl) followed by an amide

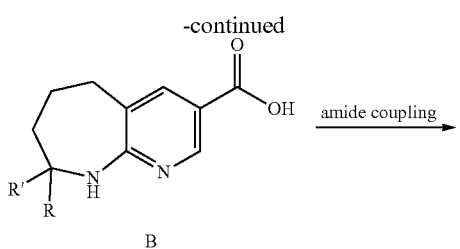

-continued

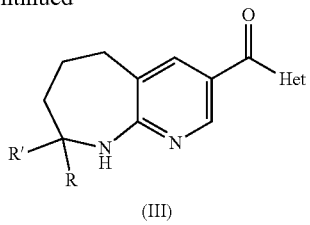

(III)

In scheme III-b, bicycle A, is carbonylated by the use of CO and MeOH in the presence of a Pd-catalyst system (e.g. 1,1'-Bis-(diphenylphosphino)-ferrocene and Pd(OAc)$_2$). The ester of heterocycle B is hydrolysed (e.g. with aq. HCl) followed by an amide coupling (e.g. TBTU or HATU as coupling reagent) to afford the compound of general formula (III).

SYNTHETIC EXAMPLES

The Examples that follow are intended to illustrate the present invention without restricting it. The terms "ambient temperature" and "room temperature" are used interchangeably and designate a temperature of about 20° C.

To a mixture of 1.6 g (6.93 mmol) methyl 6-amino-5-bromopyridine-3-carboxylate in 13.9 mL (27.7 mmol; 2 mol/L) Na$_2$CO$_3$ solution and 30 mL dioxane are added 1.89 g (10.4 mmol) 4,4,5,5-tetramethyl-2-(2-methylprop-1-en-1-yl)-1,3,2-dioxaborolane and the mixture is purged with argon. Then 800 mg (0.69 mmol) tetrakis(triphenylphosphine)-palladium are added and the reaction mixture is stirred at 120° C. for 40 min. After cooling down to RT the reaction mixture is diluted with EtOAc and extracted with a mixture of sat. aq. NaHCO$_3$ solution and water (1:1), the organic layer is dried over Na$_2$SO$_4$, filtered and the solvent is removed in vacuo. The remaining crude product is purified by column chromatography (silica gel; CyH/EtOAc 1/1).

C$_{11}$H$_{14}$N$_2$O$_2$ (M=206.2 g/mol)
ESI-MS: 207 [M+H]$^+$
R$_t$ (HPLC): 0.69 min (method A)

The following compounds are prepared according to the general procedure (Intermediate I.1) described above:

| In. | Starting material | Structure | EI-MS | HPLC retention time (method) [min] |
|---|---|---|---|---|
| I.2 | 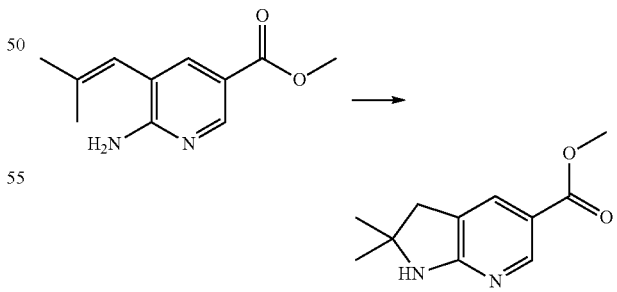 | 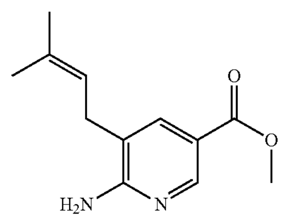 [SMILES: COC(=O)c1cnc(N)c(CC=C(C)C)c1] | 221 [M + H]$^+$ | 0.90 (B) |

Preparation of Starting Compounds

Intermediate I

Intermediate I.1 (General Route)

Methyl 6-amino-5-(2-methylprop-1-en-1-yl)pyridine-3-carboxylate

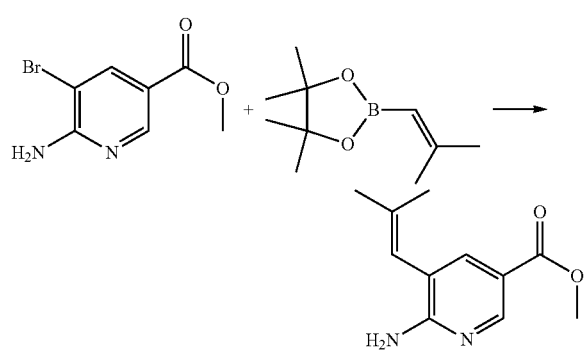

Intermediate II

Intermediate II.1 (General Route)

Methyl 2,2-dimethyl-1H,2H,3H-pyrrolo[2,3-b]pyridine-5-carboxylate

A mixture of 1.36 g (6.27 mmol) methyl 6-amino-5-(2-methylprop-1-en-1-yl)pyridine-3-carboxylate (I.1) in 10 mL (142.7 mmol) conc. H$_2$SO$_4$ is stirred at RT for 20 min. The mixture is poured onto ice water, basified with NaOH (4 mol/L) and extracted with DCM. The combined organic layers are dried over Na$_2$SO$_4$ and concentrated in vacuo to obtain the product.

$C_{11}H_{14}N_2O_2$ (M=206.2 g/mol)
ESI-MS: 207 [M+H]$^+$
$R_t$ (HPLC): 0.62 min (method A)

The following compounds are prepared according to the general procedure (Intermediate II.1) described above:

| In. | Starting material | Structure | Reaction conditions | EI-MS | HPLC retention time (method) [min] |
|---|---|---|---|---|---|
| II.2 | I.2 | 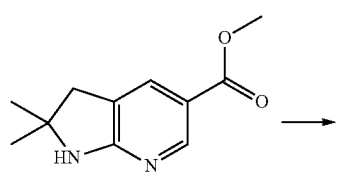 | RT 30 min | 221 [M + H]$^+$ | 0.61 (H) |

Intermediate III

Intermediate III.1 (General Route)

2,2-Dimethyl-1H,2H,3H-pyrrolo[2,3-b]pyridine-5-carboxylic Acid

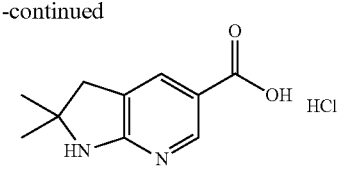

A mixture of 1.51 g (7.32 mmol) intermediate II.1 in 10 mL HCl (conc. 6 mol/L) is stirred at 100° C. for 35 min. After that the reaction mixture is cooled to RT, the precipitate is filtered off and dried to obtain the product.

$C_{10}H_{12}N_2O_2$*HCl (M=228.7 g/mol)
ESI-MS: 193 [M+H]$^+$
$R_t$ (HPLC): 0.54 min (method A)

The following compounds are prepared according to the general procedure (Intermediate III.1) described above:

| In. | Starting material | Structure | Reaction conditions | EI-MS | HPLC retention time (method) [min] |
|---|---|---|---|---|---|
| III.2 | II.2 | 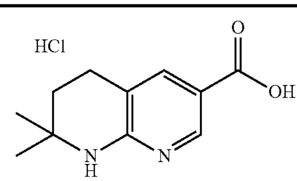 | 80° C. 4.5 h | 207 [M + H]$^+$ | 0.43 (B) |
| III.3 | XIX.1 | 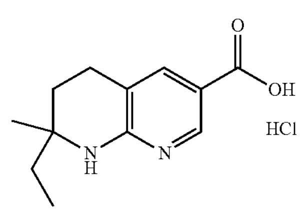 [SMILES: CCC1(C)CCc2cc(C(=O)O)cnc2N1 ; Cl] | 90° C. 2 h evaporation to obtain crude product | 221 [M + H]$^+$ | 0.65 (A) |
| III.4 | XXVI | 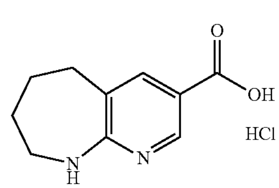 [SMILES: O=C(O)c1cnc2c(c1)CCCCN2 ; Cl] | 75° C. 4 h | 193 [M + H]$^+$ | 0.14 (B) |

Intermediate IV

Intermediate IV.1 (General Route)

1-[(1E)-1-Bromoprop-1-en-2-yl]-4-fluorobenzene

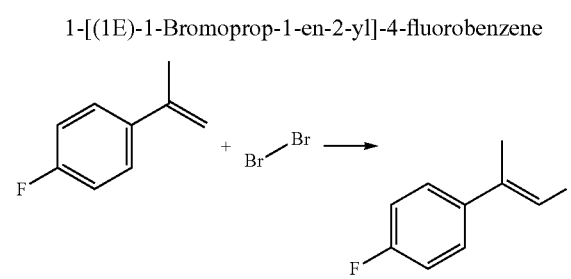

10.0 g (73.4 mmol) 1-Fluoro-4-(prop-1-en-2-yl)benzene are dissolved in 100 mL DCM and cooled to 0° C. Then 3.96 mL (77.1 mmol) Bromine are added dropwise at 0-5° C. and the reaction mixture is stirred at 0° C. until persistent coloring of the solution. The reaction mixture is allowed to warm to RT and stirring is continued for 1 h. 150 mL aq. $Na_2S_2O_3$ solution (1 mol/L) are added and the organic layer is separated, dried and the solvent is removed in vacuo. To the crude intermediate are added 50 mL 2-methylpropan-2-ol and 9.89 g (88.1 mmol) KOtBu by several portions (caveat: exothermic). Finally the reaction mixture is stirred at 70° C. for 5 min. The mixture is cooled to RT, diluted with $H_2O$ and DCM and the layers are separated. The organic layer is dried and the solvents are removed in vacuo. The remaining residue is purified by vacuum distillation (0.03 mbar) to obtain the product.

$C_9H_8BrF$ (M=215.1 g/mol)

EI-MS: 214/216 [M*]$^+$ $R_t$ (HPLC): 1.16 min (method I)

The following compounds are prepared according to the general procedure (Intermediate IV.1) described above:

| In. | Starting material | Structure | EI-MS | HPLC retention time (method) [min] |
|---|---|---|---|---|
| IV.2 | XIV | ![structure](meta-fluoro styryl bromide) | 214/216 [M*]$^+$ | 1.14 (A) |

Intermediate V

Intermediate V.1 (General Route)

1-[(1E)-1-Bromoprop-1-en-2-yl]-4-chlorobenzene

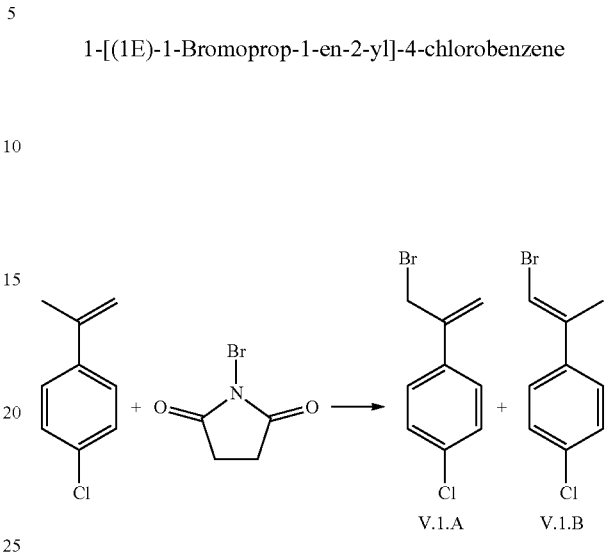

To a mixture of 30 mL (0.21 mol) 1-chloro-4-(prop-1-en-2-yl)benzene in 100 mL chlorobenzene are added 40.7 g (229 mmol) N-bromosuccinimide and 1.71 g (10.4 mmol) 2,2'-azobis(isobutyronitrile) and the mixture is stirred at 132° C. for 20 min. After cooling down the reaction mixture is filtered, the precipitate is washed once with DCM and the solvent is removed in vacuo. The crude product is purified by column chromatography (silica gel; PE/DCM, 9/1) to obtain the two products.

Product A $C_9H_8BrCl$ (M=231.5 g/mol)

ESI-MS: 230/232 [M+H]$^+$ $R_f$ (TLC) 0.45 (PE/DCM 9/1)

Product B $C_9H_8BrCl$ (M=231.5 g/mol)

ESI-MS: 230/232 [M+H]$^+$ $R_f$ (TLC) 0.59 (PE/DCM 9/1)

The following compounds are prepared according to the general procedure (Intermediate V.1) described above:

| In. | Starting material | Structure | Reaction conditions | EI-MS | HPLC retention time (method) [min] |
|---|---|---|---|---|---|
| V.2.A | ![isopropenylbenzene] | ![allyl bromide styrene] | 130° C. 20 min | 196/198 [M + H]$^+$ | 1.05 (A) |

| In. | Starting material | Structure | Reaction conditions | EI-MS | HPLC retention time (method) [min] |
|---|---|---|---|---|---|
| V.2.B | | 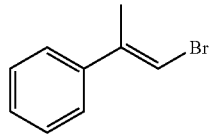 | 130° C. 20 min | 196/198 [M + H]⁺ | 1.13 (A) |
| V.3.A | XIV.2 | 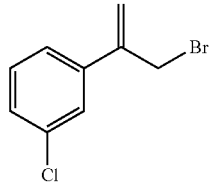 | 130° C. 20 min | 230/232 [M + H]⁺ | 1.11 (A) |
| V.3.B | XIV.2 | 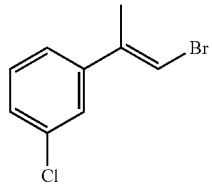 | 130° C. 20 min | 230/232 [M + H]⁺ | 1.19 (A) |

Intermediate VI

Intermediate VI.1 (General Route)

2-[(1E)-2-(4-Fluorophenyl)prop-1-en-1-yl]-4,4,5,5-tetramethyl-1,3,2-dioxaborolane

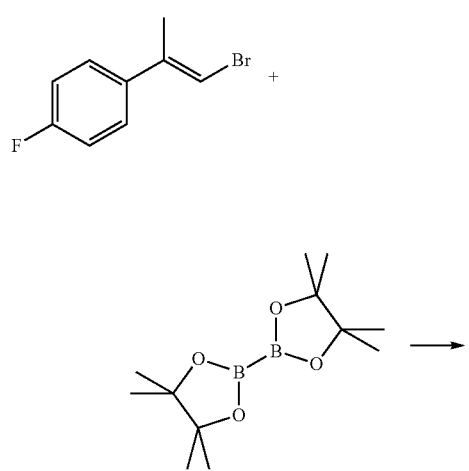

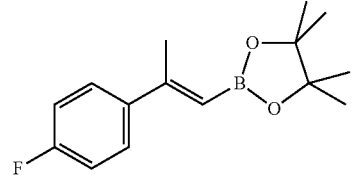

A mixture of 10.0 g (46.5 mmol) intermediate IV.1, 17.9 g (69.7 mmol) 4,4,5,5-tetramethyl-2-(4,4,5,5-tetramethyl-1,3,2-dioxaborolan-2-yl)-1,3,2-dioxaborolane and 11.9 g (121 mmol) potassium acetate in 100 mL dioxane is purged with argon. Then 3.80 g (4.65 mmol) [1,1'-bis(diphenylphosphino)ferrocene]dichloropalladium(II) complex with DCM (1:1) are added and the mixture is stirred at 90° C. for 1 h. After cooling down to RT the reaction mixture is diluted with EtOAc and washed with a mixture of sat. aq. $NaHCO_3$ solution and water (1:1), the organic layer is dried over $Na_2SO_4$, filtered and the solvent is removed in vacuo. The crude product is purified by column chromatography (silica gel; CyH/EtOAc) to obtain the product.

$C_{15}H_{20}BFO_2$ (M=262.1 g/mol)

ESI-MS: 263 [M+H]⁺

$R_t$ (HPLC): 1.24 min (method A)

The following compounds are prepared according to the general procedure (Intermediate VI.1) described above:

| In. | Starting material | Structure | Reaction conditions | ESI-MS | HPLC retention time (method) [min] |
|---|---|---|---|---|---|
| VI.2 | V.2.B | 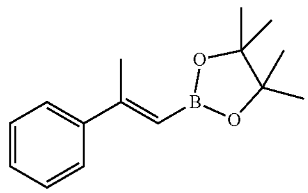 [SMILES: C/C(=C\B1OC(C)(C)C(C)(C)O1)c1ccccc1] | 100° C. 1.5 h | 245 [M + H]⁺ | 1.20 (A) |
| VI.3 | IV.2. | 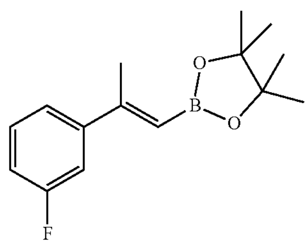 [SMILES: C/C(=C\B1OC(C)(C)C(C)(C)O1)c1cccc(F)c1] | 90° C. 2 h | 263 [M + H]⁺ | 1.25 (A) |
| VI.4 | V.3.A | 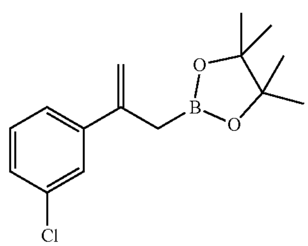 [SMILES: C=C(CB1OC(C)(C)C(C)(C)O1)c1cccc(Cl)c1] | 120° C. 20 min | 279 [M + H]⁺ | 1.21 (A) |
| VI.5 | V.1.B | 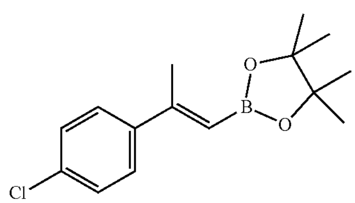 [SMILES: C/C(=C\B1OC(C)(C)C(C)(C)O1)c1ccc(Cl)cc1] | 120° C. 1 h | 279/81 [M + H]⁺ | 1.26 (A) |

Intermediate VII

Intermediate VII.1 (General Route)

Methyl 6-amino-5-[(1E)-2-(4-fluorophenyl)prop-1-en-1-yl]pyridine-3-carboxylate

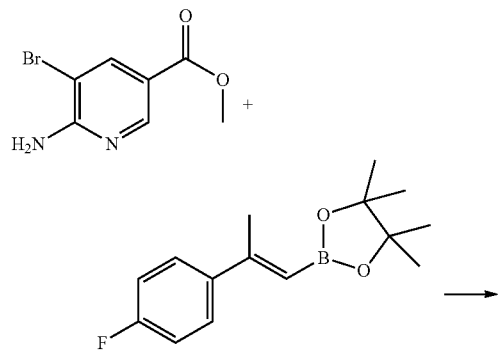

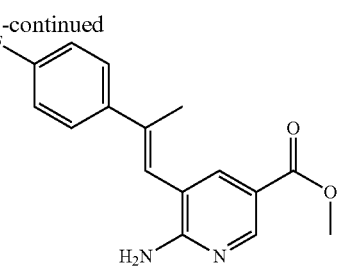

To 0.60 g (2.61 mmol) methyl 6-amino-5-bromopyridine-3-carboxylate in 5.23 mL (10.5 mmol; 2 mol/L) Na₂CO₃ solution and 10 mL dioxane are added 0.69 g (2.61 mmol) intermediate VI.1 and the resulting mixture is purged with argon. Then 302 mg (0.26 mmol) tetrakis(triphenylphosphine)-palladium(0) are added and the reaction mixture is stirred at 120° C. for 40 min. After cooling down to RT the reaction mixture is diluted with EtOAc and washed with a mixture of sat. aq. NaHCO₃ solution and water (1:1), the organic layer is dried over Na₂SO₄, filtered and the solvent is removed in vacuo. The remaining crude product is purified by column chromatography (silica gel; CyH/EtOAc 1/1) to obtain the product.

$C_{16}H_{15}FN_2O_2$ (M=286.3 g/mol)
ESI-MS: 287 [M+H]$^+$
R$_t$ (HPLC): 0.81 min (method A)

The following compounds are prepared according to the general procedure (Intermediate VII.1) described above:

| In. | Starting material | Structure | Reaction conditions | ESI-MS | HPLC retention time (method) [min] |
|---|---|---|---|---|---|
| VII.2 | VI.2 | 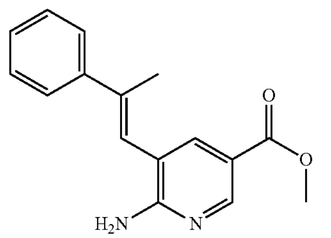 [SMILES: COC(=O)c1cnc(N)c(/C=C(\C)c2ccccc2)c1] | 120° C. 30 min | 269 [M + H]$^+$ | 0.81 (A) |
| VII.3 | VI.3 | 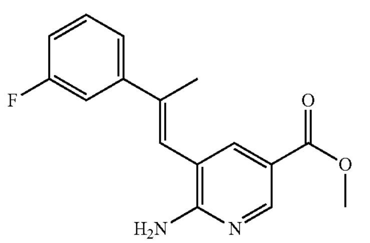 [SMILES: COC(=O)c1cnc(N)c(/C=C(\C)c2cccc(F)c2)c1] | 120° C. 30 min | 287 [M + H]$^+$ | 0.82 (A) |
| VII.4 | VI.4 | 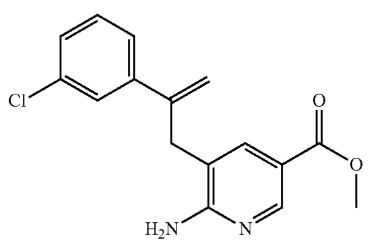 [SMILES: C=C(Cc1cc(C(=O)OC)cnc1N)c1cccc(Cl)c1] | 120° C. 40 min | 303/05 [M + H]$^+$ | 0.83 (A) |
| VII.5 | VI.5 | 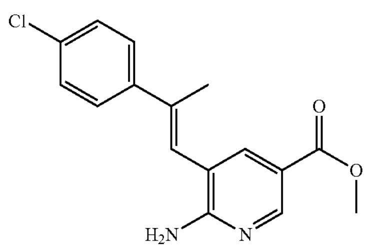 [SMILES: COC(=O)c1cnc(N)c(/C=C(\C)c2ccc(Cl)cc2)c1] | 120° C. 60 min | 303 [M + H]$^+$ | 0.86 (A) |

Intermediate VIII

Intermediate VIII.1 (General Route)

Methyl 2-(4-fluorophenyl)-2-methyl-1H,2H,3H-pyrrolo[2,3-b]pyridine-5-carboxylate

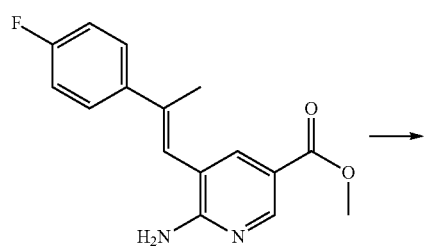

→

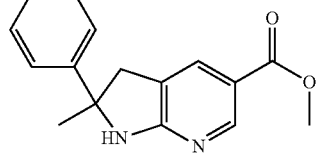

A mixture of 4.50 g (14.15 mmol) intermediate VII.1 and 30 mL (428 mmol) conc. $H_2SO_4$ is stirred at RT for 80 min. The mixture is poured into ice water, slightly basified with NaOH (6 mol/L) and extracted with DCM. The combined organic layers are dried over $Na_2SO_4$ and the solvent is removed in vacuo. The remaining solid is triturated with diethylether.

$C_{16}H_{15}ClN_2O_2$ (M=286.3 g/mol)
ESI-MS: 287 [M+H]$^+$
$R_t$ (HPLC): 0.77 min (method I)

The following compounds are prepared according to the general procedure (Intermediate VIII.1) described above:

| In. | Starting material | Structure | Reaction conditions | ESI-MS | HPLC retention time (method) [min] |
|---|---|---|---|---|---|
| VIII.2 | VII.2 | ![structure] | RT 10 min | 269 [M + H]$^+$ | 0.76 (A) |
| VIII.3 | VII.3 | ![structure] | RT 20 min Purification by silica gel, CyH/EtOAc | 287 [M + H]$^+$ | 0.77 (A) |
| VIII.4 | VII.4 | ![structure] | RT 20 min | 303 [M + H]$^+$ | 0.82 (A) |
| VIII.5 | VII.5 | ![structure] | RT 10 min | 303 [M + H]$^+$ | 0.76 (A) |

Intermediate IX

Intermediate IX.1 (General Route)

Methyl (2R)-2-(4-fluorophenyl)-2-methyl-1H,2H,3H-pyrrolo[2,3-b]pyridine-5-carboxylate and Methyl (2S)-2-(4-fluorophenyl)-2-methyl-1H,2H,3H-pyrrolo[2,3-b]pyridine-5-carboxylate

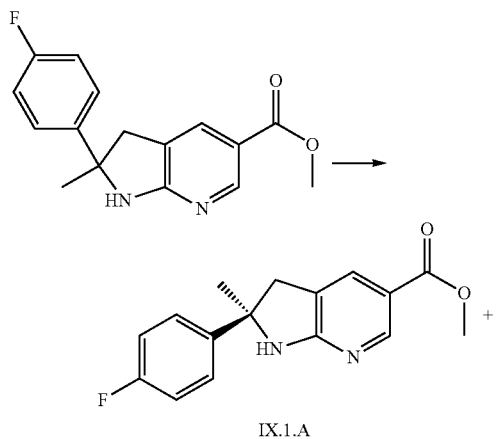

IX.1.A

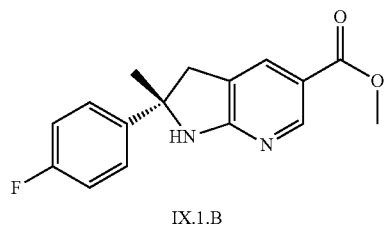

IX.1.B 350 mg (1.21 mmol) intermediate VIII.1 are separated by chiral SFC (method E-for preparative scale).

Product IX.1.A (First Eluting):
$C_{16}H_{15}FN_2O_2$ (M=286.3 g/mol)
ESI-MS: 287 [M+H]+
Rt (HPLC): 2.57 min (method E)

Product IX.1.B (Second Eluting):
$C_{16}H_{15}FN_2O_2$ (M=286.3 g/mol)
Rt (HPLC): 3.88 min (method E)

The following compounds are prepared according to the general procedure (Intermediate IX.1) described above:

| In. | Starting material | Structure | HPLC retention time (method) [min] |
|---|---|---|---|
| IX.2.A | VIII.5 | 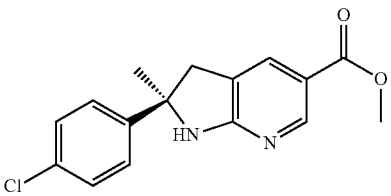 [SMILES: COC(=O)c1cnc2c(c1)C[C@](C)(c1ccc(Cl)cc1)N2] | 2.72 (F) |
| IX.2.B | VIII.5 | 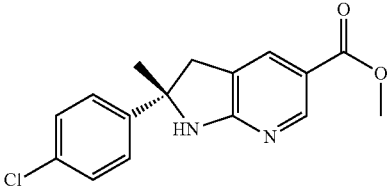 [SMILES: COC(=O)c1cnc2c(c1)C[C@@](C)(c1ccc(Cl)cc1)N2] | 4.50 (F) |
| IX.3.A | VIII.4 | 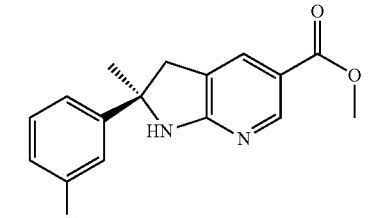 | 2.13 (D) |

-continued

| In. | Starting material | Structure | HPLC retention time (method) [min] |
|---|---|---|---|
| IX.3.B | VIII.4 | methyl (2)-2-(3-chlorophenyl)-2-methyl-2,3-dihydro-1H-pyrrolo[2,3-b]pyridine-5-carboxylate | 9.82 (D) |
| IX.4.A | VIII.3 | methyl (2)-2-(3-fluorophenyl)-2-methyl-2,3-dihydro-1H-pyrrolo[2,3-b]pyridine-5-carboxylate | 3.16 (C) |
| IX.4.B | VIII.3 | methyl (2)-2-(3-fluorophenyl)-2-methyl-2,3-dihydro-1H-pyrrolo[2,3-b]pyridine-5-carboxylate | 3.36 (C) |

Intermediate X

Intermediate X.1.A (General Route)

(2R)-2-(4-Fluorophenyl)-2-methyl-1H,2H,3H-pyrrolo[2,3-b]pyridine-5-carboxylic Acid Hydrochloride

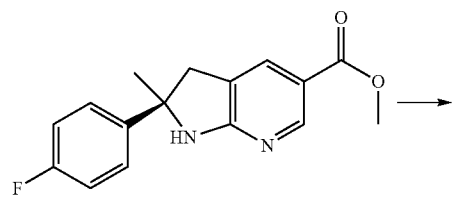
→
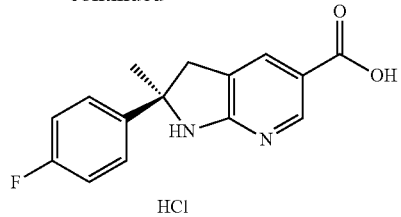

980 mg (3.42 mmol) intermediate IX.1.A in 15 mL HCl (6 mol/L) are stirred at 90° C. for 3 h. The reaction mixture is concentrated in vacuo, 20 mL iso-propanol are added and again concentrated in vacuo. The remaining product is triturated with DIPE.
$C_{15}H_{13}FN_2O_2 \cdot HCl$ (M=308.7 g/mol)
ESI-MS: 273 [M+H]$^+$
R$_t$ (HPLC): 6.87 min (method G)

The following compounds are prepared according to the general procedure (Intermediate X.1) described above:

| In. | Starting material | Structure | Reaction conditions | ESI-MS | HPLC retention time (method) [min] |
|---|---|---|---|---|---|
| X.1.B | IX.1.B | (2S)-2-(4-fluorophenyl)-2-methyl-2,3-dihydro-1H-pyrrolo[2,3-b]pyridine-5-carboxylic acid HCl | 90° C. 3 h | 273 [M + H]$^+$ | 3.35 (G) |

-continued

| In. | Starting material | Structure | Reaction conditions | ESI-MS | HPLC retention time (method) [min] |
|---|---|---|---|---|---|
| X.2 | VIII.2 | (2-methyl-2-phenyl-2,3-dihydro-1H-pyrrolo[2,3-b]pyridine-5-carboxylic acid, HCl) | 80° C. 1.5 h | 255 [M + H]$^+$ | 0.68 (A) |
| X.3.A | IX.4.A | (2-(3-fluorophenyl)-2-methyl-2,3-dihydro-1H-pyrrolo[2,3-b]pyridine-5-carboxylic acid, HCl) | 90° C. 1 h | 273 [M + H]$^+$ | 0.69 (A) |
| X.3.B | IX.4.B | (2-(3-fluorophenyl)-2-methyl-2,3-dihydro-1H-pyrrolo[2,3-b]pyridine-5-carboxylic acid, HCl) | 90° C. 1 h | 273 [M + H]$^+$ | 0.69 (A) |
| X.4.A | IX.2.A | (2-(4-chlorophenyl)-2-methyl-2,3-dihydro-1H-pyrrolo[2,3-b]pyridine-5-carboxylic acid, HCl) | 90° C. 1 h | 289/91 [M + H]$^+$ | 0.75 (A) |
| X.5.A | IX.3.A | (2-(3-chlorophenyl)-2-methyl-2,3-dihydro-1H-pyrrolo[2,3-b]pyridine-5-carboxylic acid, HCl) | 90° C. 1 h | 289/91 [M + H]$^+$ | 0.74 (A) |
| X.5.B | IX.3.B | (2-(3-chlorophenyl)-2-methyl-2,3-dihydro-1H-pyrrolo[2,3-b]pyridine-5-carboxylic acid, HCl) | 90° C. 1 h | 289/91 [M + H]$^+$ | 0.75 (A) |

-continued

| In. | Starting material | Structure | Reaction conditions | ESI-MS | HPLC retention time (method) [min] |
|---|---|---|---|---|---|
| X.6 | VIII.5 | 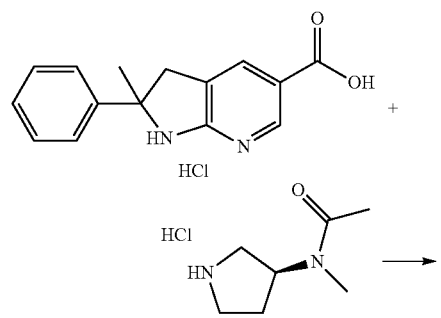 HCl | 80° C. 2 h Purification via HPLC (ACN/H$_2$O/TFA) | 289/91 [M + H]$^+$ | 0.76 (A) |

Intermediate XI

Intermediate XI.1 (General Route)

N-[(3S)-1-[2-(4-Chlorophenyl)-2-methyl-1H,2H,3H-pyrrolo[2,3-b]pyridine-5-carbonyl]pyrrolidin-3-yl]-N-methylacetamide

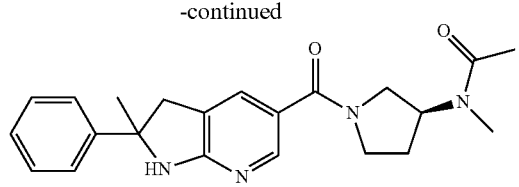

To a mixture of 48 mg (0.19 mmol) intermediate X.2 and 43.8 mg (0.25 mmol) intermediate XVI in 2 mL DMF and 161 μL (0.94 mmol) DIPEA are added 108 mg (0.28 mmol) HATU and the reaction mixture is stirred for 20 min at RT. The reaction mixture is purified by HPLC (ACN/H$_2$O/NH$_4$OH).

$C_{22}H_{26}N_4O_2$ (M=378.5 g/mol)

ESI-MS: 379 [M+H]$^+$

R$_t$ (HPLC): 0.82 min (method B)

The following compounds are prepared according to the general procedure (Intermediate XI.1) described above:

| In. | Starting materials | | Structure | Reaction conditions | ESI-MS | HPLC retention time (method) [min] |
|---|---|---|---|---|---|---|
| XI.2 | XXI.3 | XXIII | (structure shown) | RT 10 min | 435 [M + H]$^+$ | 0.77 (B) |
| XI.3 | XXI.3 | XXV | (structure shown) | RT 10 min | 421 [M + H]$^+$ | 0.73 (B) |

Intermediate XII

Intermediate XII.1 (General Route)

(3S)-1-{2,2-Dimethyl-1H,2H,3H-pyrrolo[2,3-b]pyridine-5-carbonyl}-N-methylpyrrolidin-3-amine; Trifluoroacetic Acid

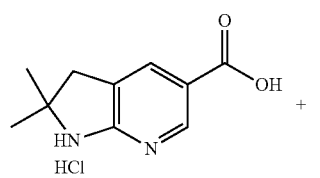

and 920 µL (5.36 mmol) DIPEA are added 870 mg (2.30 mmol) HATU and the reaction mixture is stirred a few minutes. The mixture is purified by HPLC (ACN/H$_2$O/NH$_4$OH).

$C_{20}H_{30}N_4O_3$ (M=374.4 g/mol)

ESI-MS: 375 [M+H]$^+$

R$_t$ (HPLC): 0.92 min (method B)

The above mentioned intermediate is dissolved in 5 mL DCM, 1 mL TFA is added and the mixture is stirred at RT for 2 h. Afterwards all volatiles are removed in vacuo.

$C_{15}H_{22}N_4O * C_2HF_3O_2$ (M=388.4 g/mol)

ESI-MS: 275 [M+H]$^+$

R$_t$ (HPLC): 0.72 min (method B)

The following compounds are prepared according to the general procedure (Intermediate XII.1) described above:

| In. | Starting materials | Structure | ESI-MS | HPLC retention time (method) [min] |
|---|---|---|---|---|
| XII.2 | III.2 | 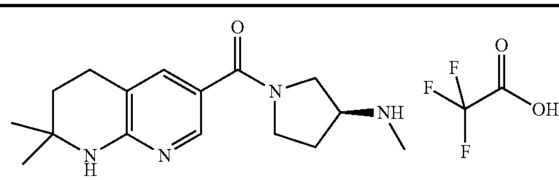 | 289 [M + H]$^+$ | 0.75 (B) |

To a mixture of 350 mg (1.53 mmol) intermediate III.1 and 540 mg (2.30 mmol) intermediate XVI in 6 mL DMF

Intermediate XIII

Intermediate XIII.1 (General Route)

3-[(3S)-Pyrrolidin-3-yl]-1,3-oxazolidin-2-one Hydrochloride

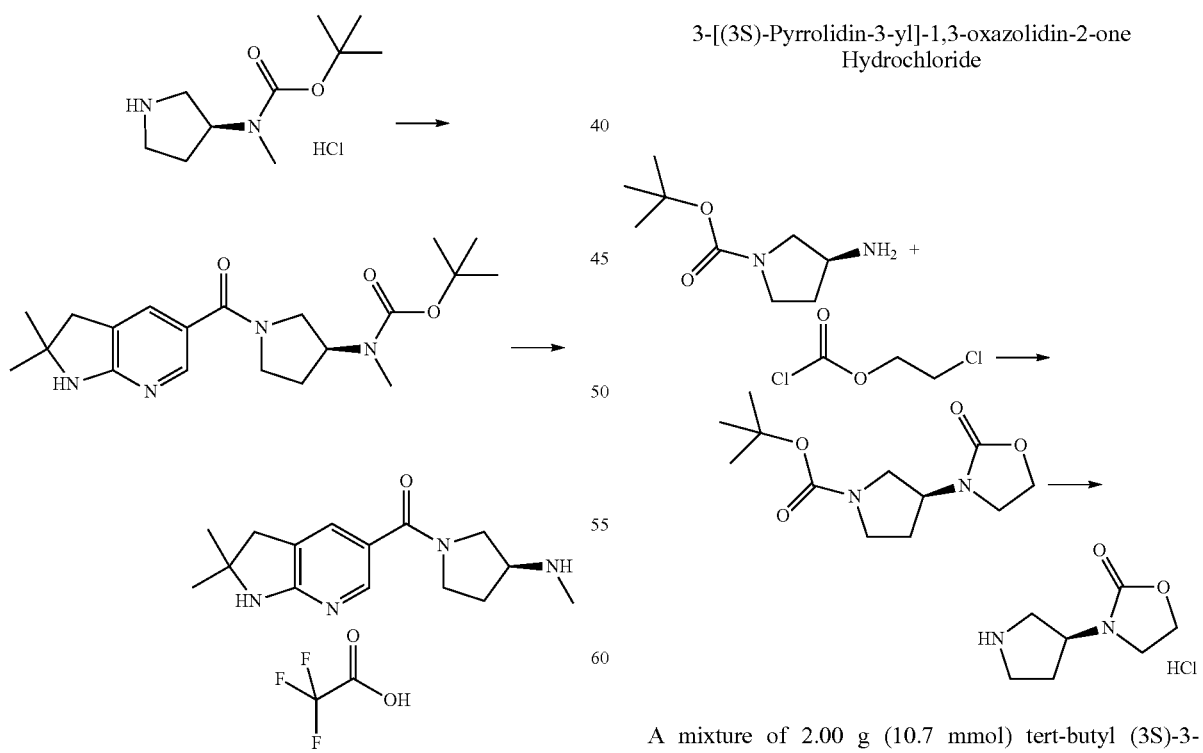

A mixture of 2.00 g (10.7 mmol) tert-butyl (3S)-3-aminopyrrolidine-1-carboxylate in 0.5 mL DCM and 4 mL aq. NaOH (50%) is cooled to 0° C. A mixture of 1.38 g (9.66 mmol) 2-chloroethyl carbonochloridate in 0.5 mL DCM is added dropwise and the reaction mixture is stirred at 0° for 1 h. 3.48 g (5.37 mmol) tetrabutylammonium hydroxide (40% in MeOH) is added and the mixture is stirred overnight at RT. The mixture is quenched with H$_2$O and extracted with DCM. The combined organic layers are dried over a phase separator cartridge and the solvent is removed on vacuo.

The crude product is purified by column chromatography (silica gel; CyH/EtOAc) and the solvents are removed in vacuo.

C$_{12}$H$_{20}$N$_2$O$_4$ (M=256.3 g/mol)
ESI-MS: 201 [M-tBU+H]$^+$
R$_t$ (HPLC): 0.82 min (method B)

The above mentioned product is added to 2.5 mL dioxane, 5 mL (20.0 mmol) HCl in dioxane (4 mol/L) and some MeOH and the mixture is stirred overnight at RT. The solvent is removed in vacuo to obtain the product.

C$_7$H$_{12}$N$_2$O$_2$*HCl (M=192.6 g/mol)
ESI-MS: 157 [M+H]$^+$
R$_t$ (HPLC): 0.17 min (method B)

The following compounds are prepared according to the general procedure (Intermediate XIII.1) described above:

| In. | Starting materials | Structure | ESI-MS | HPLC retention time (method) [min] |
|---|---|---|---|---|
| XIII.2 | tert-butyl (3S)-3-amino-pyrrolidine-1-carboxylate | 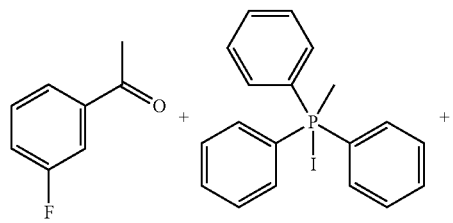 | 155 [M + H]$^+$ | 0.27 (B) |

Intermediate XIV

Intermediate XIV.1 (General Route)

1-Fluoro-3-(prop-1-en-2-yl)benzene

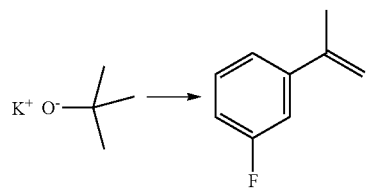

A mixture of 16.1 g (39.8 mmol) iodo(methyl)triphenylphosphane in 130 mL THF is cooled with an icebath. Then 4.47 g (39.8 mmol) potassium 2-methylpropan-2-olate are added during ice cooling and the reaction mixture is stirred for 1 h. After that a solution of 5.00 g (36.2 mmol) 1-(3-fluorophenyl)ethan-1-one in 20 mL THF is added during ice cooling and the mixture is stirred at RT for 1 h.

The mixture is quenched with sat.aq. NH$_4$Cl solution and the layers are separated. The organic layer is dried and the solvent is removed in vacuo.

50 mL PE are added and the mixture is stirred. The obtained oil is separated and the PE layer is dried over Na$_2$SO$_4$, filtered and the solvent is removed in vacuo to obtain the product.

C$_9$H$_9$F (M=136.2 g/mol)
EI-MS: 136 [M*]$^+$
R$_t$ (HPLC): 1.09 min (method A)

The following compounds are prepared according to the general procedure (Intermediate XIV.1) described above:

| In. | Starting material | Structure | Reaction conditions | EI-MS | HPLC retention time (method) [min] |
|---|---|---|---|---|---|
| XIV.2 | 1-(3-chlorophenyl)ethan-1-one | 1-chloro-3-(prop-1-en-2-yl)benzene | 0° C., 1 h RT, 1 h | 152 [M*]$^+$ | 1.14 (A) |

Intermediate XV

N-Methyl-N-[(3S)-pyrrolidin-3-yl]pyrimidin-2-amine hydrochloride

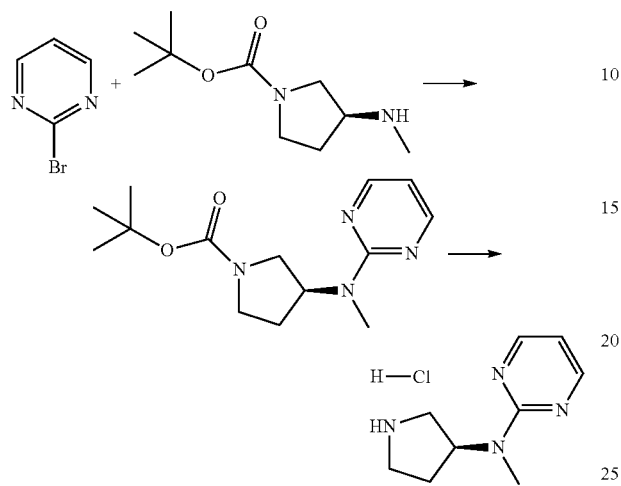

A mixture of 1.00 g (6.29 mmol) 2-bromopyrimidine, 1.51 g (7.55 mmol) tert-butyl (3S)-3-(methylamino)pyrrolidine-1-carboxylate, 3.81 mL (22.0 mmol) DIPEA and 10 mL DMF is stirred at 120° C. for 2 h. The solvent is removed in vacuo and the crude product A is purified by column chromatography (silica gel; DCM/MeOH)

$C_{14}H_{22}N_4O_2$ (M=278.3 g/mol)
ESI-MS: 279 [M+H]$^+$
$R_t$ (HPLC): 0.87 min (method A)

To the above mentioned product are added 10 mL MeOH and 4 mL HCl in dioxane (4 mol/L) and the mixture is stirred overnight at RT. The solvents are removed in vacuo to obtain the final product.

$C_9H_{14}N_4$*HCl (M=214.7 g/mol)
ESI-MS: 179 [M+H]$^+$
$R_t$ (HPLC): 0.15 min (method A)

Intermediate XVI

N-Methyl-N-[(3S)-pyrrolidin-3-yl]acetamide hydrochloride

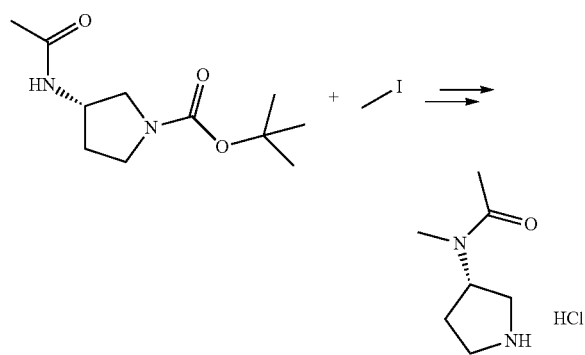

A mixture of 2.5 g (11.0 mmol) tert-butyl (3S)-3-acetamidopyrrolidine-1-carboxylate and 1 mL (15.9 mmol) iodomethane in 25 mL THF is cooled to −10° C. Then 0.75 g (18.8 mmol) NaH (60%) are added and the mixture is stirred overnight at RT. The reaction mixture is quenched with $H_2O$ and EtOAc and stirred vigorously for 5 min. The layers are separated and the $H_2O$ layer is extracted with EtOAc. The combined organic layers are dried over a phase separator cartridge and concentrated in vacuo. The residue is treated with 10 mL HCl in dioxane and stirred at RT. The obtained precipitate is filtered off, washed with dioxane and dried in vacuo to obtain the product.

$C_7H_{14}N_2O$*HCl (M=178.7 g/mol)
ESI-MS: 143 [M+H]$^+$
$R_t$ (HPLC): 0.29 min (method B)

Intermediate XVII

Intermediate XVII.1 (General Route)

Methyl 6-amino-5-(4-hydroxy-4-methylpent-1-yn-1-yl)pyridine-3-carboxylate

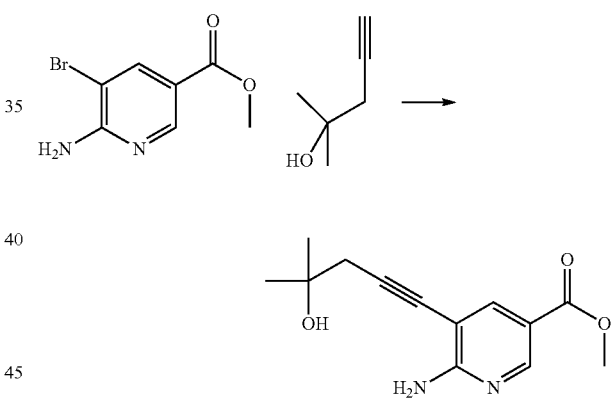

To 0.40 g (1.73 mmol) methyl 6-amino-5-bromopyridine-3-carboxylate and 0.22 g (2.25 mmol) 2-methylpent-4-yn-2-ol in 8 mL ACN are added 0.84 mL (6.06 mmol) TEA, 33.0 mg (0.17 mmol) Cu(I)I and 0.20 g (0.17 mmol) tetrakis(triphenylphosphine)-palladium(0) and the reaction mixture is stirred at 80° C. for 1 h. After cooling down to RT the reaction mixture is diluted with EtOAc and washed with a mixture of sat. aq. NH$_4$Cl solution and ammonia (9:1), the organic layer is dried over a phase separator cartridge and the solvent is removed in vacuo. The remaining crude product is purified by column chromatography (silica gel; CyH/EtOAc 9/1) to obtain the product.

$C_{13}H_{16}N_2O_3$ (M=248.2 g/mol)
ESI-MS: 249 [M+H]$^+$
$R_t$ (HPLC): 0.67 min (method A)

The following compounds are prepared according to the general procedure (Intermediate XVII.1) described above:

| In. | Starting material | Structure | Reaction conditions | ESI-MS | HPLC retention time (method) [min] |
|---|---|---|---|---|---|
| XVII.2 | 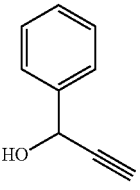 | 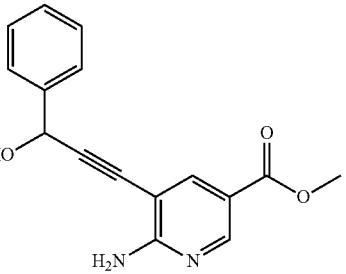 | 80° C 1.5 h Purified by HPLC (ACN/H$_2$O/NH$_4$OH) | 283 [M + H]$^+$ | 0.87 (B) |
| XVII.3 | 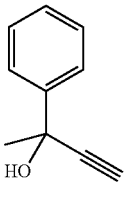 | 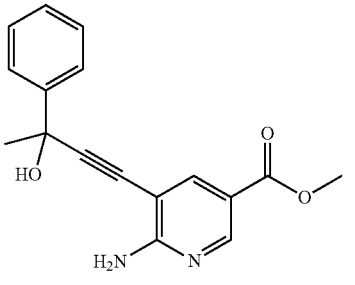 [SMILES: COC(=O)c1cnc(N)c(C#CC(C)(O)c2ccccc2)c1] | 80° C. 1.5 h Purified by HPLC (ACN/H$_2$O/NH$_4$OH) | 297 [M + H]$^+$ | 0.92 (B) |
| XVII.4 | 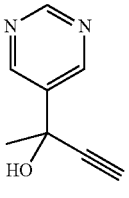 | 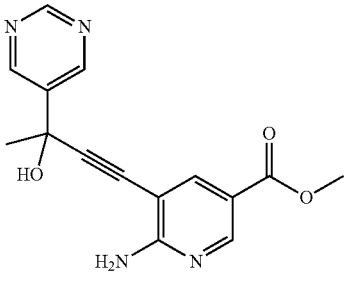 [SMILES: COC(=O)c1cnc(N)c(C#CC(C)(O)c2cncnc2)c1] | 80° C. 35 min | 299 [M + H]$^+$ | 0.68 (A) |

Intermediate XVIII

Intermediate XVIII.1 (General Route)

Methyl 6-amino-5-(4-hydroxy-4-methylpentyl)pyridine-3-carboxylate

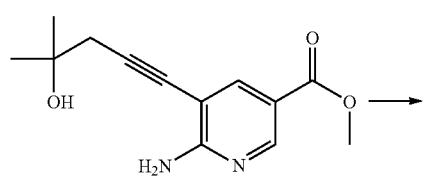 → 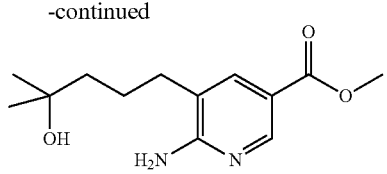

A mixture of 0.40 g (1.61 mmol) of Intermediate XVII.1, 40.0 mg Pd/C (10%) and 10 mL MeOH is hydrogenated at RT and 3 bar of H$_2$ for 1 h. The mixture is filtered and the solvent is removed in vacuo to obtain the product.

C$_{13}$H$_{20}$N$_2$O$_3$ (M=252.3 g/mol)

ESI-MS: 253 [M+H]$^+$

R$_t$ (HPLC): 0.63 min (method A)

The following compounds are prepared according to the general procedure (Intermediate XVIII.1) described above:

| In. | Starting material | Structure | Reaction conditions | ESI-MS | HPLC retention time (method) [min] |
|---|---|---|---|---|---|
| XVIII.2 | XVII.2 | ![structure] | Purified by HPLC (ACN/H₂O/NH₄OH) | 287 [M + H]⁺ | 0.85 (B) |
| XVIII.3 | XVII.3 | ![structure] | Purified by HPLC (ACN/H₂O/NH₄OH) | 301 [M + H]⁺ | 0.88 (B) |
| XVIII.4 | XVII.4 | ![structure] | Pd(II)OH, EtOH RT, overnight | 303 [M + H]⁺ | 0.58 (A) |

Intermediate XIX

Methyl 7-ethyl-7-methyl-5,6,7,8-tetrahydro-1,8-naphthyridine-3-carboxylate

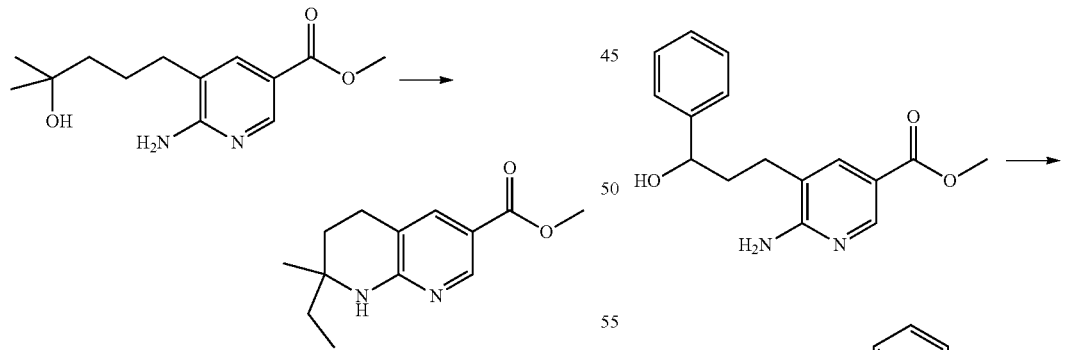

A mixture of 500 mg (1.98 mmol) Intermediate XVIII.1 and 5 mL conc. H₂SO₄ is stirred at RT. The reaction mixture is poured onto ice and carefully basified using aq. NaOH (conc.: 4 mol/L). The aqueous phase is extracted twice with DCM. The org. layers are combined, dried over Na₂SO₄, filtered and the solvent is removed in vacuo. The crude product is purified by HPLC (ACN/H₂O/TFA).

$C_{13}H_{18}N_2O_2$ (M=234.2 g/mol)
ESI-MS: 235 [M+H]⁺
$R_t$ (HPLC): 0.71 min (method A)

Intermediate XX

Methyl 6-amino-5-(3-chloro-3-phenylpropyl)pyridine-3-carboxylate

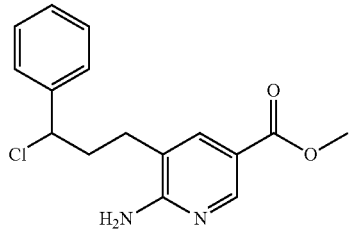 [SMILES: COC(=O)c1cnc(N)c(CCC(C)(O)c2cncnc2)c1]

To a solution of 0.12 g (0.43 mmol) XVIII.2 in 1 mL trichloromethane are added 93.7 µL (1.29 mmol) thionylchloride and the mixture is stirred at 60° C. overnight. The solvent is removed in vacuo to obtain the crude product.

$C_{16}H_{17}ClN_2O_2$ (M=304.7 g/mol)
ESI-MS: 305/307 [M+H]$^+$
$R_t$ (HPLC): 0.81 min (method A)

Intermediate XXI

Intermediate XXI.1 (General Route)

7-Phenyl-5,6,7,8-tetrahydro-1,8-naphthyridine-3-carboxylic acid

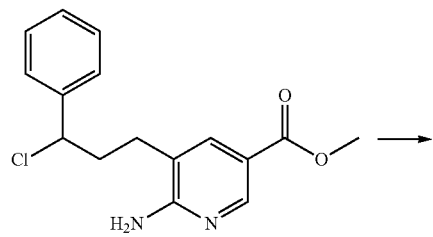

→

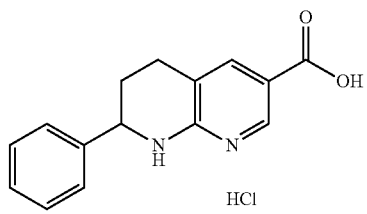

A mixture of 0.13 g (0.43 mmol) intermediate XX in 1 mL HCl (6 mol/L) is stirred at 100° C. for 1.5 h. The solvent is removed in vacuo to obtain the crude product.

$C_{15}H_{14}N_2O_2$ (M=254.2 g/mol)
ESI-MS: 255 [M+H]$^+$
$R_t$ (HPLC): 0.70 min (method A)

The following compounds are prepared according to the general procedure (Intermediate XXI.1) described above:

| In. | Starting material | Structure | Reaction conditions | ESI-MS | HPLC retention time [min] (method) |
|---|---|---|---|---|---|
| XXI.2 | XXII.1 | 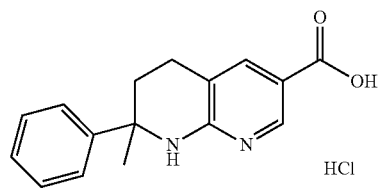 [SMILES: CC1(c2ccccc2)CCc2cc(C(=O)O)cnc2N1 ; Cl] | 100° C. 1.5 h | 269 [M + H]$^+$ | 0.74 (A) |
| XXI.3 | XVIII.4 | 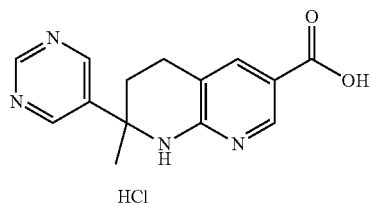 [SMILES: CC1(c2cncnc2)CCc2cc(C(=O)O)cnc2N1 ; Cl] | 120° C. 1.5 h | 271 [M + H]$^+$ | 0.48 (A) |
| XXI.4 | XVIII.1 | 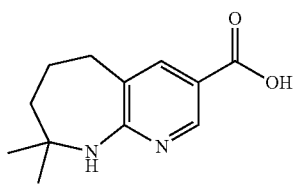 [SMILES: CC1(C)CCCc2cc(C(=O)O)cnc2N1] | 100° C. 16 h Purification via HPLC | 221 [M + H]$^+$ | 0.66 (H) |

Intermediate XXII

Methyl 7-methyl-7-phenyl-5,6,7,8-tetrahydro-1,8-naphthyridine-3-carboxylate

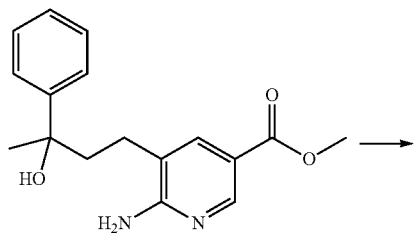

To a solution of 0.10 g (0.33 mmol) example XVIII.3 in 1 mL trichloromethane are added 72.6 µL (1.00 mmol) thionylchloride and the mixture is stirred at 60° C. overnight. Additional 73 µL (1.00 mmol) thionylchloride are added and the mixture is stirred at 60° C. for 3 h. The solvent is removed in vacuo and the crude product is purified by HPLC (ACN/H$_2$O/TFA).

$C_{17}H_{18}N_2O_2$ (M=282.3 g/mol)

ESI-MS: 283 [M+H]$^+$

R$_t$ (HPLC): 0.82 min (method A)

Intermediate XXIII

N-Methyl-N-[(3S)-pyrrolidin-3-yl]cyclobutanecarboxamide

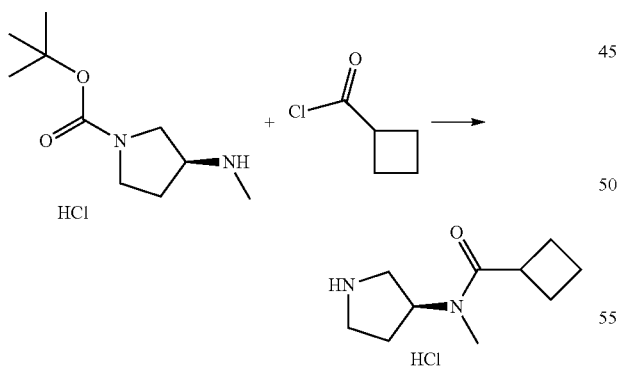

To a mixture of 1.00 g (4.22 mmol) tert-butyl (3S)-3-(methylamino)pyrrolidine-1-carboxylate hydrochloride and 2.94 mL (21.1 mmol) TEA in 25 mL DCM are added dropwise under ice cooling 0.53 mL (4.65 mmol) cyclobutanecarbonyl chloride and the mixture is stirred at 0° C. for 10 min. Then the solids are filtered off and the filtrate is washed 1× with sat. NH$_4$Cl solution, 1× with sat. NaHCO$_3$ solution and 1× with sat. NaCl solution. The organic layer is dried over Na$_2$SO$_4$ and the solvent is removed in vacuo.

Then the residue is added to 3 mL MeOH before 3 mL (12.0 mmol) HCl in dioxane (4 mol/L) are added. The mixture is stirred overnight at RT. The solvent is removed in vacuo to obtain the crude product.

$C_{10}H_{18}N_2O*HCl$ (M=218.7 g/mol)

ESI-MS: 183 [M+H]$^+$

R$_t$ (HPLC): 0.67 min (method B)

Intermediate XXIV tert-Butyl (3S)-3-(N-methylcyclopropaneamido)pyrrolidine-1-carboxylate

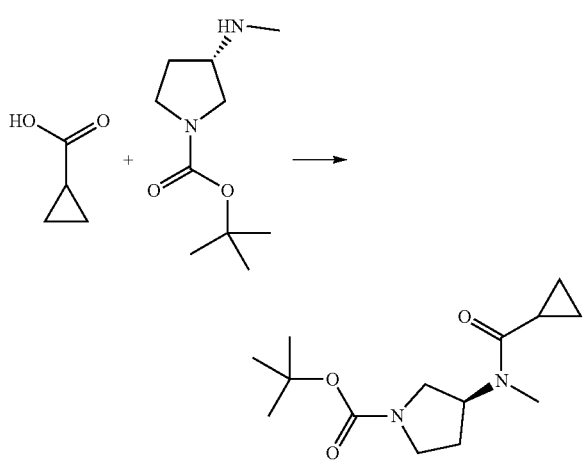

A mixture of 0.38 mL (4.77 mmol) cyclopropanecarboxylic acid, 1.00 g (4.99 mmol) tert-butyl (3S)-3-(methylamino)pyrrolidine-1-carboxylate, 1.69 g (5.25 mmol) TBTU and 2.06 mL (11.9 mmol) DIPEA in 10 mL DMF is stirred overnight at RT. The solvent is removed in vacuo. The residue is diluted with 20 mL sat. NaHCO$_3$ solution and extracted with EtOAc. The combined organic layers are dried over MgSO$_4$, filtered and the solvent is removed in vacuo to obtain the product.

$C_{14}H_{24}N_2O_3$ (M=268.3 g/mol)

ESI-MS: 269 [M+H]$^+$

R$_t$ (HPLC): 0.51 min (method A)

Intermediate XXV

N-Methyl-N-[(3S)-pyrrolidin-3-yl]cyclopropanecarboxamide hydrochloride

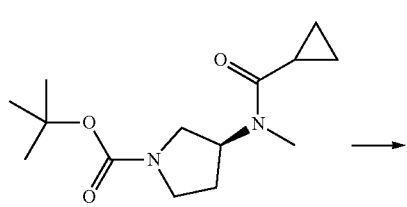

71

-continued

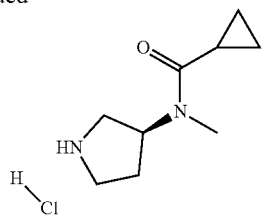

A mixture of 1.27 g intermediate XXIV, 10 mL (40.0 mmol) HCl in dioxane (4 mol/L) and 10 mL dioxane is stirred overnight at RT. The solvent is removed in vacuo to obtain the product.

$C_9H_{16}N_2O*HCl$ (M=204.7 g/mol)
ESI-MS: 169 [M+H]$^+$
$R_t$ (HPLC): 0.58 min (method B)

Intermediate XXVI

Methyl 5H,6H,7H,8H,9H-pyrido[2,3-b]azepine-3-carboxylate

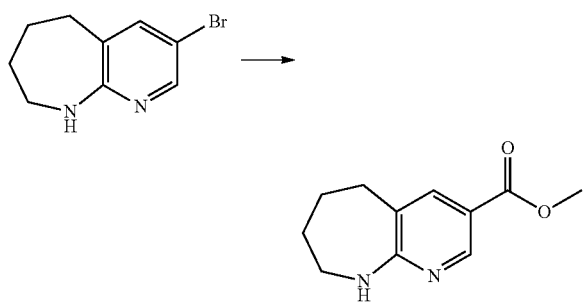

To 2 mL methanol and 2 mL DMF are given 0.20 g (0.88 mmol) 3-bromo-5H,6H,7H,8H,9H-pyrido[2,3-b]azepine, 0.02 g (44.0 µmol) 1,1'-Bis-(diphenylphosphino)-ferrocene, 0.01 g (44.0 µmol) Pd(OAc)$_2$ and 0.25 mL TEA (1.76 mmol). After degassing the reaction mixture is purged with CO (5 bar) and stirred at 80° C. for 18 h. After cooling down to RT the mixture is filtered and the solvent is removed in vacuo. The crude product is purified by HPLC (ACN/H$_2$O/NH$_3$).

$C_{11}H_{14}N_2O_2$ (M=206.2 g/mol)
ESI-MS: 207 [M+H]$^+$
$R_t$ (HPLC): 0.85 min (method B)

Preparation of Final Compounds

Example 1

Example 1.1 (General Route)

N-[(3S)-1-{2,2-Dimethyl-1H,2H,3H-pyrrolo[2,3-b]pyridine-5-carbonyl}pyrrolidin-3-yl]-N-methylacetamide

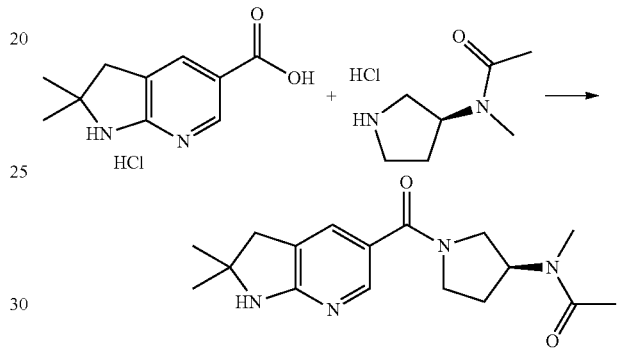

To a mixture of 33.0 mg (0.14 mmol) intermediate III.1 and 38.7 mg (0.22 mmol) intermediate XVI in 1 mL DMF are added 74.0 µL (0.43 mmol) DIPEA and 82.3 mg (0.22 mmol) HATU and the reaction mixture is stirred a few minutes. The mixture is purified by HPLC (ACN/H$_2$O/NH$_4$OH) to obtain the product.

$C_{17}H_{24}N_4O_2$ (M=316.4 g/mol)
ESI-MS: 317 [M+H]$^+$
$R_t$ (HPLC): 0.71 min (method B)

The following compounds are prepared according to the general procedure (example 1.1) described above:

| Ex. | Starting materials | | Structure | Reaction conditions | ESI-MS | HPLC retention time (method) [min] |
|---|---|---|---|---|---|---|
| 1.2 | III.1 | XIII.2 | (structure) | RT 5 min | 329 [M + H]$^+$ | 0.72 (B) |
| 1.3 | III.1 | XIII.1 | (structure) | RT 5 min | 331 [M + H]$^+$ | 0.70 (B) |

| Ex. | Starting materials | Structure | Reaction conditions | ESI-MS | HPLC retention time (method) [min] |
|---|---|---|---|---|---|
| 1.4 | III.1 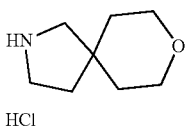 | 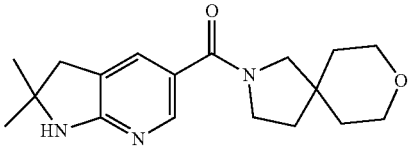 [SMILES: CC1(C)Cc2cc(C(=O)N3CCC4(CCOCC4)C3)cnc2N1] | RT 10 min | 316 [M + H]⁺ | 0.78 (B) |
| 1.5 | III.1 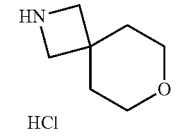 | 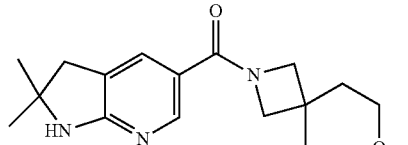 | RT 10 min | 302 [M + H]⁺ | 0.74 (B) |

Example 2

Example 2.1 (General Route)

N-[(3S)-1-{2,2-Dimethyl-1H,2H,3H-pyrrolo[2,3-b]pyridine-5-carbonyl}pyrrolidin-3-yl]-N-methylcyclobutanecarboxamide

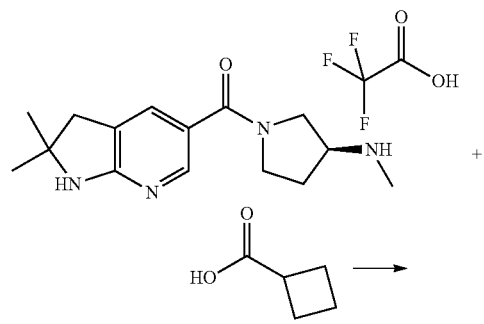

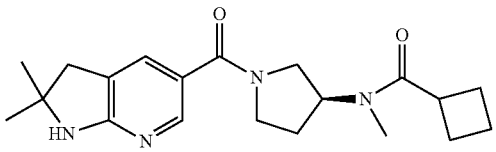

To a mixture of 50.0 mg (0.13 mmol) intermediate XII.1 and 19.3 mg (0.19 mmol) cyclobutanecarboxylic acid in 1 mL (119 mmol) DMF and 77.0 µL (0.45 mmol) DIPEA are added 73.4 mg (0.19 mmol) HATU and the reaction mixture is stirred at RT for 30 min. The mixture is purified by HPLC (ACN/H₂O/NH₄OH) to obtain the product.

$C_{17}H_{24}N_4O_2$ (M=356.5 g/mol)

ESI-MS: 357 [M+H]⁺

R$_t$ (HPLC): 0.89 min (method B)

The following compounds are prepared according to the general procedure (example 2.1) described above:

| Ex. | Starting materials | Structure | Reaction conditions | ESI-MS | HPLC retention time (method) [min] |
|---|---|---|---|---|---|
| 2.2 | XII.1 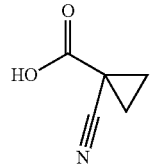 | 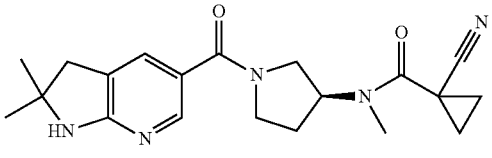 [SMILES: CN(C(=O)C1(C#N)CC1)[C@H]1CCN(C(=O)c2cnc3c(c2)CC(C)(C)N3)C1] | RT 30 min | 368 [M + H]⁺ | 0.76 (B) |
| 2.3 | XII.1 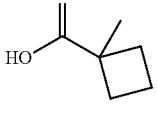 | 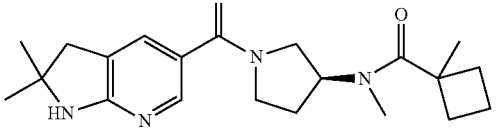 | RT 30 min | 371 [M + H]⁺ | 0.91 (B) |

| Ex. | Starting materials | Structure | Reaction conditions | ESI-MS | HPLC retention time (method) [min] |
|---|---|---|---|---|---|
| 2.4 | XII.1 | 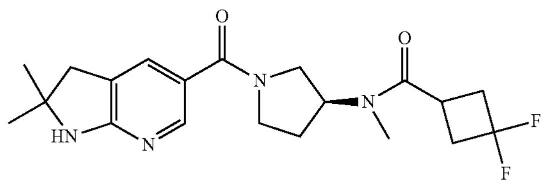 [SMILES: CN(C(=O)C1CC(F)(F)C1)[C@H]1CCN(C(=O)c2cnc3c(c2)CC(C)(C)N3)C1] | RT 30 min | 393 [M + H]⁺ | 0.81 (B) |
| 2.5 | XII.1 | 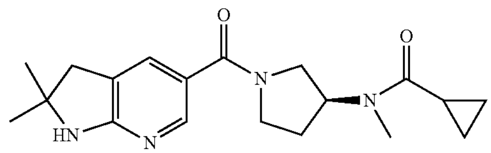 [SMILES: CN(C(=O)C1CC1)[C@H]1CCN(C(=O)c2cnc3c(c2)CC(C)(C)N3)C1] | RT 30 min | 343 [M + H]⁺ | 0.90 (B) |

Example 3

N-[(3S)-1-{2,2-Dimethyl-1H,2H,3H-pyrrolo[2,3-b]pyridine-5-carbonyl}pyrrolidin-3-yl]-N-methylpyrimidin-2-amine

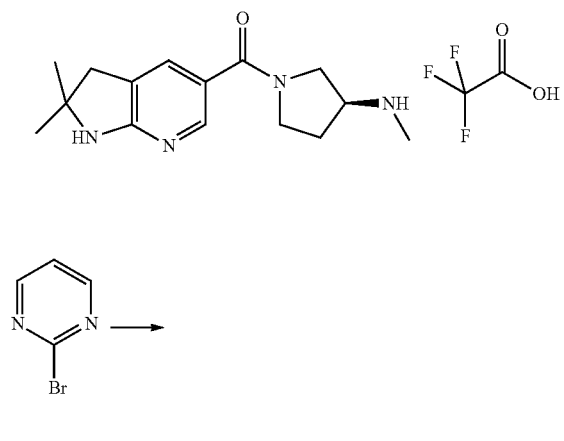

A mixture of 50.0 mg (0.13 mmol) intermediate XII.1 and 22.5 mg (0.14 mmol) 2-bromo-pyrimidine in 111 µL (0.64 mmol) DIPEA and 1.5 mL (18.4 mmol) DMF are stirred overnight at 120° C. The mixture is purified by HPLC (ACN/H₂O/NH₄OH) to obtain the product.

$C_{17}H_{24}N_4O_2$ (M=352.4 g/mol)

ESI-MS: 353 [M+H]⁺

R$_t$ (HPLC): 0.83 min (method B)

Example 4

Example 4.1 (General Route)

3-[(3S)-1-[(2R)-2-(3-Fluorophenyl)-2-methyl-1H,2H,3H-pyrrolo[2,3-b]pyridine-5-carbonyl]pyrrolidin-3-yl]-1,3-oxazolidin-2-one

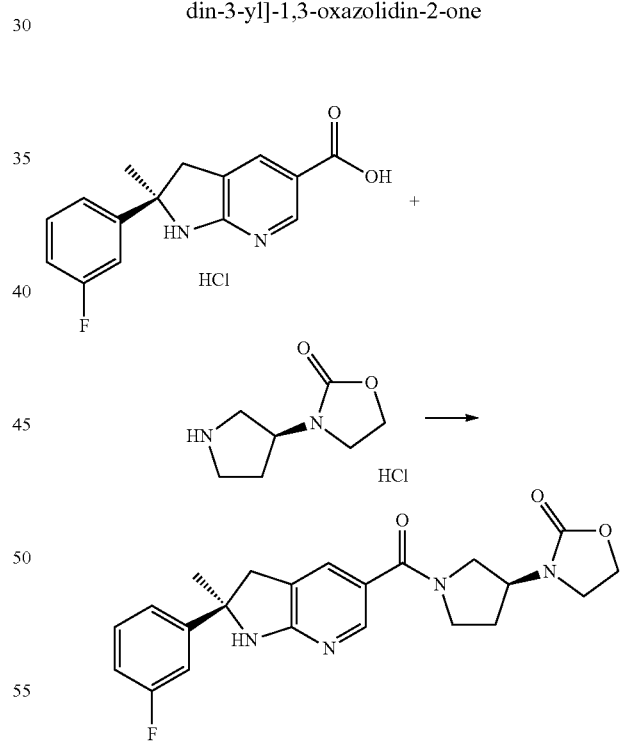

To a mixture of 45.0 mg (0.15 mmol) intermediate X.3.A and 33.7 mg (0.18 mmol) intermediate XIII.1 in 2 mL (30.6 mmol) DMF and 149 µL (0.87 mmol) DIPEA are added 83.1 mg (0.22 mmol) HATU and the reaction mixture is stirred a few minutes. The mixture is purified by HPLC (ACN/H₂O/NH₄OH) to obtain the product.

$C_{22}H_{23}FN_4O_3$ (M=410.4 g/mol)

ESI-MS: 411 [M+H]⁺

R$_t$ (HPLC): 0.70 min (method A)

The following compounds are prepared according to the general procedure (example 4.1) described above:

| Ex. | Starting materials | Structure | Reaction conditions | ESI-MS | HPLC retention time (method) [min] |
|---|---|---|---|---|---|
| 4.2 | X.3.B XVI | 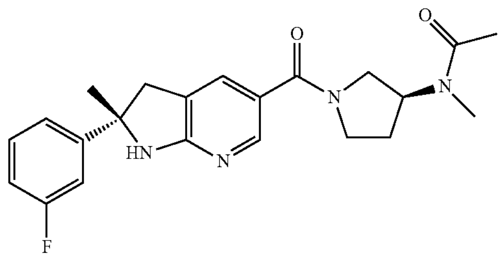 | RT 5 min | 397 [M + H]$^+$ | 0.35 (B) |
| 4.3 | X.3.A XVI | 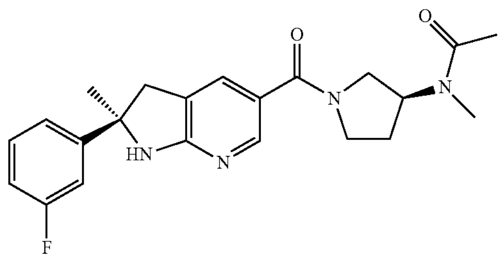 | RT 5 min | 397 [M + H]$^+$ | 0.70 (A) |
| 4.4 | X.3.A XIII.2 | 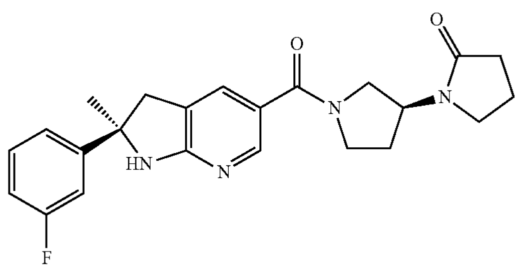 [SMILES: C[C@]1(c2cccc(F)c2)Cc2cc(C(=O)N3CC[C@H](N4CCCC4=O)C3)cnc2N1] | RT 5 min | 409 [M + H]$^+$ | 0.83 (B) |

Example 5

Example 5.1 (General Route)

2-[(2R)-2-(4-Fluorophenyl)-2-methyl-1H,2H,3H-pyrrolo[2,3-b]pyridine-5-carbonyl]-8-oxa-2-azaspiro[4.5]decane

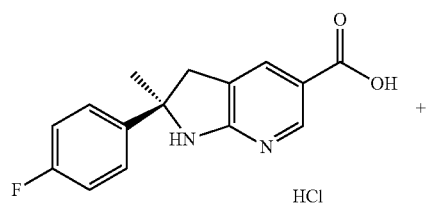

+

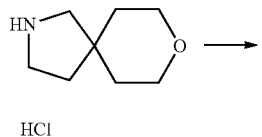

HCl

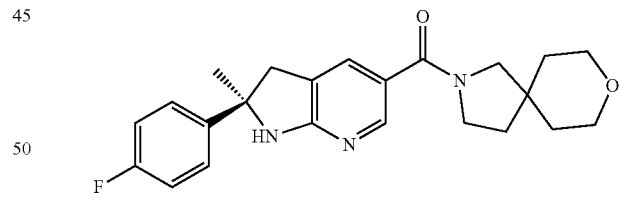

To a mixture of 40.0 mg (0.13 mmol) intermediate X.1.A and 27.6 mg (0.16 mmol) 8-oxa-2-azaspiro[4.5] decane hydrochloride in 1.5 mL (22.9 mmol) DMF and 66.4 µL (0.39 mmol) DIPEA are added 73.9 mg (0.19 mmol) HATU and the reaction mixture is stirred 2 min. The mixture is purified by HPLC (ACN/H$_2$O/NH$_4$OH) to obtain the product.

$C_{23}H_{26}FN_3O_2$ (M=395.4 g/mol)

ESI-MS: 396 [M+H]$^+$ $R_t$ (HPLC): 0.89 min (method B)

The following compounds are prepared according to the general procedure (example 5.1) described above:

| Ex. | Starting materials | | Structure | Reaction conditions | ESI-MS | HPLC retention time (method) [min] |
|---|---|---|---|---|---|---|
| 5.2 | X.1.A | XIII.1 | 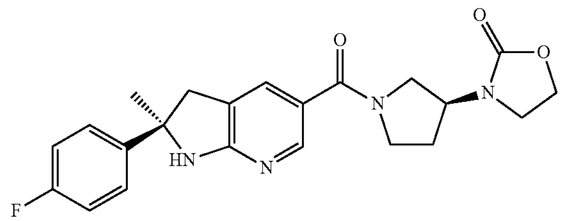 [SMILES: C[C@]1(c2ccc(F)cc2)Cc2cc(C(=O)N3CC[C@H](N4CCOC4=O)C3)cnc2N1] | RT 5 min | 411 [M + H]⁺ | 0.83 (B) |
| 5.3 | X.1.A | XIII.2 | 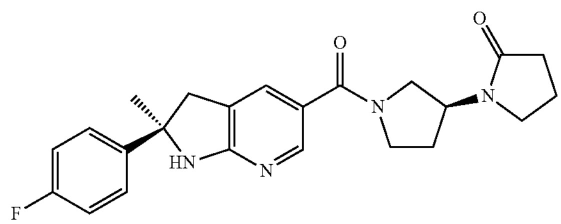 [SMILES: C[C@]1(c2ccc(F)cc2)Cc2cc(C(=O)N3CC[C@H](N4CCCC4=O)C3)cnc2N1] | RT 5 min | 409 [M + H]⁺ | 0.83 (B) |
| 5.4 | X.1.B | XVI | 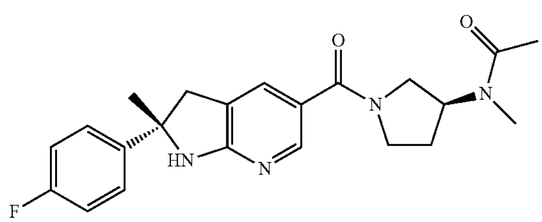 | RT 5 min | 397 [M + H]⁺ | 3.66 (K) |
| 5.5 | X.1.A | XV | 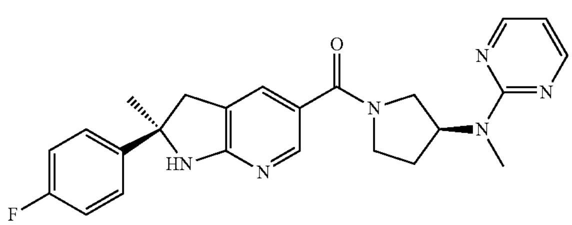 [SMILES: CN(c1ncccn1)[C@H]1CCN(C(=O)c2cnc3c(c2)C[C@](C)(c2ccc(F)cc2)N3)C1] | RT 2 min | 433 [M + H]⁺ | 0.94 (B) |
| 5.6 | X.1.A | | 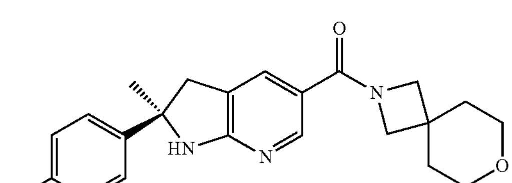 | RT 2 min | 382 [M + H]⁺ | 0.87 (B) |

Example 6

N-[(3S)-1-[(2R)-2-(4-Fluorophenyl)-2-methyl-1H,2H,3H-pyrrolo[2,3-b]pyridine-5-carbonyl]-pyrrolidin-3-yl]-N-methylacetamide

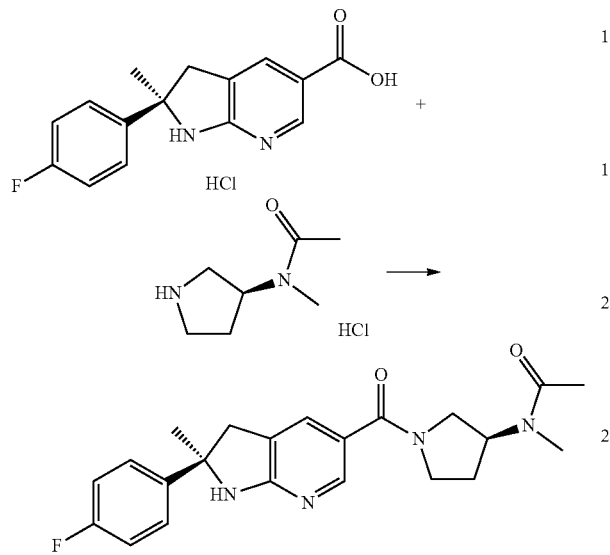

To a mixture of 1.65 g (5.34 mmol) intermediate X.1.A and 1.15 g (6.41 mmol) intermediate XVI in 3.65 mL (21.4 mmol) DIPEA and 20 mL DMF are added 1.80 g (5.61 mmol) TBTU and the reaction mixture is stirred at RT for 10 min. The reaction is diluted with aq. NaHCO$_3$ solution and extracted with EtOAc. The combined organic layers are dried and the solvent is removed in vacuo. The crude product is purified by column chromatography (silica gel; EtOAc/MeOH 4/1) and the solvents are removed in vacuo. The residue is triturated with DIPE, the solid is filtered off, washed with DIPE and dried at 50° C. in vacuo to obtain the product.

$C_{22}H_{25}FN_4O_2$ (M=396.5 g/mol)
ESI-MS: 397 [M+H]$^+$
R$_t$ (HPLC): 3.19 min (method K)

Example 7

Example 7.1 (General Route)

(3'S)-1'-[2-(3-Chlorophenyl)-2-methyl-1H,2H,3H-pyrrolo[2,3-b]pyridine-5-carbonyl]-[1,3'-bipyrrolidine]-2-one

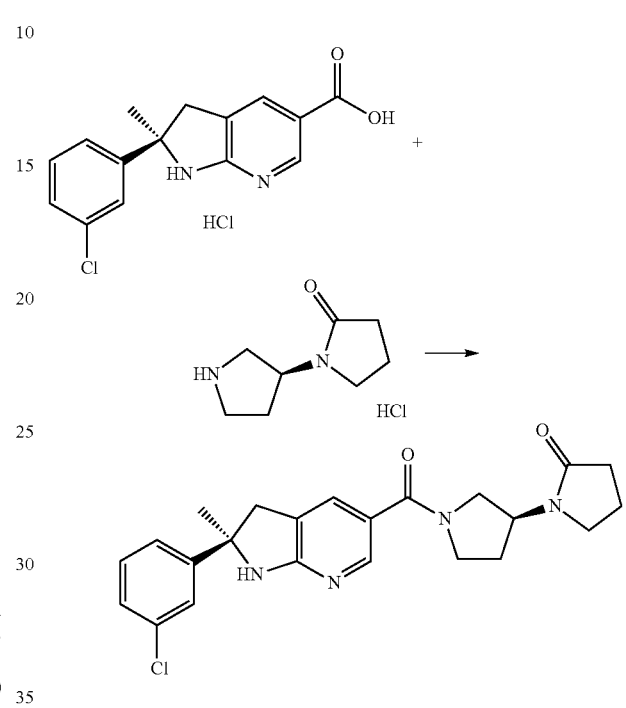

To a mixture of 35.0 mg (0.11 mmol) intermediate X.5.A and 22.6 mg (0.12 mmol) intermediate XIII 2 in 2 mL (30.6 mmol) DMF and 110 µL (0.65 mmol) DIPEA are added 61.4 mg (0.16 mmol) HATU and the reaction mixture is stirred a few minutes. The mixture is purified by HPLC (ACN/H$_2$O/NH$_4$OH) to obtain the product.

$C_{23}H_{25}ClN_4O_2$ (M=424.9 g/mol)
ESI-MS: 425 [M+H]$^+$
R$_t$ (HPLC): 0.74 min (method A)

The following compounds are prepared according to the general procedure (example 7.1) described above:

| Ex. | Starting materials | Structure | Reaction conditions | ESI-MS | HPLC retention time (method) [min] |
|---|---|---|---|---|---|
| 7.2 | X.5.A  XVI | ![structure] | RT 5 min | 413 [M + H]$^+$ | 0.73 (B) |

-continued

| Ex. | Starting materials | Structure | Reaction conditions | ESI-MS | HPLC retention time (method) [min] |
|---|---|---|---|---|---|
| 7.3 | X.5.B XVI | (structure) | RT 5 min | 413 [M + H]+ | 0.74 (A) |
| 7.4 | X.5.A XIII.1 | (structure) | RT 5 min | 427 [M + H]+ | 0.74 (A) |

Example 8

Example 8.1 (General Route)

N-[(3S)-1-[2-(4-Chlorophenyl)-2-methyl-1H,2H,3H-pyrrolo[2,3-b]pyridine-5-carbonyl]pyrrolidin-3-yl]-N-methylacetamide

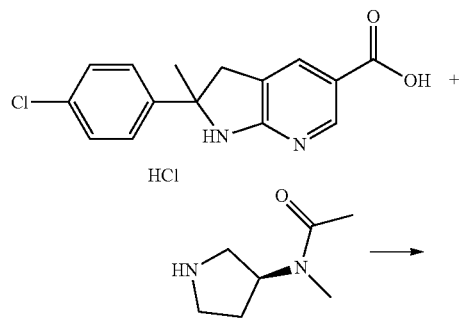

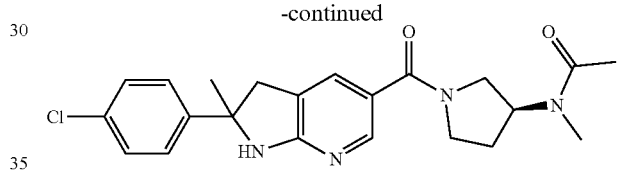

To a mixture of 100 mg (0.31 mmol) intermediate X.6 and 65.6 mg (0.46 mmol) N-methyl-N-[(3S)-pyrrolidin-3-yl]acetamide in 3 mL (45.9 mmol) DMF and 315 μL (1.85 mmol) DIPEA are added 175 mg (0.46 mmol) HATU and the reaction mixture is stirred 20 min. The mixture is purified by HPLC (ACN/H$_2$O/NH$_4$OH) to obtain the product.

$C_{22}H_{25}ClN_4O_2$ (M=412.9 g/mol)

ESI-MS: 413 [M+H]+

R$_t$ (HPLC): 0.87 min (method B)

The following compounds are prepared according to the general procedure (example 8.1) described above:

| Ex. | Starting materials | Structure | Reaction conditions | ESI-MS | HPLC retention time (method) [min] |
|---|---|---|---|---|---|
| 8.2 | X.4.A XIII.1 | (structure) | RT 1 h | 427 [M + H]+ | 0.88 (B) |

-continued

| Ex. | Starting materials | Structure | Reaction conditions | ESI-MS | HPLC retention time (method) [min] |
|---|---|---|---|---|---|
| 8.3 | X.4.A XIII.2 | 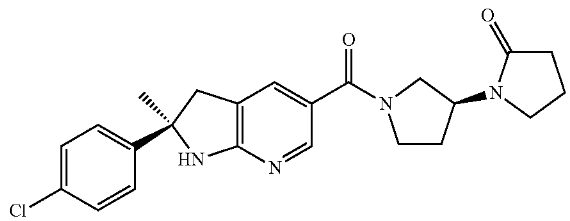 [SMILES: C[C@]1(c2ccc(Cl)cc2)Cc2cc(C(=O)N3CC[C@H](N4CCCC4=O)C3)cnc2N1] | RT 1 h | 425 [M + H]+ | 0.87 (B) |

Example 9

Example 9.1 and 9.2 (General Route)

N-[(3S)-1-[(2R)-2-(4-Chlorophenyl)-2-methyl-1H,2H,3H-pyrrolo[2,3-b]pyridine-5-carbonyl]pyrrolidin-3-yl]-N-methylacetamide and N-[(3S)-1-[(2S)-2-(4-Chlorophenyl)-2-methyl-1H,2H,3H-pyrrolo[2,3-b]pyridine-5-carbonyl]pyrrolidin-3-yl]-N-methylacetamide

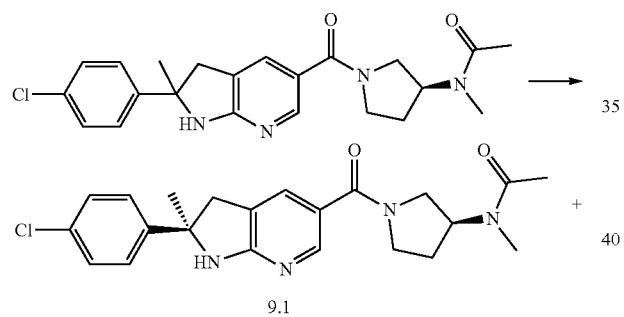

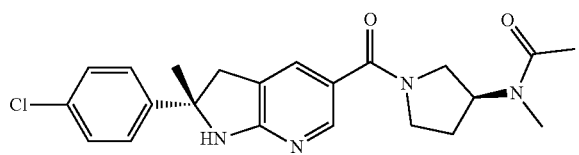

9.2

160 mg (0.39 mmol) example 8.1 are separated into its diastereoisomers by chiral SFC (method K).

Product 9.1 (First Eluting):

$C_{22}H_{25}ClN_4O_2$ (M=412.9 g/mol)

ESI-MS: 413 [M+H]+

Rt (HPLC): 4.58 min (method K)

Product 9.2 (Second Eluting):

$C_{22}H_{25}ClN_4O_2$ (M=412.9 g/mol)

ESI-MS: 413 [M+H]+

Rt (HPLC): 5.08 min (method K)

The following compounds are prepared according to the general procedure (example 9.1) described above:

| Ex. | Starting material | Structure | ESI-MS | HPLC retention time (method) [min] |
|---|---|---|---|---|
| 9.3 | XI.1 | 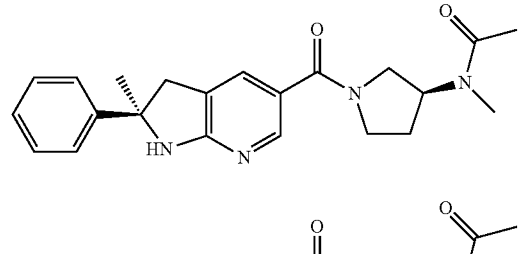 | 379 [M + H]+ | 3.51 (K) |
| 9.4 | XI.1 | 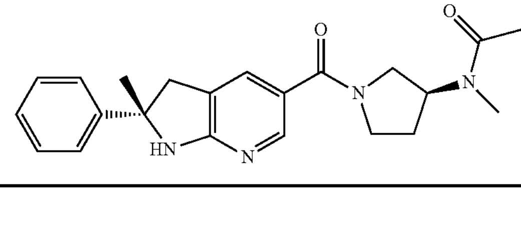 | 379 [M + H]+ | 3.99 (K) |

Example 10

N-[(3S)-1-[(2R)-2-(4-Cyanophenyl)-2-methyl-1H,2H,3H-pyrrolo[2,3-b]pyridine-5-carbonyl]pyrrolidin-3-yl]-N-methylacetamide

Example 11

Example 11.1 (General Route)

2-(7,7-Dimethyl-5,6,7,8-tetrahydro-1,8-naphthyridine-3-carbonyl)-8-oxa-2-azaspiro[4.5]decane

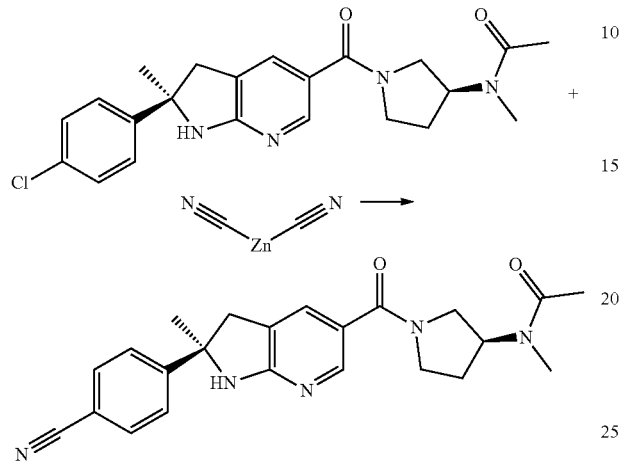

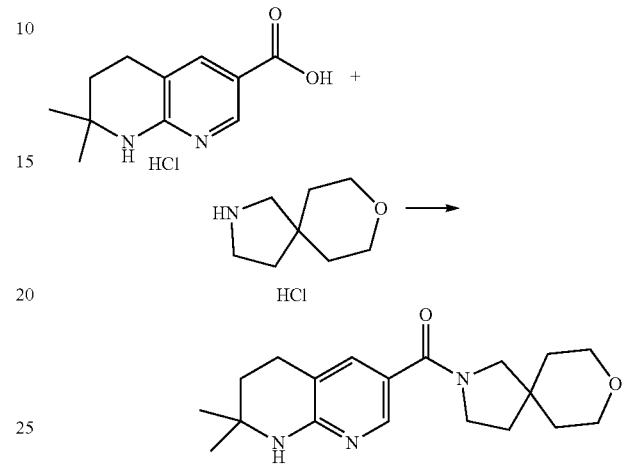

56.0 mg (0.14 mmol) example 9.1 and 31.9 mg (0.27 mmol) zinc-dicarbonitrile are dissolved in 2 mL DMF and purged with argon. Then 10.0 mg (0.014 mmol) [2-(2-aminoethyl)phenyl](chloro)palladium; dicyclohexyl[2',4',6'-tris(propan-2-yl)-[1,1'-biphenyl]-2-yl]phosphane are added and the reaction mixture is stirred at 130° C. for 20 min. The mixture is purified by HPLC (ACN/H$_2$O/NH$_4$OH) to obtain the product.

C$_{23}$H$_{25}$N$_5$O$_2$ (M=403.4 g/mol)
ESI-MS: 404 [M+H]$^+$
R$_t$ (HPLC): 0.78 min (method B)

To a mixture of 50.0 mg (0.21 mmol) intermediate III.2 and 43.9 mg (0.25 mmol) 8-oxa-2-azaspiro[4.5]decane hydrochloride in 2 mL (30.6 mmol) DMF and 106 μL (0.62 mmol) DIPEA are added 118 mg (0.31 mmol) HATU and the reaction mixture is stirred 10 minutes. The mixture is purified by HPLC (ACN/H$_2$O/NH$_4$OH) to obtain the product.

C$_{19}$H$_{27}$N$_3$O$_2$ (M=329.4 g/mol)
ESI-MS: 330 [M+H]$^+$
R$_t$ (HPLC): 0.85 min (method B)

The following compounds are prepared according to the general procedure (example 11.1) described above:

| Ex. | Starting materials | | Structure | ESI-MS | HPLC retention time (method) [min] |
|---|---|---|---|---|---|
| 11.2 | III.2 | ![](HN-azaspiro-oxane HCl) | ![structure](dimethyl-naphthyridine-carbonyl-azaspiro-oxane) | 316 [M + H]$^+$ | 0.79 (B) |
| 11.3 | III.2 | XV | ![structure](dimethyl-naphthyridine-carbonyl-pyrrolidine-pyrimidine) | 367 [M + H]$^+$ | 0.88 (B) |

-continued

| Ex. | Starting materials | | Structure | ESI-MS | HPLC retention time (method) [min] |
|---|---|---|---|---|---|
| 11.4 | XII.2 | 1-methylcyclobutanecarboxylic acid | product structure | 385 [M + H]+ | 0.92 (B) |
| 11.5 | III.2 | XIII.1 | product structure | 345 [M + H]+ | 0.75 (B) |
| 11.6 | III.2 | XVI | product structure | 331 [M + H]+ | 0.76 (B) |
| 11.7 | XII.2 | 1-cyanocyclopropanecarboxylic acid | product structure | 382 [M + H]+ | 0.82 (B) |
| 11.8 | III.2 | XIII.2 | product structure | 343 [M + H]+ | 0.77 (B) |
| 11.9 | XII.2 | cyclopropanecarboxylic acid | product structure | 357 [M + H]+ | 0.82 (B) |
| 11.10 | XII.2 | cyclobutanecarboxylic acid | product structure | 371 [M + H]+ | 0.85 (B) |
| 11.11 | XII.2 | 3,3-difluorocyclobutanecarboxylic acid | product structure | 407 [M + H]+ | 0.86 (B) |

-continued

| Ex. | Starting materials | Structure | ESI-MS | HPLC retention time (method) [min] |
|---|---|---|---|---|
| 11.12† | III.3 XVI | 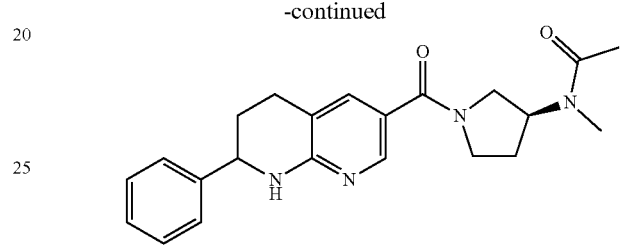 | 345 [M + H]⁺ | 0.80 (B) |

†Reaction time 60 min at RT

Example 12

Example 12.1 (General Route)

N-Methyl-N-[(3S)-1-(7-phenyl-5,6,7,8-tetrahydro-1,8-naphthyridine-3-carbonyl)pyrrolidin-3-yl]acetamide

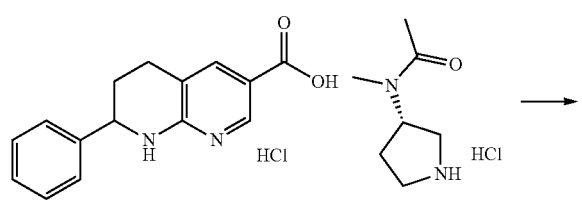

To a mixture of 48.0 mg (0.17 mmol) intermediate XXI.1 and 35.4 mg (0.20 mmol) intermediate XVI in 1 mL DMF and 0.17 mL (0.99 mmol) DIPEA are added 69.1 mg (0.18 mmol) HATU and the reaction mixture is stirred at RT for 10 minutes. The mixture is purified by HPLC (ACN/H$_2$O/NH$_4$OH) to obtain the product.

$C_{22}H_{26}N_4O_2$ (M=378.4 g/mol)

ESI-MS: 379 [M+H]⁺

R$_t$ (HPLC): 0.85 min (method B)

The following compounds are prepared according to the general procedure (example 12.1) described above:

| Ex. | Starting materials | Structure | ESI-MS | HPLC retention time (method) [min] |
|---|---|---|---|---|
| 12.2 | XXI.2 XVI | 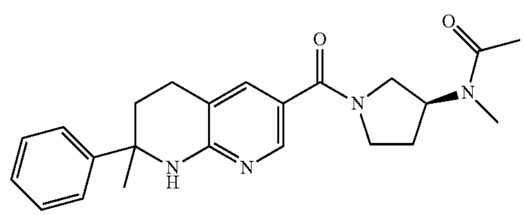 [SMILES: CC(=O)N(C)[C@H]1CCN(C(=O)c2cnc3c(c2)CCC(C)(c2ccccc2)N3)C1] | 393 [M + H]⁺ | 0.73 (A) |
| 12.3 | III.4 XVI | 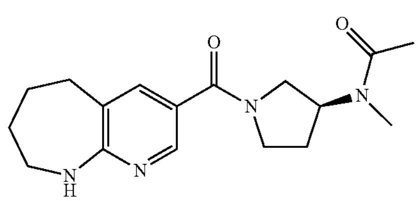 [SMILES: CC(=O)N(C)[C@H]1CCN(C(=O)c2cnc3c(c2)CCCCN3)C1] | 317 [M + H]⁺ | 0.45 (L) |

-continued

| Ex. | Starting materials | Structure | ESI-MS | HPLC retention time (method) [min] |
|---|---|---|---|---|
| 12.4 | XXI.4 XVI | 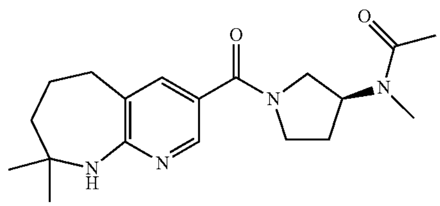 [SMILES: CC(=O)N(C)[C@H]1CCN(C(=O)c2cnc3c(c2)CCCC(C)(C)N3)C1] | 345 [M + H]+ | 0.80 (B) |
| 12.5 | XXI.4 XIII.2 | 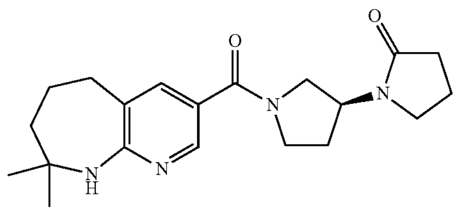 [SMILES: CC1(C)CCCc2cc(C(=O)N3CC[C@H](N4CCCC4=O)C3)cnc2N1] | 357 [M + H]+ | 0.81 (B) |
| 12.6 | XXI.4 XXV | 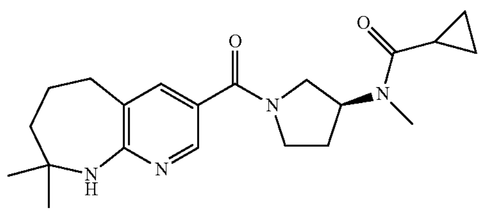 [SMILES: CN(C(=O)C1CC1)[C@H]1CCN(C(=O)c2cnc3c(c2)CCCC(C)(C)N3)C1] | 371 [M + H]+ | 0.87 (B) |
| 12.7 | XXI.4 XIII.1 | 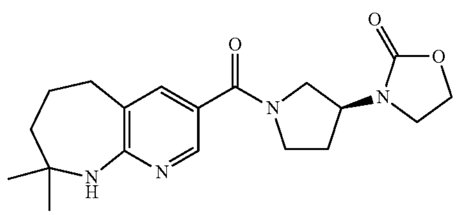 [SMILES: CC1(C)CCCc2cc(C(=O)N3CC[C@H](N4CCOC4=O)C3)cnc2N1] | 359 [M + H]+ | 0.80 (B) |

Example 13

Example 13.1 and 13.2 (General Route)

N-methyl-N-[(3S)-1-[(7R)-7-Methyl-7-(pyrimidin-5-yl)-5,6,7,8-tetrahydro-1,8-naphthyridine-3-carbonyl]pyrrolidin-3-yl]cyclobutanecarboxamide and N-methyl-N-[(3S)-1-[(7S)-7-Methyl-7-(pyrimidin-5-yl)-5,6,7,8-tetrahydro-1,8-naphthyridine-3-carbonyl]pyrrolidin-3-yl]cyclobutanecarboxamide

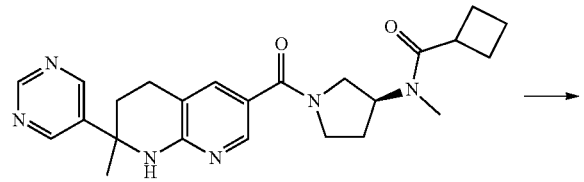

→

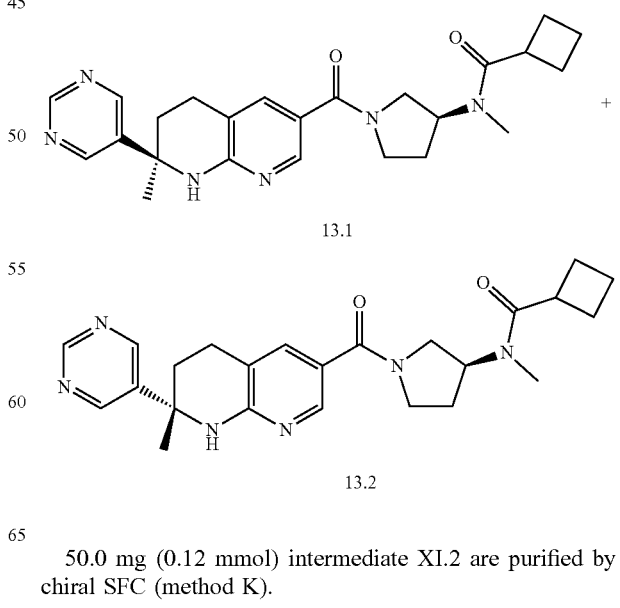

50.0 mg (0.12 mmol) intermediate XI.2 are purified by chiral SFC (method K).

Example 13.1 (First Eluting)

$C_{24}H_{30}N_6O_2$ (M=434.5 g/mol)
ESI-MS: 435 [M+H]+
Rt (HPLC): 4.52 min (method K)

Example 13.2 (Second Eluting)

$C_{24}H_{30}N_6O_2$ (M=434.5 g/mol)
ESI-MS: 435 [M+H]+
Rt (HPLC): 5.09 min (method K)

The following compounds are prepared according to the general procedure (example 13.1 and 13.2) described above:

| Ex. | Starting material | Structure | ESI-MS | HPLC retention time (method) [min] |
|---|---|---|---|---|
| 13.3 | XI.3 | (structure) | 421 [M + H]+ | 2.98 (J) |
| 13.4 | XI.3 | (structure) | 421 [M + H]+ | 3.76 (J) |

Analytical HPLC Methods

Method A

| Gradient/ Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Column: Sunfire C18_3.0 × 30 mm_2.5 µm

Method B

| Gradient/ Solvent Time [min] | % Sol [Water 0.1% NH₃] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Column: XBridge C18_3.0 × 30 mm_2.5 µm

Method C

| Gradient/ Solvent Time [min] | % Sol [scCO2] | % Sol [MeOH 20 mM NH3] | Flow [ml/min] | Temp [° C.] | Back pressure [PSI] |
|---|---|---|---|---|---|
| 0.0 | 90.0 | 10.0 | 4.0 | 40.0 | 2175.0 |
| 10.0 | 90.0 | 10.0 | 4.0 | 40.0 | 2175.0 |

Column: Lux ® Cellulose-4_4.6 × 250 mm_5 µm
For preparative scale: Lux ® Cellulose-4_21.2 × 250 mm_5 µm; Flow 60 mL/min

Method D

| Gradient/ Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

Column: Lux ® Amylose-2_4.6 × 250 mm_5 µm
For preparative scale: Lux ® Amylose-2_21.2 × 250 mm_5 µm; Flow 60 mL/min

Method E

| Gradient/ Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 80.0 | 20.0 | 4.0 | 40.0 | 2175.0 |
| 10.0 | 80.0 | 20.0 | 4.0 | 40.0 | 2175.0 |

Column: CHIRAL ART ® Amylose SA_4.6 × 250 mm_5 µm
For preparative scale: CHIRAL ART ® Amylose SA_20 × 250 mm_5 µm; Flow 80 mL/min

Method F

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Column: CHIRAL ART ® Amylose SA_4.6 × 250 mm_5 μm
For preparative scale: CHIRAL ART ® Amylose SA_20 × 250 mm_5 μm; Flow 60 mL/min

Method G

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 60.0 | 40.0 | 4.0 | 40.0 | 2175.0 |
| 10.0 | 60.0 | 40.0 | 4.0 | 40.0 | 2175.0 |

Column: CHIRAL ART ® Amylose SA_4.6 × 250 mm_5 μm

Method H

| Gradient/Solvent Time [min] | % Sol [Water 0.1% FA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Column: Sunfire C18_3.0 × 30 mm_2.5 μm

Method I

| Gradient/Solvent Time [min] | % Sol [Water 0.1% TFA (v/v)] | % Sol [Acetonitrile] | Flow [ml/min] | Temp [° C.] |
|---|---|---|---|---|
| 0.0 | 97.0 | 3.0 | 2.2 | 60.0 |
| 0.2 | 97.0 | 3.0 | 2.2 | 60.0 |
| 1.2 | 0.0 | 100.0 | 2.2 | 60.0 |
| 1.25 | 0.0 | 100.0 | 3.0 | 60.0 |
| 1.4 | 0.0 | 100.0 | 3.0 | 60.0 |

Column: Zorbax StableBond C18_3.0 × 30 mm_1.8 μm

Method J

| Gradient/Solvent Time [min] | % Sol [scCO2] | % Sol [IPA 20 mM NH3] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Column: Lux ® Cellulose-3_4.6 × 250 mm_5 μm
For preparative scale: Lux ® Cellulose-3_10 × 250 mm_5 μm; Flow 10 mL/min

Method K

| Gradient/Solvent Time [min] | % Sol [scCO2] | % Sol [MEOH 20 mM NH3] | Flow [ml/min] | Temp [° C.] | Back pressure [PSI] |
|---|---|---|---|---|---|
| 0.0 | 75.0 | 25.0 | 4.0 | 40.0 | 2175.0 |
| 10.0 | 75.0 | 25.0 | 4.0 | 40.0 | 2175.0 |

Column: CHIRAL ART ® Cellulose SB_4.6 × 250 mm_5 μm
For preparative scale: CHIRAL ART ® Cellulose-SB_20 × 250 mm_5 μm; Flow 60 mL/min

Method L

| Gradient/Solvent Time [min] | % Sol [Water 0.1% NH3] | % Sol [Acetonitrile] | Flow [ml/min] | Temp [° C.] |
|---|---|---|---|---|
| 0.0 | 95.0 | 5.0 | 1.5 | 60.0 |
| 1.3 | 0.0 | 100.0 | 1.5 | 60.0 |
| 1.5 | 0.0 | 100.0 | 1.5 | 60.0 |
| 1.6 | 95.0 | 5.0 | 1.5 | 60.0 |

Column: XBridge C18_3.0 × 30 mm_2.5 μm

Description of Biological Properties
Vanin-1 Enzymatic Assay:

The test compounds are dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions are prepared, a further intermediate dilutions of the substances is carried out with assay buffer resulting in 1% final DMSO concentration in the assay.

0.1 nM of FLAG-tagged Vanin-1 (AA 22-493, T26I, produced internally) and test compounds are incubated at room temperature for 20 minutes in assay buffer (1 mM DTT, 0.0025% Brij-35, 50 mM HEPES, pH7.5). D-Pantethine (Sigma, Cat #P2125-5G) in assay buffer is added (final concentration 3 μM) and incubated for additional 30 minutes at room temperature. Total assay volume typically is 40 μl but might be adjusted according to needs. Reaction is stopped by adding equal volume of stop solution as the reaction mixture to reach 100 nM HD-pantothenic acid (as an internal standard) and 1% TFA. Assay plates are centrifuged for 2 minutes and the formation of pantothenic acid is detected by RapidFire Mass Spectrometry (mobile phase A: 0.1% formic acid and 0.01% trifluoroacetic acid in water; mobile phase B: 47.5% acetonitrile, 47.5% methanol, 0.1% formic acid and 0.01% trifluoroacetic acid in water) using a C18, 12 μL cartridge (Agilent Cat #G9205A).

The values given in Table I result from measurements of one or more samples. In case of multiple measurements the geometric mean values are given.

Human Whole Blood assay: Pantetheinase (vanin) converts panteheine into pantothenic acid and cysteamine. Accordingly, in the described protocol vanin activity is quantified by formation of pantothenic acid after pantetheine supplementation via pantethine. The assay is applicable to identify vanin inhibitors. Compound stocks were dissolved in DMSO at 10 mM. Further dilutions were performed in RPMI 1640 medium (Gibco, #A-10491-01) and final concentrations in the assay were 0.032 nM-500 nM.

Human blood was drawn into a blood bag (1% heparin, 50 I.E./mL). Blood was aliquoted into cavities of 96-deep-well plates at 290 µL and mixed with 10 µL compound solution or vehicle (30 sec at 1400 rpm on a shaker). Equilibration followed at room temperature, 250 rpm and for 30 min. The assay was started by adding 10 µL of substrate solution (20 µM pantethine in 1 mM DTT, 0.0025% Brij-35, 50 mM HEPES, pH7.5) to each well, except for some blank wells which received 10 mL substrate buffer (1 mM DTT, 0.0025% Brij-35, 50 mM HEPES, pH7.5) only. Samples were thoroughly shaken (30 sec, 1400 rpm) and reaction was allowed to take place at room temperature, 250 rpm and for 5 min. The reaction was stopped by addition of a vanin tool inhibitor in excess (BI-1 total conc. 10 µM). Centrifugation of the plate followed at 4° C., 665 G for 10 min. Then the blood plasma samples (100 µL) were transferred into another 96-deep-well plate and proteins were precipitated (5 min on ice) by adding 100 µL of ice cold precipitation solution (1 µM labelled pantothenic acid (di-β-alanine-13C6,15N2 calcium salt, Sigma, #705837) in acetonitrile). Afterwards the plate was centrifuged (4° C., 3220 G, 10 min) and supernatants (50 µL) were collected into another 96-deep-well plate and mixed (10 sec, 1400 rpm) with 150 µL ice cold formic acid (0.1%, Carl Roth GmbH+Co.KG, #CP03.1). The formation of pantothenic acid is detected by RapidFire Mass Spectrometry. A TripleQuad 6500+ (AB-Sciex, Germany) was equipped with an LC-1290 system, a RapidFire autosampler (Agilent, Germany) and a C18 cartridge Type C 12 µL (Agilent Cat #G9526-80000). Mobile phase A was consisting of 0.09% formic acid and 0.01% trifluoroacetic acid in water and mobile phase B of 0.09% formic acid and 0.01% trifluoroacetic acid in acetonitrile/methanol/water=47.5/47.5/5.

Synthesis of Tool Inhibitor BI-1:

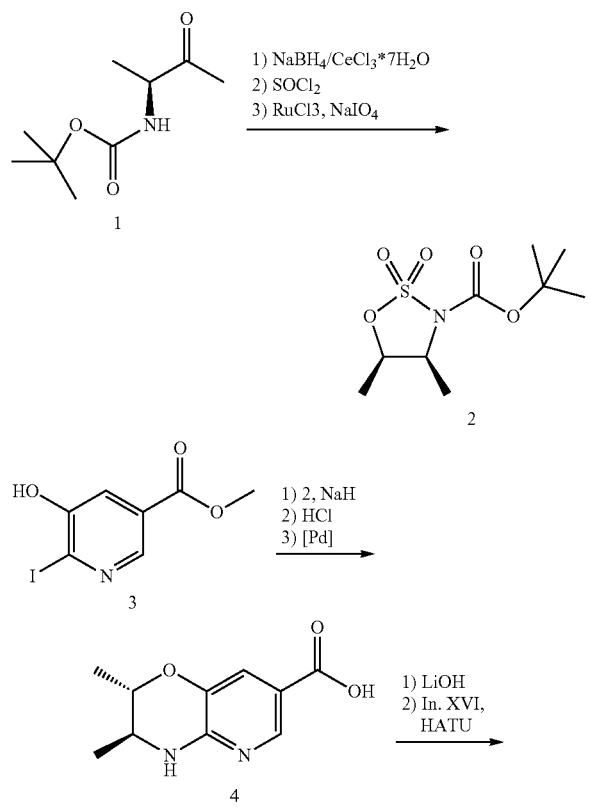

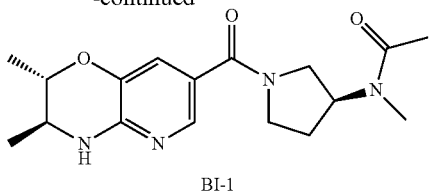

To 70 mL MeOH are added 5.40 g (28.8 mmol) ketone 1 (synthesis described in *Angew. Chem. Int. Ed.* 2010, 49, 6856) and 12.9 g (34.6 mmol) CeCl$_3$*7 H$_2$O. The reaction mixture is cooled to −15° C. before 2.18 g (57.7 mmol) NaBH$_4$ are added portion wise. The reaction mixture is stirred for 3 h at 0° C. The reaction is quenched by the addition of saturated aq. NH$_4$Cl solution and extracted with EtOAc. The organic layers are combined, dried over Na$_2$SO$_4$ and the solvent is removed in vacuo.

A stirred solution of 6.29 g (52.8 mmol) thionyl chloride in 50 mL acetonitrile is cooled to the −50° C. and a solution of 4 g (21.1 mmol) in ACN of the above mentioned product is added drop wise. When addition completed then 258 mg (2.11 mmol) DMAP are added in one portion. The mixture is stirred for 15 min, keeping temperature below −40° C., and then 8.36 g (106 mmol) dry pyridine are added, keeping external temperature at −40° C. Stirring is continued for 1 h. EtOAc is added, stirred for 5 mins, suspension appeared (pyridine salt) which was filtered and washed with EtOAc. To the filtrate is added 12 mL saturated Na$_2$HPO$_4$ slowly. The resulting solution is stirred for 40 mins. Two layers were separated. The organic layer is washed with 10 mL 1M NaHSO$_4$ aqueous, dried over Na$_2$SO$_4$ and concentrated under reduced pressure. The crude compound is purified by column chromatography (silica gel, 8% EtOAc in hexane).

C$_9$H$_{17}$NO$_4$S (M=235.3 g/mol)
ESI-MS: 258 [M+Na]$^+$
R$_f$ (TLC, silica gel) 0.4 (PE/EtOAc 3/1)

To a solution of 1.00 g (0.004 mol) of the above described product in 10,000 ml EtOAc are added 1.36 g (0.006 mol) NaIO$_4$ in 10 mL H$_2$O Then 44 mg (0.2 mmol) RuCl$_3$ are added and the mixture is stirred at 0 to 15° C. for 12 h. The mixture is quenched with H$_2$O (20 mL) and extracted with EtOAc. Then the organic phase is washed with brine (20 mL), dried over Na$_2$SO$_4$, filtered and concentrated to dryness. The residue is purified by column chromatography (silica gel, PE/EtOAc=10:1 to 3:1).

C$_9$H$_{17}$NO$_5$S (M=251.3 g/mol)
ESI-MS: 252 [M+H]$^+$
Rf (TLC, silica gel) 0.55 (PE/EtOAc 3/1)

4.00 g (14.3 mmol) methyl 5-hydroxy-6-iodopyridine-3-carboxylate are added to 40 ml of DMF. To this are added 602 mg (15.1 mmol) sodium hydride. After gas evolution, 5.40 g (21.5 mmol) are added and the reaction mixture is stirred at 75 C for 1.5 h. After cooling down to RT, the reaction mixture is diluted with EtOAc and rinsed with water. The organics were dried, filtered, and evaporated.

The residue is purified by column chromatography (silica gel, 0-5% MeOH/CH$_2$Cl$_2$).

C$_{16}$H$_{23}$IN$_2$O$_5$ (M=450.3 g/mol)
ESI-MS: 451 [M+H]$^+$ 5.00 g (11.1 mmol) of the above mentioned product are added to in 50 ml of MeOH and 10 ml of CH$_2$Cl$_2$. To this are added 50 ml of 4 M HCl in dioxane. After 3 h the volatiles are removed in vauo and the residue used without further purification.

3.28 g (9.37 mmol) of the above mentioned product, 105 mg (0.47 mmol) Pd(OAc)$_2$, 0.33 g (0.56 mmol), 9,9-dimethyl-4,5-bis(diphenylphosphino)xanthene (0.33 g; 0.56 mmol; 6.00 mol %) and 9.16 g (28.1 mmol) cesium carbonate are added to 100 ml dioxane and the mixture is degassed thoroughly. The reaction mixture is stirred at 90° C. under argon for 4 h. The solids are filtered through a plug of Celite® and evaporated. The residue is purified by column chromatography (silica gel,0-5% MeOH/CH$_2$Cl$_2$).

1.50 g (6.75 mmol) of the above mentioned product are added to 5 ml of MeOH and 70 ml of water. To this are added 323 mg (13.5 mmol) LiOH and the reaction mixture is stirred at 50° C. for 1 h. The reaction is filtered and the MeOH is removed in vacuo. The aqueous layer is neutralized with 1 M HCl. The solids are filtered and allowed to dry and used without further purification. C$_{10}$H$_{12}$N$_2$O$_3$ (M=208.2 g/mol)

ESI-MS: 209 [M+H]$^+$
Rt (HPLC): 0.60 min (method A)

915 mg (4.39 mmol) of the above mentioned product are dissolved in 20 ml of DMF. To this are added 0.86 g (4.83 mmol) of intermediate XVI and 1.84 ml (13.2 mmol) TEA) followed by 1.84 g (4.83 mmol) HATU. The reaction mixture is stirred at RT for 16 h.

Volatiles are removed in vacuo and the residue is purified by column chromatography (Biotage KP-Nh cartridge, 0-10% MeOH/EtOAc).
C$_{17}$H$_{24}$N$_4$O$_3$ (M=332.4 g/mol)
ESI-MS: 333 [M+H]$^+$
Rt (HPLC): 0.63 min (method A)

Other features and advantages of the present invention will become apparent from the following more detailed Examples which illustrate, by way of example, the principles of the invention

TABLE I

Biological properties of representatives of the present invention

| Ex. | Structure | VNN 1 IC$_{50}$ (nM) | HWB IC$_{50}$ (nM) |
|---|---|---|---|
| 1.1 | 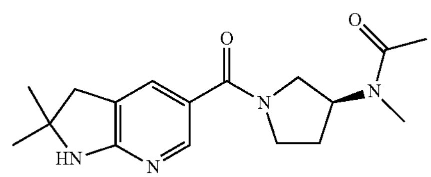 [SMILES: CC(=O)N(C)[C@H]1CCN(C(=O)c2cnc3c(c2)CC(C)(C)N3)C1] | 2.5 | |
| 1.2 | 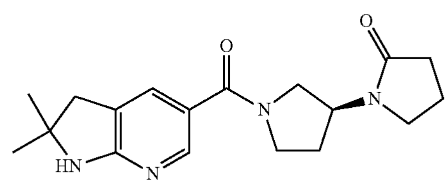 [SMILES: CC1(C)Cc2cc(C(=O)N3CC[C@H](N4CCCC4=O)C3)cnc2N1] | 1.5 | 11.5 |
| 1.3 | 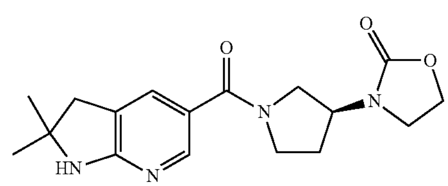 [SMILES: CC1(C)Cc2cc(C(=O)N3CC[C@H](N4CCOC4=O)C3)cnc2N1] | 1.6 | |
| 1.4 | 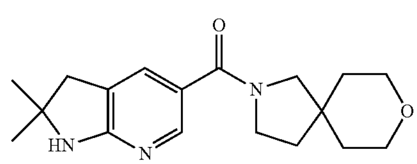 [SMILES: CC1(C)Cc2cc(C(=O)N3CCC4(CCOCC4)C3)cnc2N1] | 4.9 | |
| 1.5 | 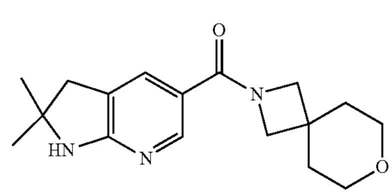 [SMILES: CC1(C)Cc2cc(C(=O)N3CC4(CCOCC4)C3)cnc2N1] | 10.4 | |

TABLE I-continued

Biological properties of representatives of the present invention

| Ex. | Structure | VNN 1 IC$_{50}$ (nM) | HWB IC$_{50}$ (nM) |
|---|---|---|---|
| 2.1 | 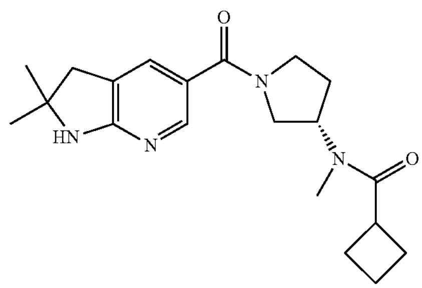 [SMILES: CN(C(=O)C1CCC1)[C@H]1CCN(C(=O)c2cnc3c(c2)CC(C)(C)N3)C1] | 0.9 | 2.5 |
| 2.2 | 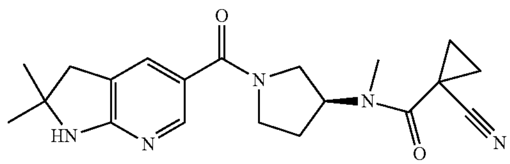 [SMILES: CN(C(=O)C1(C#N)CC1)[C@H]1CCN(C(=O)c2cnc3c(c2)CC(C)(C)N3)C1] | 1.1 | 9.5 |
| 2.3 | 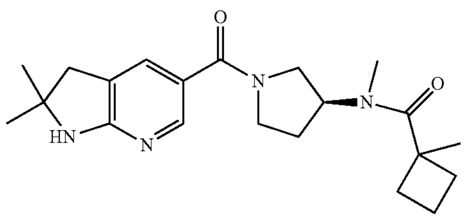 | 4.6 | |
| 2.4 | 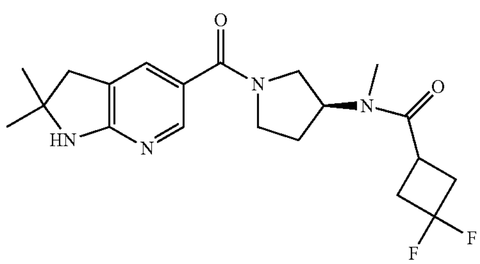 [SMILES: CN(C(=O)C1CC(F)(F)C1)[C@H]1CCN(C(=O)c2cnc3c(c2)CC(C)(C)N3)C1] | 0.6 | 2.8 |
| 2.5 | 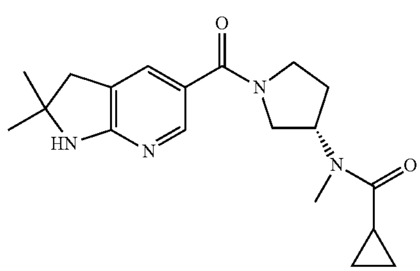 [SMILES: CN(C(=O)C1CC1)[C@H]1CCN(C(=O)c2cnc3c(c2)CC(C)(C)N3)C1] | 2.1 | |
| 3.1 | 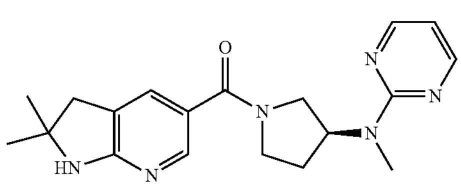 [SMILES: CN(c1ncccn1)[C@H]1CCN(C(=O)c2cnc3c(c2)CC(C)(C)N3)C1] | 2.3 | 38.0 |

TABLE I-continued

Biological properties of representatives of the present invention

| Ex. | Structure | VNN 1 IC$_{50}$ (nM) | HWB IC$_{50}$ (nM) |
|---|---|---|---|
| 4.1 | 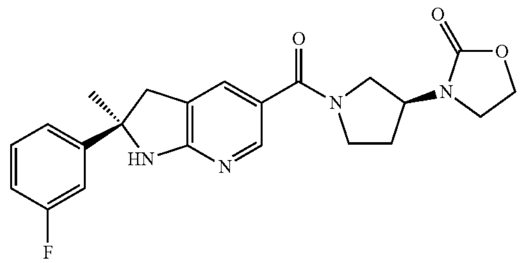 | 0.1 | 1.4 |
| 4.2 | 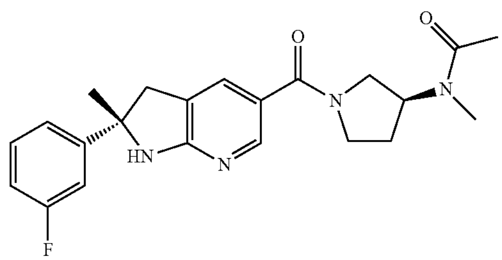 | 1.7 | |
| 4.3 | 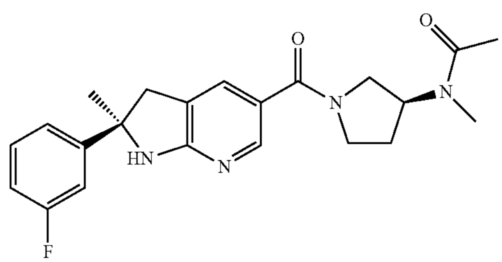 | 0.1 | 1.4 |
| 4.4 | 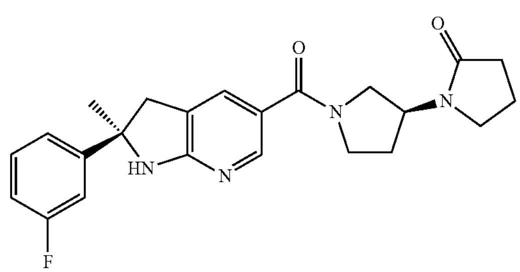 [SMILES: C[C@]1(c2cccc(F)c2)Cc2cc(C(=O)N3CC[C@H](N4CCCC4=O)C3)cnc2N1] | 0.1 | 2.1 |
| 5.1 | 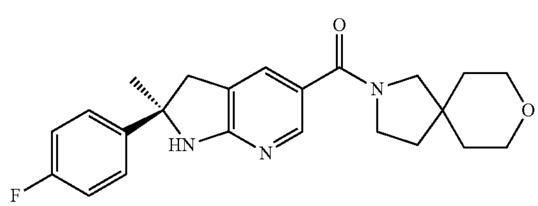 [SMILES: C[C@]1(c2ccc(F)cc2)Cc2cc(C(=O)N3CCC4(CCOCC4)C3)cnc2N1] | 0.4 | 3.6 |
| 5.2 | 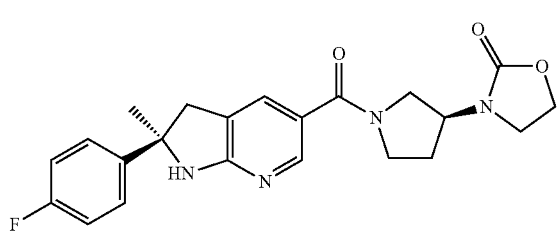 [SMILES: C[C@]1(c2ccc(F)cc2)Cc2cc(C(=O)N3CC[C@H](N4CCOC4=O)C3)cnc2N1] | 0.1 | 1.5 |

TABLE I-continued
Biological properties of representatives of the present invention
| Ex. | Structure | VNN 1 IC$_{50}$ (nM) | HWB IC$_{50}$ (nM) |
|---|---|---|---|
| 5.3 | 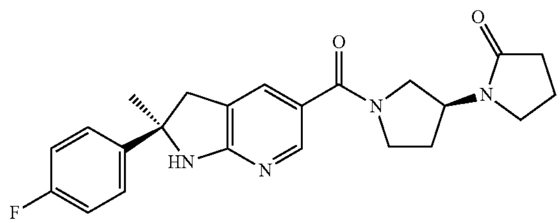 [SMILES: C[C@]1(c2ccc(F)cc2)Cc2cc(C(=O)N3CC[C@H](N4CCCC4=O)C3)cnc2N1] | 0.1 | 1.5 |
| 5.4 | 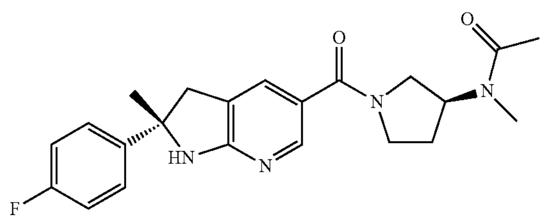 [SMILES: CC(=O)N(C)[C@H]1CCN(C(=O)c2cnc3c(c2)C[C@@](C)(c2ccc(F)cc2)N3)C1] | 87.1 | |
| 5.5 | 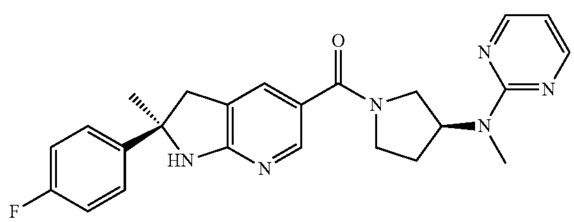 [SMILES: CN(c1ncccn1)[C@H]1CCN(C(=O)c2cnc3c(c2)C[C@](C)(c2ccc(F)cc2)N3)C1] | 0.2 | 17.2 |
| 5.6 | 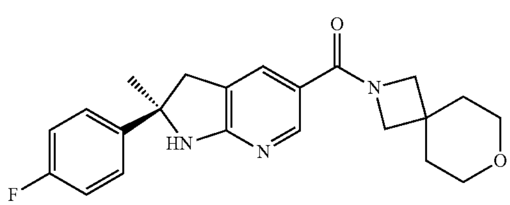 [SMILES: C[C@]1(c2ccc(F)cc2)Cc2cc(C(=O)N3CC4(CCOCC4)C3)cnc2N1] | 0.6 | 10.3 |
| 6 | 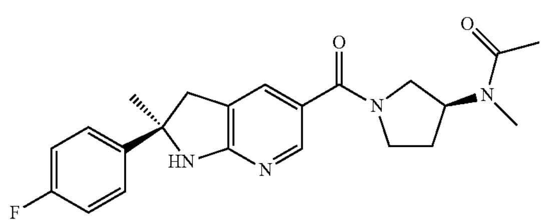 [SMILES: CC(=O)N(C)[C@H]1CCN(C(=O)c2cnc3c(c2)C[C@](C)(c2ccc(F)cc2)N3)C1] | 0.2 | 1.9 |
| 7.1 | 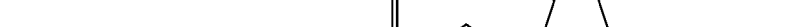 | 0.1 | |

TABLE I-continued

Biological properties of representatives of the present invention

| Ex. | Structure | VNN 1 IC$_{50}$ (nM) | HWB IC$_{50}$ (nM) |
|---|---|---|---|
| 7.2 | 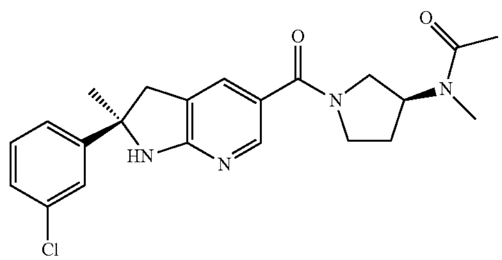 [SMILES: CC(=O)N(C)[C@H]1CCN(C(=O)c2cnc3c(c2)C[C@](C)(c2cccc(Cl)c2)N3)C1] | 0.1 | 2.0 |
| 7.3 | 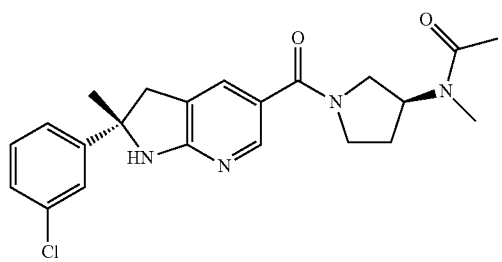 [SMILES: CC(=O)N(C)[C@H]1CCN(C(=O)c2cnc3c(c2)C[C@@](C)(c2cccc(Cl)c2)N3)C1] | 18.9 | 424.0 |
| 7.4 | 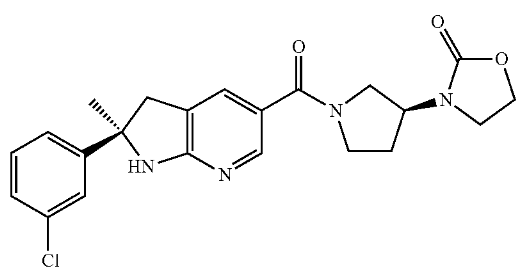 [SMILES: C[C@]1(c2cccc(Cl)c2)Cc2cc(C(=O)N3CC[C@H](N4CCOC4=O)C3)cnc2N1] | 0.1 | 1.9 |
| 8.1 | 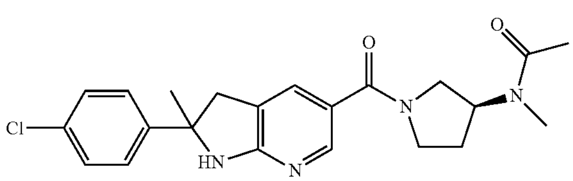 [SMILES: CC(=O)N(C)[C@H]1CCN(C(=O)c2cnc3c(c2)CC(C)(c2ccc(Cl)cc2)N3)C1] | 0.2 | 4.3 |
| 8.2 | 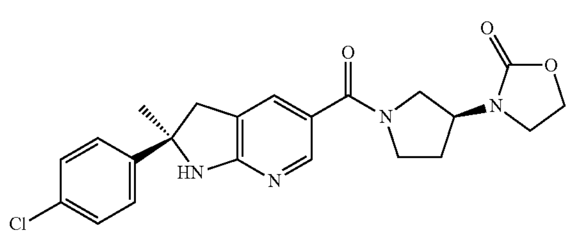 [SMILES: C[C@]1(c2ccc(Cl)cc2)Cc2cc(C(=O)N3CC[C@H](N4CCOC4=O)C3)cnc2N1] | 0.1 | 2.6 |
| 8.3 | 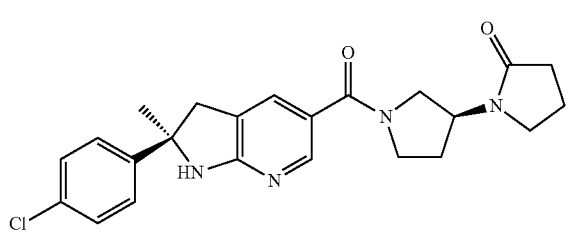 [SMILES: C[C@]1(c2ccc(Cl)cc2)Cc2cc(C(=O)N3CC[C@H](N4CCCC4=O)C3)cnc2N1] | 0.1 | 3.8 |

TABLE I-continued

Biological properties of representatives of the present invention

| Ex. | Structure | VNN 1 IC$_{50}$ (nM) | HWB IC$_{50}$ (nM) |
|---|---|---|---|
| 9.1 | 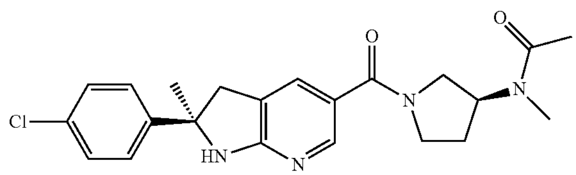 [SMILES: CC(=O)N(C)[C@H]1CCN(C(=O)c2cnc3c(c2)C[C@](C)(c2ccc(Cl)cc2)N3)C1] | 0.1 | 3.0 |
| 9.2 | 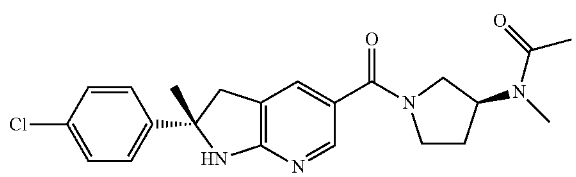 [SMILES: CC(=O)N(C)[C@H]1CCN(C(=O)c2cnc3c(c2)C[C@@](C)(c2ccc(Cl)cc2)N3)C1] | 1.4 | |
| 9.3 | 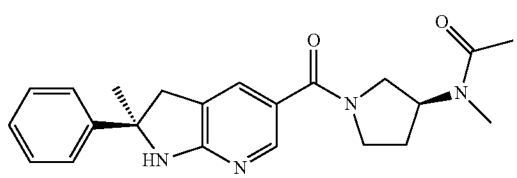 | 0.2 | 2.1 |
| 9.4 | 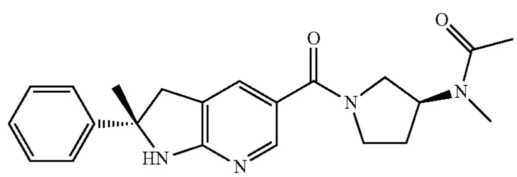 [SMILES: CC(=O)N(C)[C@H]1CCN(C(=O)c2cnc3c(c2)C[C@@](C)(c2ccccc2)N3)C1] | 25.9 | |
| 10 | 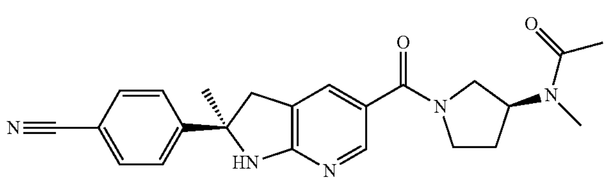 [SMILES: CC(=O)N(C)[C@H]1CCN(C(=O)c2cnc3c(c2)C[C@](C)(c2ccc(C#N)cc2)N3)C1] | 0.2 | |
| 11.1 | 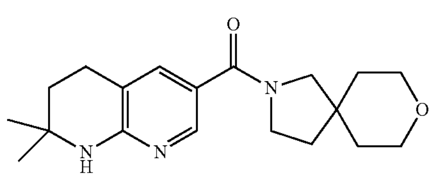 [SMILES: CC1(C)CCc2cc(C(=O)N3CCC4(CCOCC4)C3)cnc2N1] | 1.7 | |
| 11.2 | 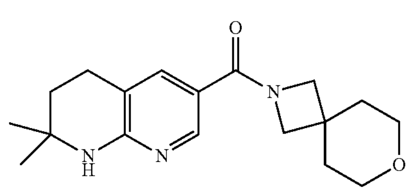 [SMILES: CC1(C)CCc2cc(C(=O)N3CC4(CCOCC4)C3)cnc2N1] | 0.3 | 4.5 |
| 11.3 | 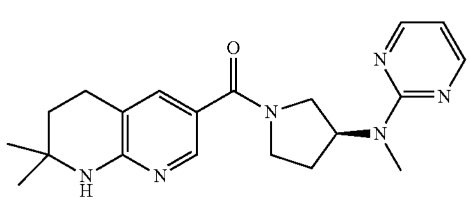 [SMILES: CN(c1ncccn1)[C@H]1CCN(C(=O)c2cnc3c(c2)CCC(C)(C)N3)C1] | 0.2 | 2.9 |

TABLE I-continued

Biological properties of representatives of the present invention

| Ex. | Structure | VNN 1 IC$_{50}$ (nM) | HWB IC$_{50}$ (nM) |
|---|---|---|---|
| 11.4 | 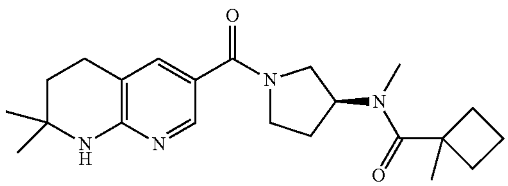 [SMILES: CN(C(=O)C1(C)CCC1)[C@H]1CCN(C(=O)c2cnc3c(c2)CCC(C)(C)N3)C1] | 0.9 | 11.4 |
| 11.5 | 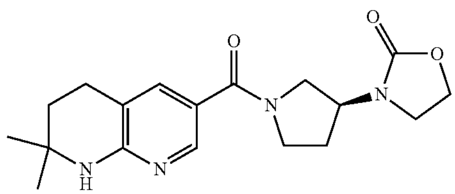 [SMILES: CC1(C)CCc2cc(C(=O)N3CC[C@H](N4CCOC4=O)C3)cnc2N1] | 4.3 | |
| 11.6 | 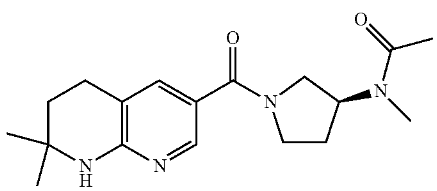 [SMILES: CC(=O)N(C)[C@H]1CCN(C(=O)c2cnc3c(c2)CCC(C)(C)N3)C1] | 0.5 | 12.6 |
| 11.7 | 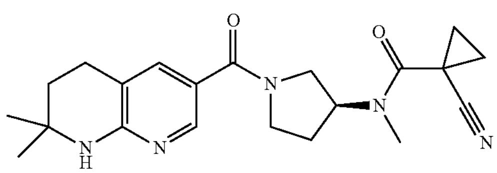 [SMILES: CN(C(=O)C1(C#N)CC1)[C@H]1CCN(C(=O)c2cnc3c(c2)CCC(C)(C)N3)C1] | 4.9 | |
| 11.8 | 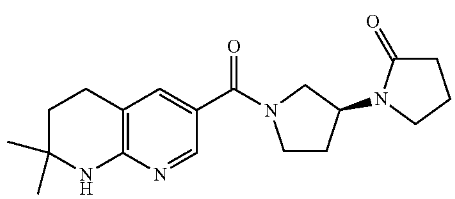 [SMILES: CC1(C)CCc2cc(C(=O)N3CC[C@H](N4CCCC4=O)C3)cnc2N1] | 0.7 | 5.2 |
| 11.9 | 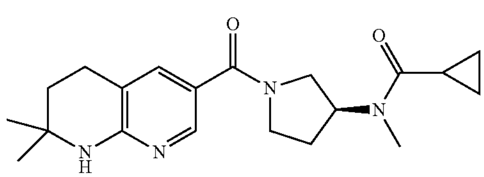 [SMILES: CN(C(=O)C1CC1)[C@H]1CCN(C(=O)c2cnc3c(c2)CCC(C)(C)N3)C1] | 0.7 | 3.5 |
| 11.10 | 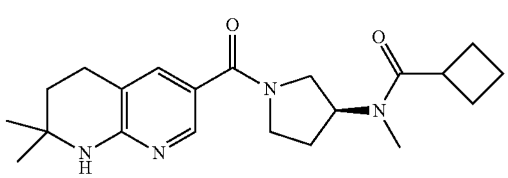 [SMILES: CN(C(=O)C1CCC1)[C@H]1CCN(C(=O)c2cnc3c(c2)CCC(C)(C)N3)C1] | 0.6 | 10.6 |
| 11.11 | 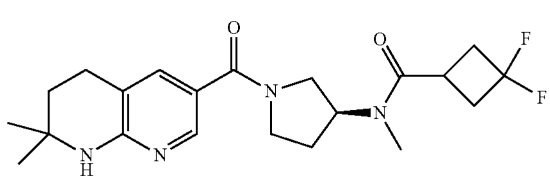 [SMILES: CN(C(=O)C1CC(F)(F)C1)[C@H]1CCN(C(=O)c2cnc3c(c2)CCC(C)(C)N3)C1] | 0.5 | 6.9 |

TABLE I-continued

Biological properties of representatives of the present invention

| Ex. | Structure | VNN 1 IC$_{50}$ (nM) | HWB IC$_{50}$ (nM) |
|---|---|---|---|
| 11.12 | 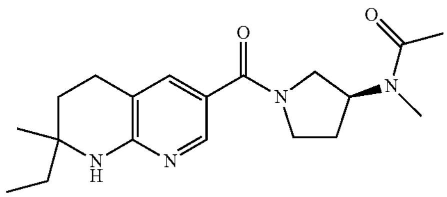 [SMILES: CCC1(C)CCc2cc(C(=O)N3CC[C@H](N(C)C(C)=O)C3)cnc2N1] | 0.5 | 5.7 |
| 12.1 | 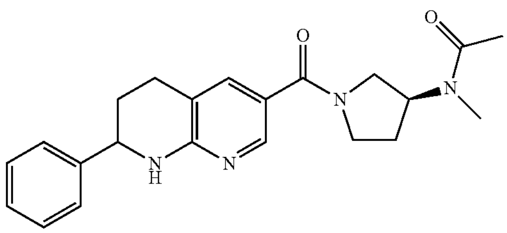 [SMILES: CC(=O)N(C)[C@H]1CCN(C(=O)c2cnc3c(c2)CCC(c2ccccc2)N3)C1] | 20.3 | |
| 12.2 | 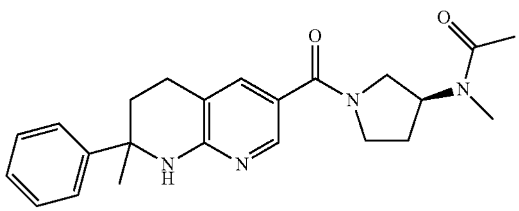 [SMILES: CC(=O)N(C)[C@H]1CCN(C(=O)c2cnc3c(c2)CCC(C)(c2ccccc2)N3)C1] | 0.3 | 8.2 |
| 12.3 | 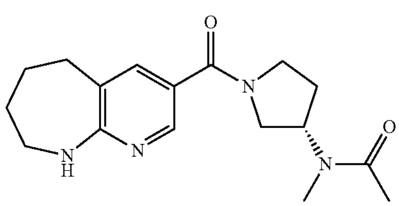 [SMILES: CC(=O)N(C)[C@H]1CCN(C(=O)c2cnc3c(c2)CCCCN3)C1] | 0.4 | |
| 12.4 | 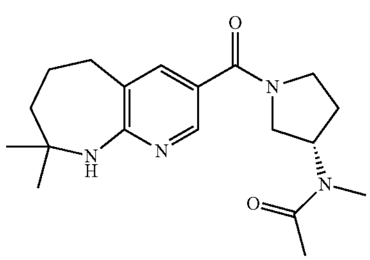 | 2.5 | |
| 12.5 | 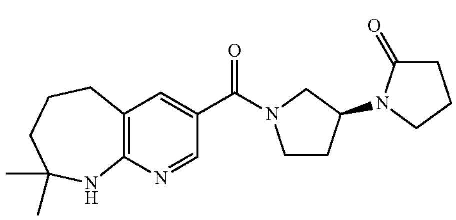 [SMILES: CC1(C)CCCc2cc(C(=O)N3CC[C@H](N4CCCC4=O)C3)cnc2N1] | 1.5 | |

TABLE I-continued

Biological properties of representatives of the present invention

| Ex. | Structure | VNN 1 IC$_{50}$ (nM) | HWB IC$_{50}$ (nM) |
|---|---|---|---|
| 12.6 | 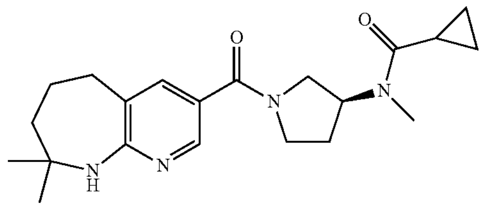 [SMILES: CN(C(=O)C1CC1)[C@H]1CCN(C(=O)c2cnc3c(c2)CCCC(C)(C)N3)C1] | 2.7 | |
| 12.7 | 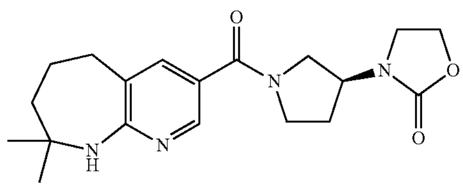 [SMILES: CC1(C)CCCc2cc(C(=O)N3CC[C@H](N4CCOC4=O)C3)cnc2N1] | 1.4 | |
| 13.1 | 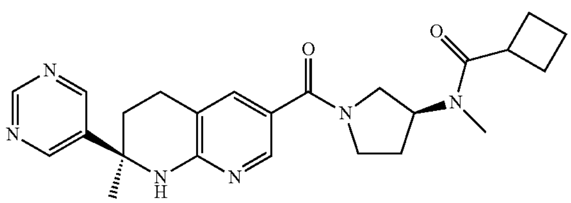 [SMILES: CN(C(=O)C1CCC1)[C@H]1CCN(C(=O)c2cnc3c(c2)CC[C@](C)(c2cncnc2)N3)C1] | 0.2 | |
| 13.2 | 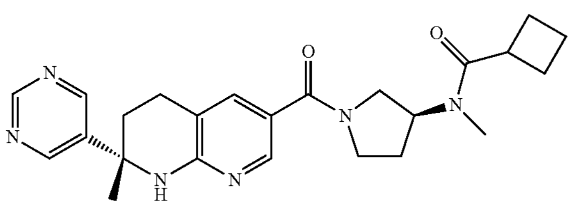 [SMILES: CN(C(=O)C1CCC1)[C@H]1CCN(C(=O)c2cnc3c(c2)CC[C@@](C)(c2cncnc2)N3)C1] | 23.5 | |
| 13.3 | 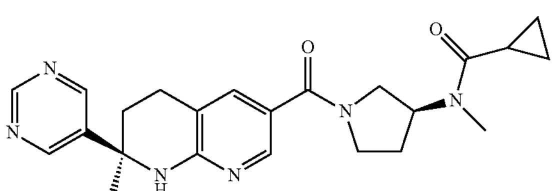 | 0.3 | |
| 13.4 | 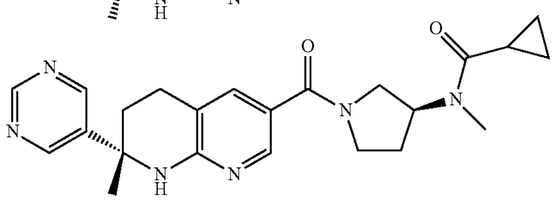 | 11.5 | |

The invention claimed is:

1. A compound of the formula I,

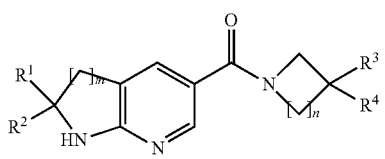

or a pharmaceutically acceptable salt thereof, wherein n denotes 1, 2 or 3;

m denotes 1, 2 or 3;

$R^1$ and $R^2$ are independently from each other selected from the group consisting of H, $C_{1-4}$-alkyl optionally substituted by 1-3 F-atoms or $C_{1-2}$-alkoxy, 6-10 membered aryl substituted by $R^{2.1}$ and 5-6 membered heteroaryl substituted by $R^{2.1}$, wherein $R^{2.1}$ is selected from the group consisting of H, F, Cl, Br, —CN, $NR^{2.1.1}R^{2.1.2}$, —$SO_2R^{2.1.3}$ and —$OR^{2.1.4}$, wherein
$R^{2.1.1}$, $R^{2.1.2}$ independently from each other denote H, $C_{1-4}$-alkyl or $C_{3-4}$-cycloalkyl;
or
$R^{2.1.1}$ and $R^{2.1.2}$ together with the N-atom to which they are attached form a 4-5 membered heterocyclyl or a 6 membered heterocyclyl optionally containing one additional heteroatom selected from the group consisting of N and O;
$R^{2.1.3}$, denotes $C_{1-4}$-alkyl or $NR^{2.1.1} R^{2.1.2}$,
$R^{2.1.4}$ is selected from the group consisting of H, $C_{1-4}$-alkyl, $C_{3-5}$-cycoalkyl, 4-5 membered heterocyclyl containing 1 heteroatom selected from the group consisting of N and O;
wherein in the definition of $R^{2.1.1}$, $R^{2.1.2}$, $R^{2.1.3}$ and $R^{2.1.4}$ mentioned alkyl, cycloalkyl and heterocyclyl are optionally substituted by 1-3 F-atoms or one $C_{1-2}$-alkoxy;
or
$R^1$ and $R^2$ together may form a 3-5 membered carbocycle or 4-6 membered heterocyclyl containing one heteroatom selected from the group consisting of N and O;
$R^3$ denotes $NR^{3.1}R^{3.2}$;
or
$R^3$ denotes a group of formula $R^{3.a}$ or $R^{3.b}$

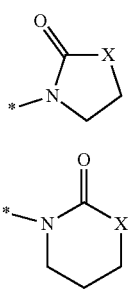

$R^{3.a}$ $R^{3.b}$ wherein
X denotes $CH_2$, $NR^X$ or O;
wherein $R^X$ denotes H or $C_{1-3}$-alkyl;
$R^{3.1}$ is selected from the group consisting of $C_{1-4}$-alkyl-CO— optionally substituted by 1-3 F-atoms, $C_{3-4}$-cycloalkyl or $C_{1-2}$-alkoxy, $R^{3.1.3}R^{3.1.4}N$—CO—, $R^{3.1.5}O$—CO—, pyrimidine, pyridine, $C_{3-5}$-cycloalkyl-CO— substituted with $R^{3.1.1}$ and $R^{3.1.2}$, 4-6-membered-heterocyclyl-CO— substituted with $R^{3.1.1}$ and $R^{3.1.2}$, —CO-phenyl substituted with $R^{3.1.1}$ and $R^{3.1.2}$;
wherein
$R^{3.1.1}$, $R^{3.1.2}$ independently from each other are selected from the group consisting of H, $CH_3$, —$OR^{3.1.1.1}$, F and —CN;
$R^{3.1.3}$, $R^{3.1.4}$ independently from each other denote H, $C_{1-4}$-alkyl or $C_{3-4}$-cycloalkyl;
or
$R^{3.1.3}$ and $R^{3.1.4}$ together with the N-atom to which they are attached form a form a 4-5 membered heterocyclyl or a 6 membered heterocyclyl optionally containing one additional heteroatom selected from the group consisting of N and O;
$R^{3.1.5}$ is selected from the group consisting of $C_{1-4}$-alkyl, $C_{3-5}$-cycloalkyl, 4-5 membered heterocyclyl and $C_{3-4}$-cycloalkyl-$CH_2$—;

$R^{3.1.1.1}$ denotes $C_{1-4}$-alkyl, $C_{3-5}$-cycloalkyl or 4-5 membered heterocyclyl;
wherein in the definition of $R^{3.1.1}$, $R^{3.1.2}$, $R^{3.1.3}$, $R^{3.1.4}$, $R^{3.1.5}$ and $R^{3.1.1.1}$ mentioned alkyl, cycloalkyl and heterocyclyl are optionally substituted by 1-3 F-atoms or one $C_{1-2}$-alkoxy;
$R^{3.2}$ is selected from the group consisting of H, $C_{1-4}$-alkyl, $C_{3-4}$-cycloalkyl, $C_{3-4}$-cycloalkyl-$C_{1-2}$-alkyl- and phenyl-$C_{1-2}$-alkyl-;
wherein in the definition of $R^{3.2}$ mentioned alkyl, cycloalkyl and phenyl are optionally substituted by 1-3 F-atoms or one $C_{1-2}$-alkoxy;
$R^4$ denotes hydrogen or $C_{1-4}$-alkyl optionally substituted with 1 to 3 F-atoms;
or
$R^3$ and $R^4$ together form a 4-6-membered heterocycle containing one oxygen atom.

2. The compound according to claim 1,
wherein
m denotes 1,
or a pharmaceutically acceptable salt thereof.

3. The compound according to claim 1,
wherein
m denotes 2,
or a pharmaceutically acceptable salt thereof.

4. The compound according to claim 1,
wherein
n denotes 1 or 2,
or a pharmaceutically acceptable salt thereof.

5. The compound according to claim 1, wherein
$R^1$ denotes H or methyl,
or a pharmaceutically acceptable salt thereof.

6. The compound according to claim 1, wherein
$R^2$ denotes methyl, ethyl, pyrimidin or phenyl substituted by $R^{2.1}$, wherein
$R^{2.1}$ is selected from the group consisting of H, F, Cl and —CN,
or a pharmaceutically acceptable salt thereof.

7. The compound according to claim 1, wherein
$R^3$ denotes $NR^{3.1}R^{3.2}$,
or
$R^3$ denotes a group of formula $R^{3.a}$

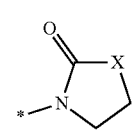

$R^{3.a}$ wherein
X denotes $CH_2$ or O
$R^{3.1}$ denotes —$COCH_3$, pyrimidine, $C_{3-4}$-cycloalkyl-CO— substituted with $R^{3.1.1}$ and $R^{3.1.2}$
wherein
$R^{3.1.1}$, $R^{3.1.2}$ independently from each other denote H, $CH_3$, F or —CN
$R^{3.2}$ denotes $CH_3$,
or a pharmaceutically acceptable salt thereof.

8. The compound according to claim 1, wherein
$R^3$ and $R^4$ together form a 6 membered heterocycle containing one oxygen atom, or a pharmaceutically acceptable salt thereof.

9. The compound according to claim 1, wherein
$R^4$ denotes hydrogen,
or a pharmaceutically acceptable salt thereof.

10. The compound according to claim 1, wherein
n denotes 1 or 2;
m denotes 1;
R¹ denotes methyl,
R² denotes methyl or phenyl substituted by $R^{2.1}$,
  wherein
    $R^{2.1}$ is selected from the group consisting of H, F, Cl and —CN;
R³ denotes $NR^{3.1}R^{3.2}$;
or
R³ denotes a group of formula $R^{3.a}$,

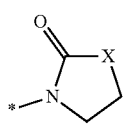

wherein
X denotes $CH_2$ or O;
$R^{3.1}$ denotes —$COCH_3$, pyrimidine, $C_{3-4}$-cycloalkyl-CO— substituted with $R^{3.1.1}$ and $R^{3.1.2}$
  wherein
    $R^{3.1.1}$, $R^{3.1.2}$ independently from each other denote H, —$CH_3$, F or —CN;
$R^{3.2}$ denotes $CH_3$,
R⁴ denotes hydrogen;
or
R³ and R⁴ together form a 6 membered heterocycle containing one oxygen atom;
or a pharmaceutically acceptable salt thereof.

11. The compound according to claim 1, wherein
n denotes 1 or 2;
m denotes 2;
R¹ denotes H or methyl;
R² denotes methyl, ethyl, pyrimidin or phenyl;
R³ denotes $NR^{3.1}R^{3.2}$;
or
R³ denotes a group of formula $R^{3.a}$;

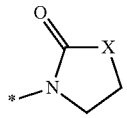

wherein
X denotes $CH_2$ or O;
$R^{3.1}$ denotes —$COCH_3$, pyrimidine $C_{3-4}$-cycloalkyl-CO— substituted with $R^{3.1.1}$ and $R^{3.1.2}$,
  wherein
    $R^{3.1.1}$, $R^{3.1.2}$ independently from each other denote H, $CH_3$, F or —CN;
$R^{3.2}$ denotes $CH_3$,
R⁴ denotes hydrogen,
or
R³ and R⁴ together form a 6 membered heterocycle containing one oxygen atom;
or a pharmaceutically acceptable salt thereof.

12. The compound of formula I according to claim 1 selected from the group consisting of examples 6, 9.1, 8.2, 5.3, 2.1, 7.2, 13.3, 5.2, 13.1, 4.1, 11.10, 4.4, 11.9, 7.4, 4.3, 7.1, 8.3, 11.6, 10 and 9.3;

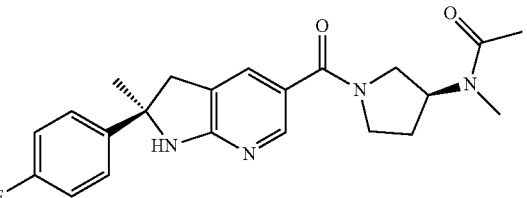

Ex. 6

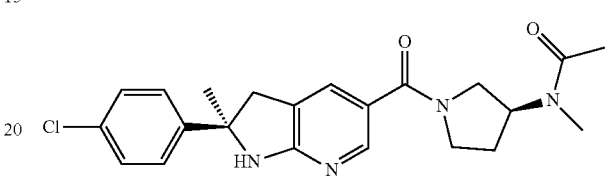

Ex. 9.1

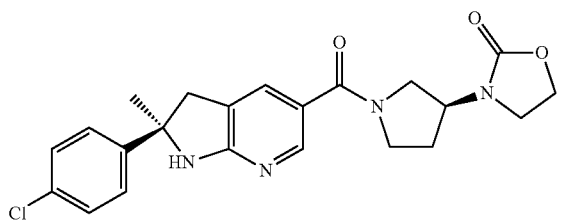

Ex. 8.2

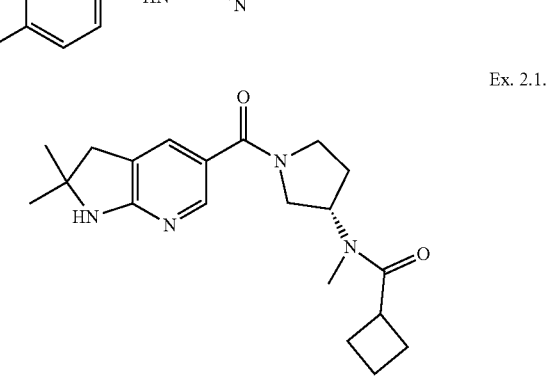

Ex. 5.3

Ex. 2.1.

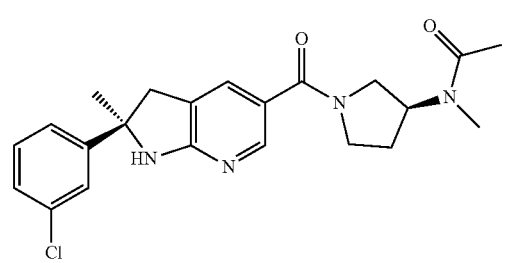

Ex 7.2

Ex. 13.3
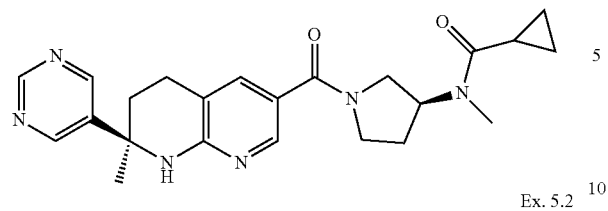
Ex. 5.2
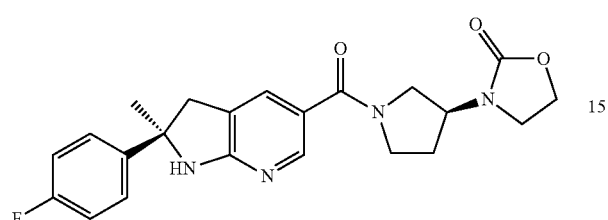
Ex. 13.1
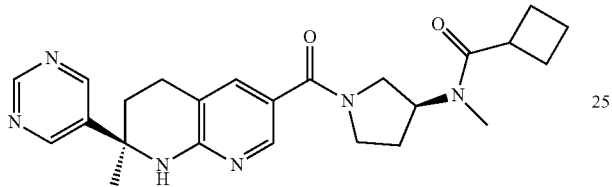
Ex. 4.1
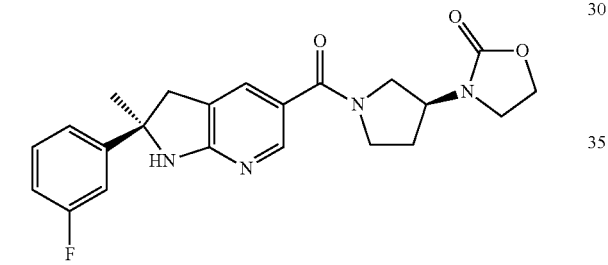
Ex. 11.10
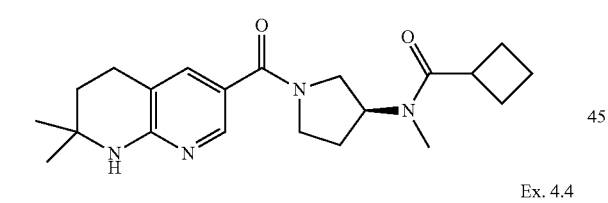
Ex. 4.4
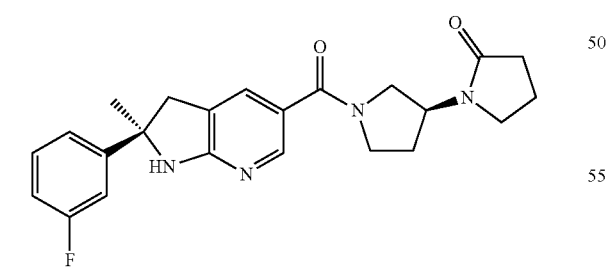
Ex. 11.9
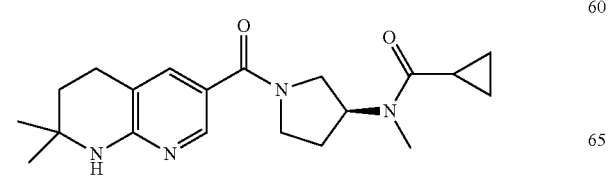
Ex. 7.4
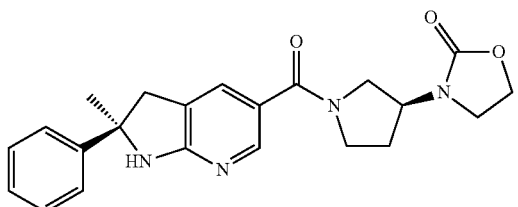
Ex. 4.3
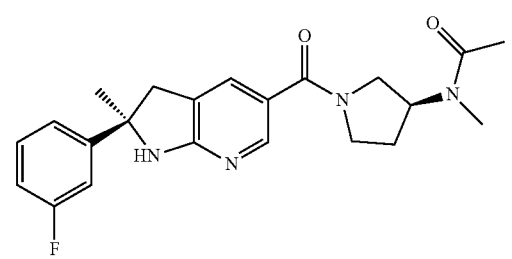
Ex. 7.1
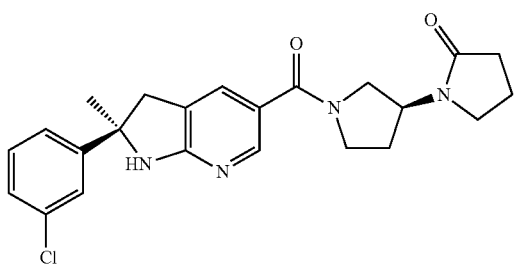
Ex. 9.3
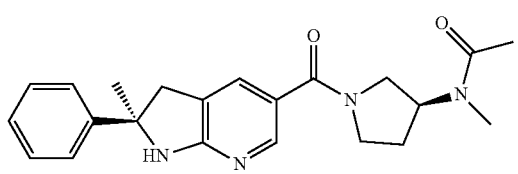
Ex. 8.3
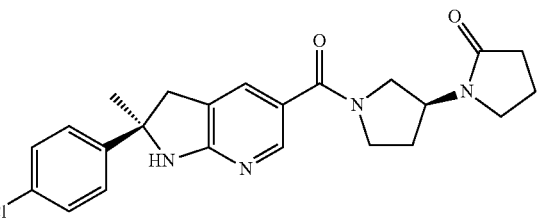
Ex. 11.6

-continued

Ex. 10

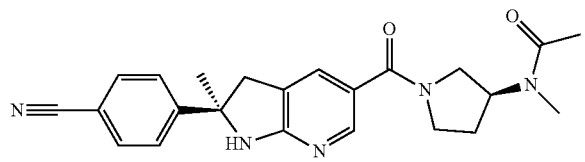

or a pharmaceutically acceptable salt thereof.

13. A pharmaceutical composition comprising a therapeutically effective amount of at least one compound of formula I according to claim 1 or a pharmaceutically acceptable salt thereof and one or more pharmaceutically acceptable excipients.

14. A method of treating a patient suffering from Crohn's disease, ulcerative colitis, atopic dermatitis, systemic sclerosis, Non-Alcoholic Steatohepathitis (NASH), psoriasis, chronic kidney disease, chronic obstructive pulmonary disease, idiopathic pulmonary fibrosis, rheumatoid arthritis, scleroderma, asthma, allergic rhinitis, allergic eczema, juvenile rheumatoid arthritis, juvenile idiopathic arthritis, graft versus host disease, psoriatic arthritis, Hyperlipidemia, colorectal cancer or pancreatic cancer related new onset diabetes, comprising administering to the patient the compound according to claim 1.

15. A pharmaceutical composition comprising additionally to the compound of claim 1, a pharmaceutically active compound selected from the group consisting of an immunomodulatory agent, anti-inflammatory agent and a chemotherapeutic agent.

16. A compound of formula:

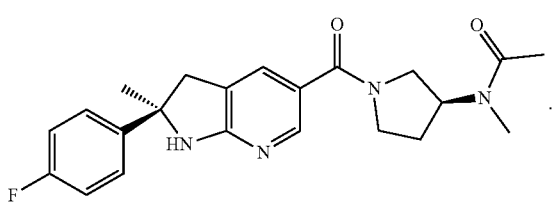 [SMILES: CC(=O)N(C)[C@H]1CCN(C(=O)c2cnc3c(c2)C[C@](C)(c2ccc(F)cc2)N3)C1]

17. A compound of formula:

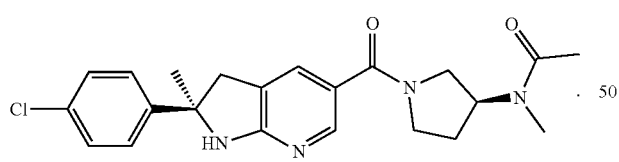

18. A compound of formula:

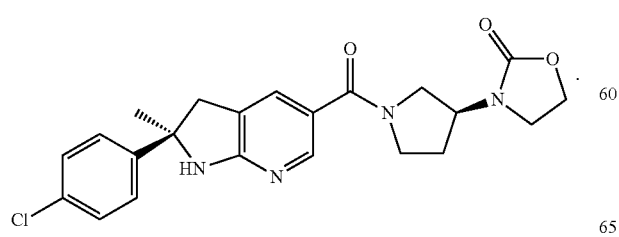

19. A compound of formula:

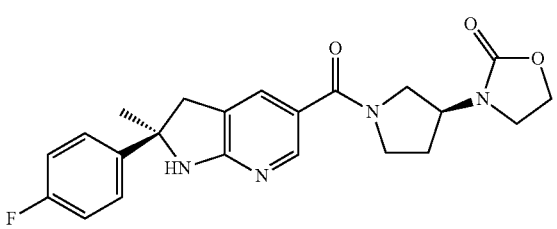

20. A compound of formula:

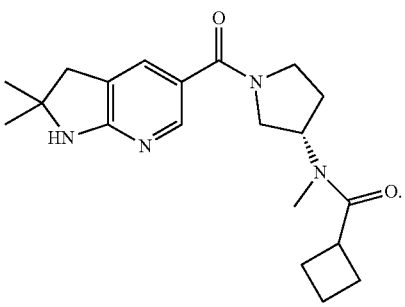 [SMILES: CN(C(=O)C1CCC1)[C@H]1CCN(C(=O)c2cnc3c(c2)CC(C)(C)N3)C1]

21. A compound of formula:

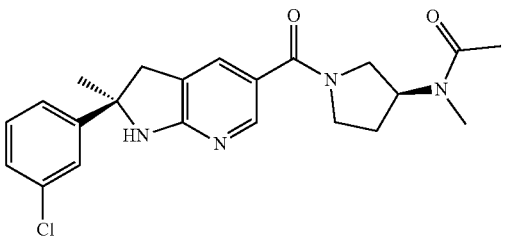

22. A compound of formula:

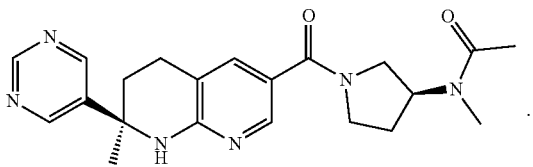 [SMILES: CC(=O)N(C)[C@H]1CCN(C(=O)c2cnc3c(c2)CC[C@](C)(c2cncnc2)N3)C1]

23. A compound of formula:

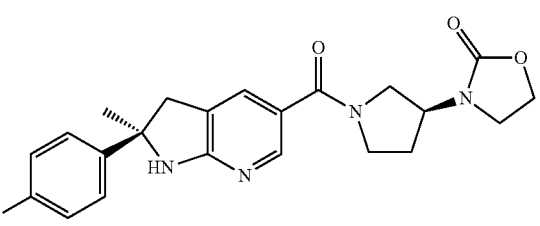

24. A compound of formula:
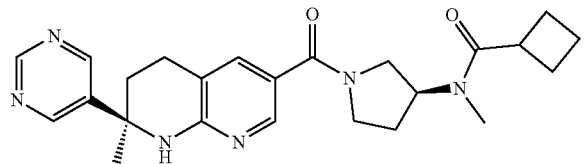 [SMILES: CN(C(=O)C1CCC1)[C@H]1CCN(C(=O)c2cnc3c(c2)CC[C@](C)(c2cncnc2)N3)C1]
25. A compound of formula:
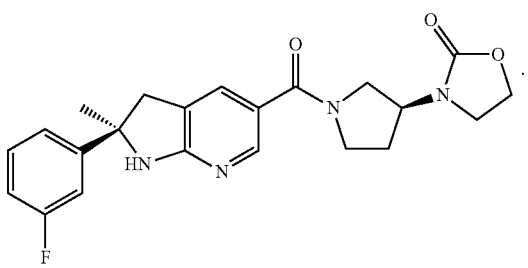 [SMILES: C[C@]1(c2cccc(F)c2)Cc2cc(C(=O)N3CC[C@H](N4CCOC4=O)C3)cnc2N1]
26. A compound of formula:
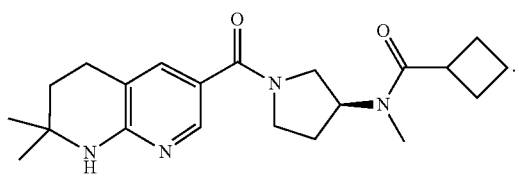 [SMILES: CN(C(=O)C1CCC1)[C@H]1CCN(C(=O)c2cnc3c(c2)CCC(C)(C)N3)C1]
27. A compound of formula:
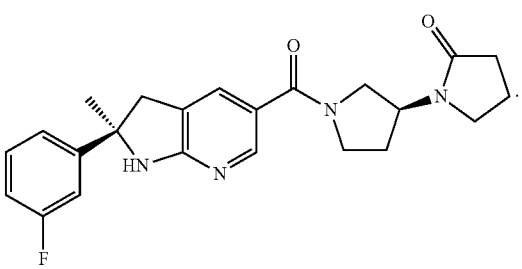 [SMILES: C[C@]1(c2cccc(F)c2)Cc2cc(C(=O)N3CC[C@H](N4CCCC4=O)C3)cnc2N1 ; "."]
28. A compound of formula:
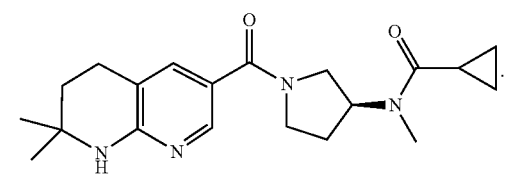 [SMILES: CN(C(=O)C1CC1)[C@H]1CCN(C(=O)c2cnc3c(c2)CCC(C)(C)N3)C1]
29. A compound of formula:
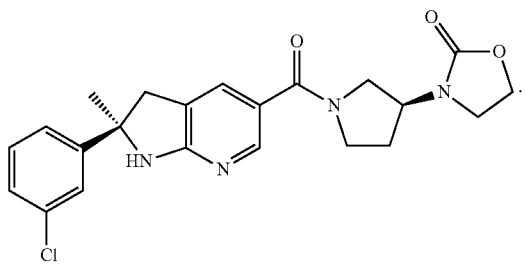 [SMILES: C[C@]1(c2cccc(Cl)c2)Cc2cc(C(=O)N3CC[C@H](N4CCOC4=O)C3)cnc2N1 ; "."]
30. A compound of formula:
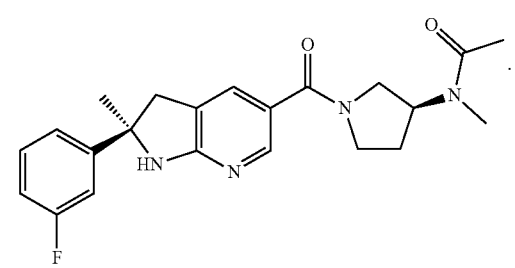 [SMILES: CC(=O)N(C)[C@H]1CCN(C(=O)c2cnc3c(c2)C[C@](C)(c2cccc(F)c2)N3)C1]
31. A compound of formula:
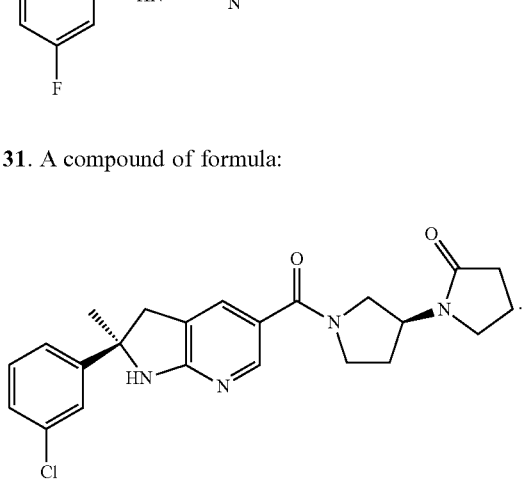
32. A compound of formula:
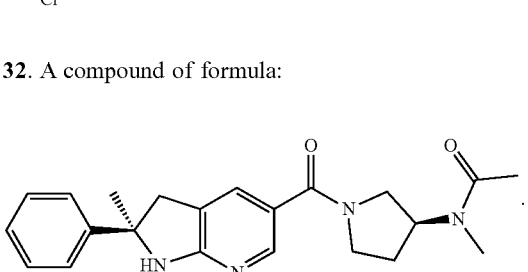
33. A compound of formula:
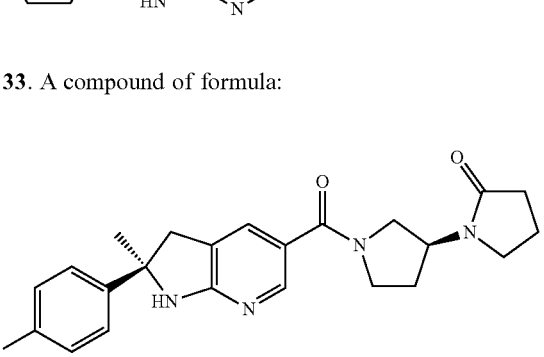

34. A compound of formula:

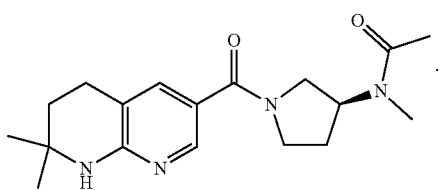 [SMILES: CC(=O)N(C)[C@H]1CCN(C(=O)c2cnc3c(c2)CCC(C)(C)N3)C1 ; "."]

35. A compound of formula:

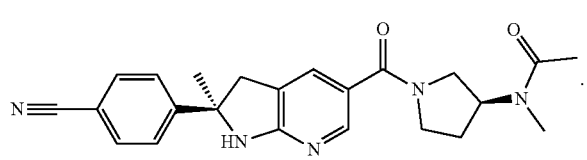 [SMILES: CC(=O)N(C)[C@H]1CCN(C(=O)c2cnc3c(c2)C[C@](C)(c2ccc(C#N)cc2)N3)C1]

36. A compound of formula:

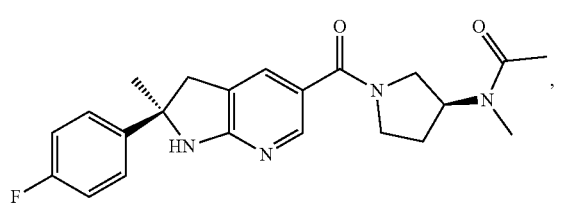 [SMILES: CC(=O)N(C)[C@H]1CCN(C(=O)c2cnc3c(c2)C[C@](C)(c2ccc(F)cc2)N3)C1]

or a pharmaceutically acceptable salt thereof.

37. A compound of formula:

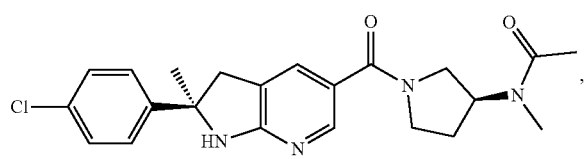 [SMILES: CC(=O)N(C)[C@H]1CCN(C(=O)c2cnc3c(c2)C[C@](C)(c2ccc(Cl)cc2)N3)C1]

or a pharmaceutically acceptable salt thereof.

38. A compound of formula:

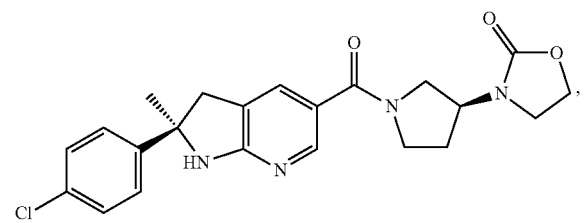 [SMILES: C[C@]1(c2ccc(Cl)cc2)Cc2cc(C(=O)N3CC[C@H](N4CCOC4=O)C3)cnc2N1 ; ","]

or a pharmaceutically acceptable salt thereof.

39. A compound of formula:

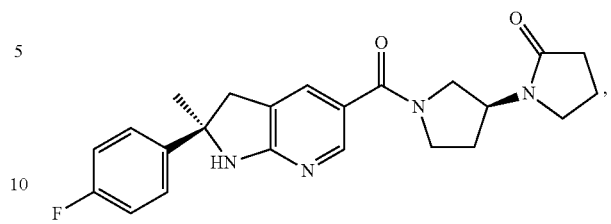

or a pharmaceutically acceptable salt thereof.

40. A compound of formula:

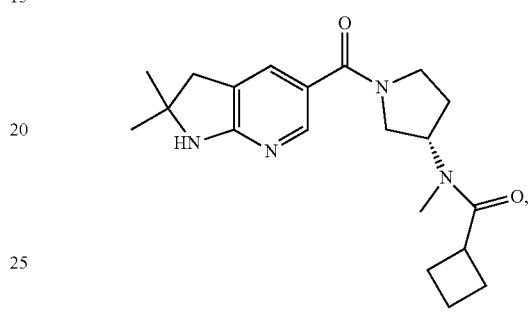

or a pharmaceutically acceptable salt thereof.

41. A compound of formula:

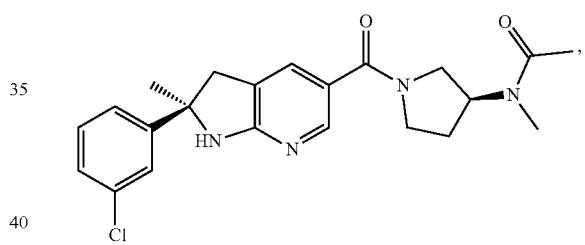

or a pharmaceutically acceptable salt thereof.

42. A compound of formula:

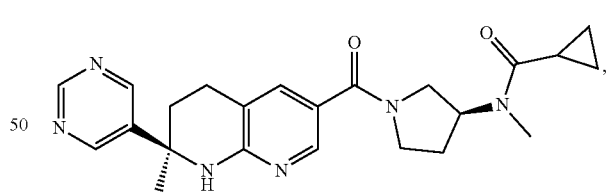

or a pharmaceutically acceptable salt thereof.

43. A compound of formula:

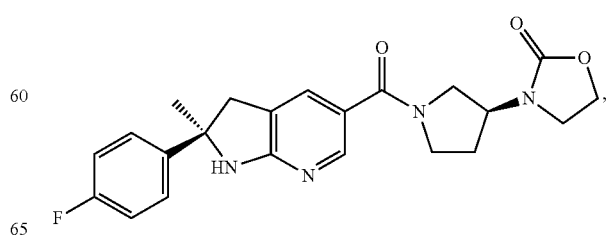

or a pharmaceutically acceptable salt thereof.

44. A compound of formula:

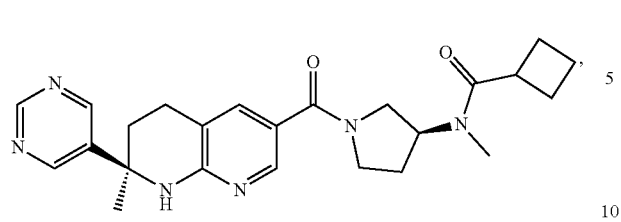

or a pharmaceutically acceptable salt thereof.

45. A compound of formula:

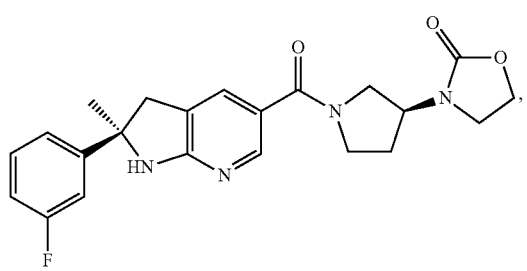

or a pharmaceutically acceptable salt thereof.

46. A compound of formula:

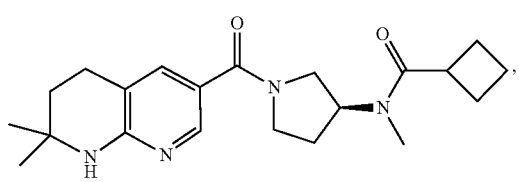 [SMILES: CN(C(=O)C1CCC1)[C@H]1CCN(C(=O)c2cnc3c(c2)CCC(C)(C)N3)C1]

or a pharmaceutically acceptable salt thereof.

47. A compound of formula:

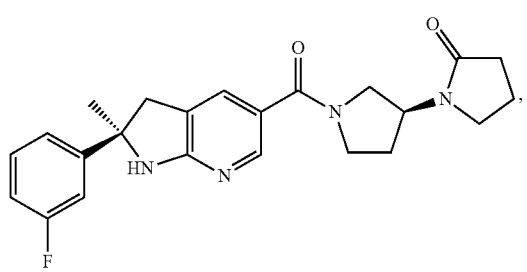

or a pharmaceutically acceptable salt thereof.

48. A compound of formula:

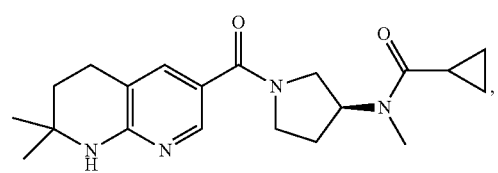 [SMILES: CN(C(=O)C1CC1)[C@H]1CCN(C(=O)c2cnc3c(c2)CCC(C)(C)N3)C1]

or a pharmaceutically acceptable salt thereof.

49. A compound of formula:

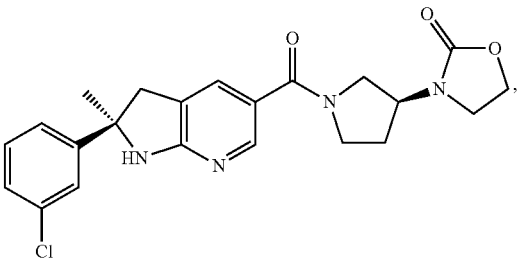

or a pharmaceutically acceptable salt thereof.

50. A compound of formula:

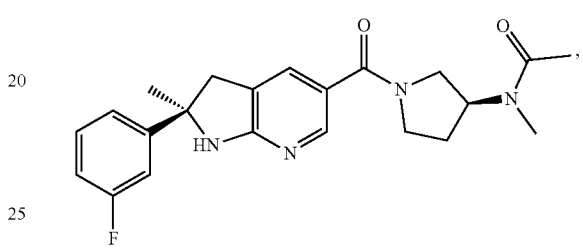

or a pharmaceutically acceptable salt thereof.

51. A compound of formula:

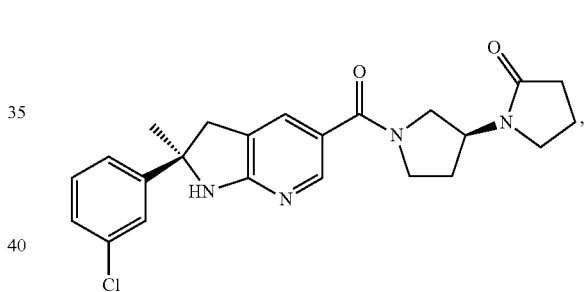

or a pharmaceutically acceptable salt thereof.

52. A compound of formula:

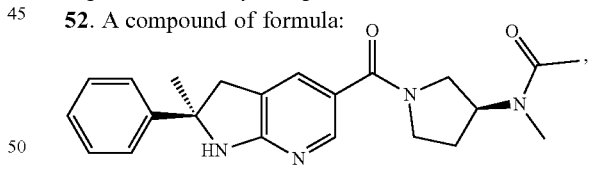

or a pharmaceutically acceptable salt thereof.

53. A compound of formula:

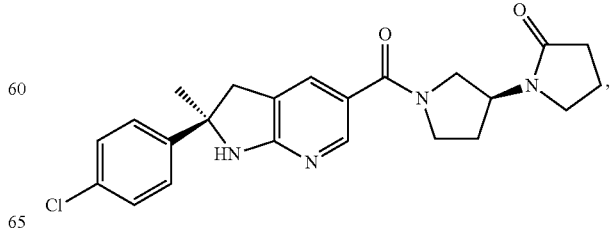

or a pharmaceutically acceptable salt thereof.

54. A compound of formula:
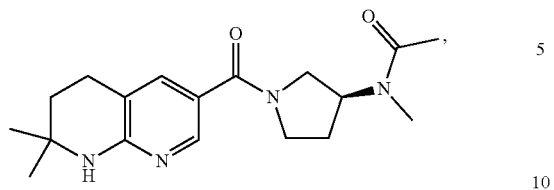
or a pharmaceutically acceptable salt thereof.
55. A compound of formula:
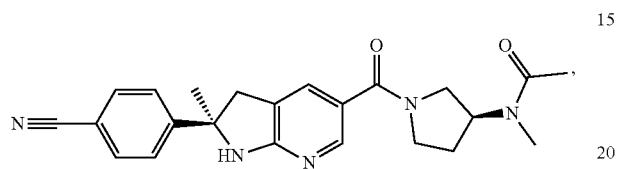
or a pharmaceutically acceptable salt thereof.
* * * * *